US010234557B2

United States Patent
Honjo et al.

(10) Patent No.: US 10,234,557 B2
(45) Date of Patent: Mar. 19, 2019

(54) SIGNAL PROCESSING APPARATUS

(71) Applicant: Toshiba Medical Systems Corporation, Otawara-shi (JP)

(72) Inventors: Yasunori Honjo, Otawara (JP); Yasuhiko Abe, Otawara (JP); Tetsuya Kawagishi, Nasushiobara (JP); Akihiro Kakee, Nasushiobara (JP); Takeshi Sato, Nasushiobara (JP); Makoto Hirama, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 760 days.

(21) Appl. No.: 14/709,628

(22) Filed: May 12, 2015

(65) Prior Publication Data
US 2015/0324957 A1 Nov. 12, 2015

(30) Foreign Application Priority Data

May 12, 2014 (JP) .................................. 2014-099077

(51) Int. Cl.
*G01S 15/00* (2006.01)
*G01S 15/89* (2006.01)
*G06T 5/00* (2006.01)
*A61B 8/14* (2006.01)
*A61B 8/00* (2006.01)
(Continued)

(52) U.S. Cl.
CPC .......... *G01S 15/8995* (2013.01); *A61B 8/145* (2013.01); *A61B 8/4494* (2013.01); *A61B 8/461* (2013.01); *A61B 8/5246* (2013.01); *A61B 8/5253* (2013.01); *A61B 8/5269* (2013.01); *A61B 8/54* (2013.01); *G01S 7/52046* (2013.01); *G01S 7/52077* (2013.01); *G01S 15/8915* (2013.01); *G01S 15/8925* (2013.01); *G06T 5/002* (2013.01); *G06T 2207/10132* (2013.01);
(Continued)

(58) Field of Classification Search
CPC ....... G01S 7/52046; A61B 8/00; A61B 8/145; A61B 8/4494; A61B 8/461
See application file for complete search history.

(56) References Cited

U.S. PATENT DOCUMENTS

| 6,113,547 A * | 9/2000 | Catallo ................ G01S 7/003 600/459 |
| 2006/0173313 A1* | 8/2006 | Liu ................. G01S 7/52046 600/437 |
| 2009/0141957 A1 | 6/2009 | Yen et al. |

FOREIGN PATENT DOCUMENTS

JP 4615950 1/2011

OTHER PUBLICATIONS

U.S. Appl. No. 14/612,458, filed Feb. 3, 2015, Yasunori Honjo et al.
(Continued)

Primary Examiner — Joseph M Santos Rodriguez
(74) Attorney, Agent, or Firm — Oblon, McClelland, Maier & Neustadt, L.L.P.

(57) ABSTRACT

A signal processing apparatus of an embodiment includes processing circuitry and control circuitry. The processing circuitry acquires a plurality of IQ signals obtained by performing a plurality of processing with different conditions on reflected wave signals generated at a transducer element included in an ultrasound probe. The processing circuitry generates a compound signal compounded by non-linear processing of the IQ signals. The control circuitry causes a display to display image data based on the compound signal.

16 Claims, 29 Drawing Sheets

(51) Int. Cl.
    *A61B 8/08* (2006.01)
    *G01S 7/52* (2006.01)
(52) U.S. Cl.
    CPC ............... *G06T 2207/20182* (2013.01); *G06T 2207/20221* (2013.01)

(56) References Cited

OTHER PUBLICATIONS

U.S. Appl. No. 14/688,373, filed Apr. 16, 2015, Yasuhiko Abe et al.
Chi Hyung Seo et al. "Sidelobe Suppression in Ultrasound Imaging Using Dual Apodization with Cross-Correlation", IEEE Transactions on Ultrasonics, Ferroelectrics and Frequency Control, vol. 55, No. 10, Oct. 2008, 12 pages.

\* cited by examiner

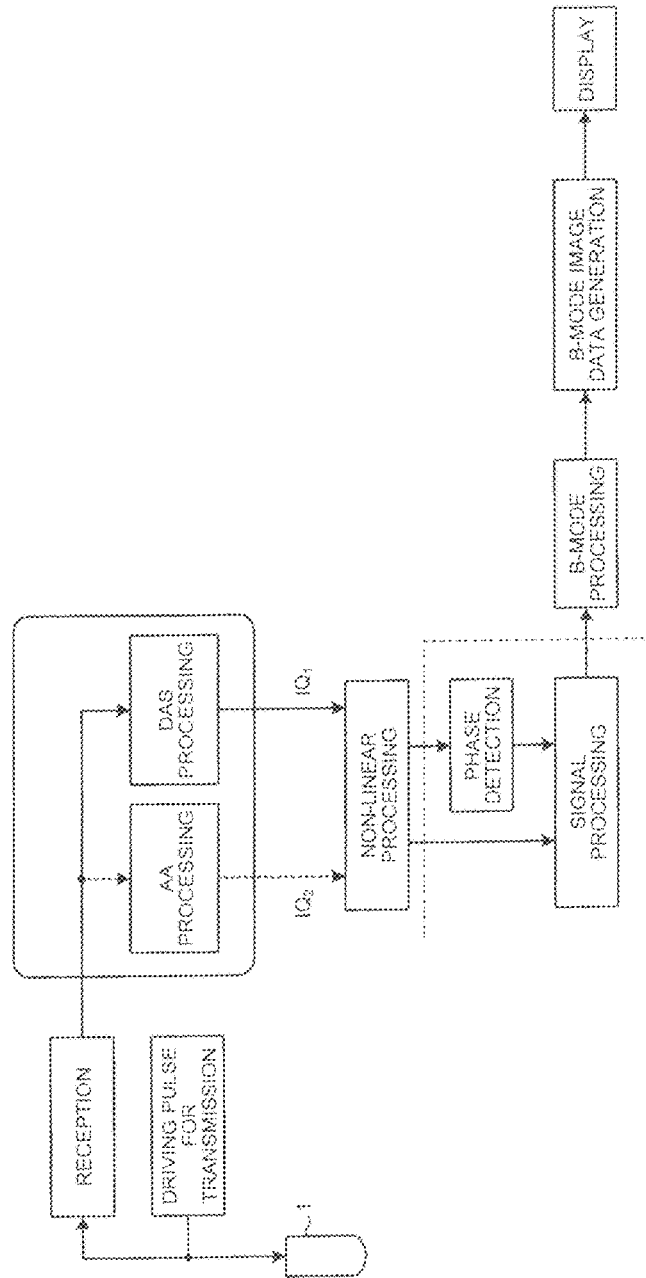

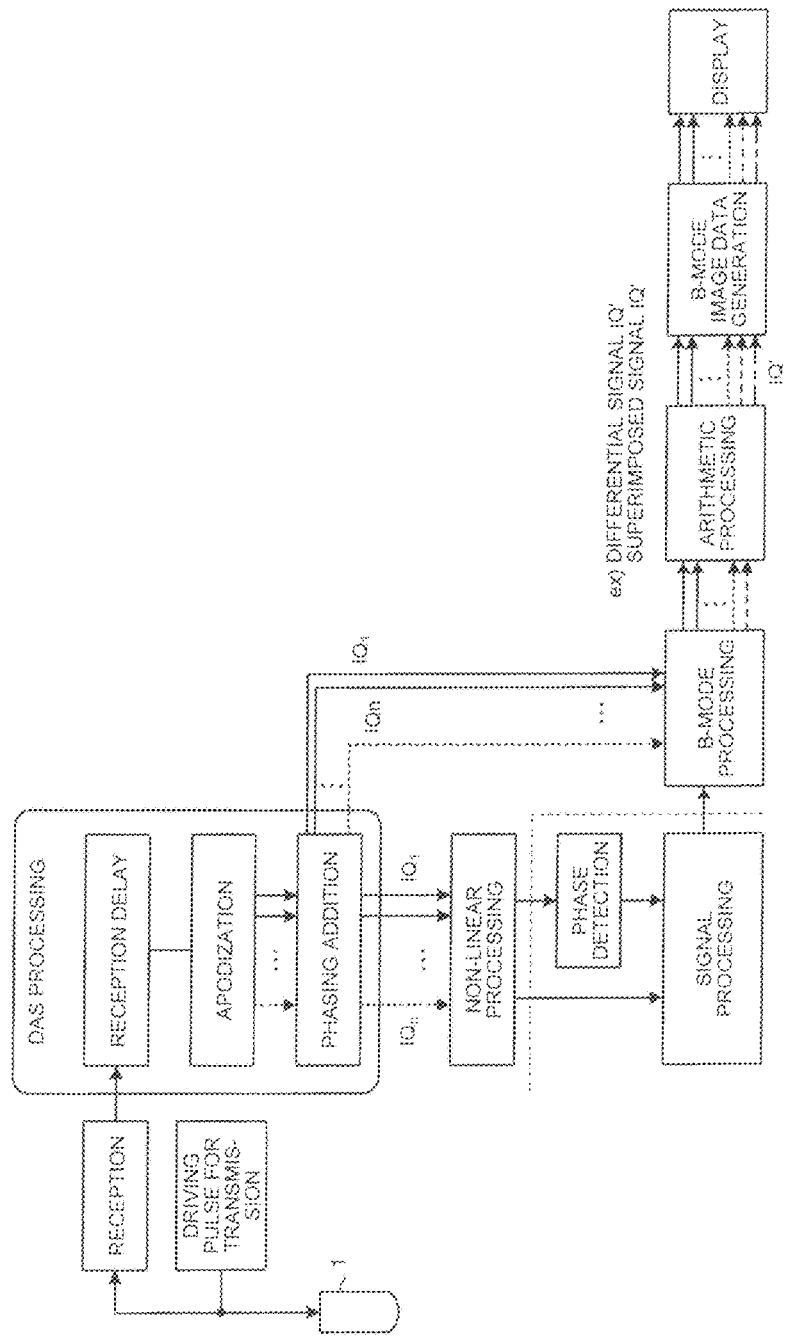

SIGNAL PROCESSING APPARATUS

CROSS-REFERENCE TO RELATED APPLICATIONS

This application is based upon and claims the benefit of priority from Japanese Patent Application No. 2014-99077, filed on May 12, 2014, the entire contents of all of which are incorporated herein by reference.

FIELD

Embodiments described herein relate generally to a signal processing apparatus.

BACKGROUND

Conventionally, various methods have been applied to reduce noise (multiple reflection signals and side lobes, for example) of an ultrasonic image (B-mode image) that interferes with a diagnosis. For example, for reducing multiple reflection signals, a method of compounding a plurality of B-mode images with various deflection angles in ultrasonic wave transmission/reception by signal averaging has been known.

In the conventional methods, however, enhancing a noise reducing effect often incurs a trade-off such as removing inherent reflected signals, degrading image resolution, or impairing real-time generation and display of images, which is an advantage of ultrasonography apparatuses.

BRIEF DESCRIPTION OF THE DRAWINGS

FIG. 18 is a diagram (2) for explaining the fourth embodiment;
FIG. 19 is a diagram (1) for explaining a fifth embodiment;

DETAILED DESCRIPTION

A signal processing apparatus of an embodiment includes processing circuitry and control circuitry. The processing circuitry acquires a plurality of IQ signals obtained by performing a plurality of processing with different conditions on reflected wave signals generated at a transducer element included in an ultrasound probe. The processing circuitry generates a compound signal compounded by nonlinear processing of the IQ signals. The control circuitry causes a display to display image data based on the compound signal.

Embodiments of the ultrasonography apparatus as one example of the signal processing apparatus are explained in detail below with reference to the accompanying drawings.

First Embodiment

Figure 1:
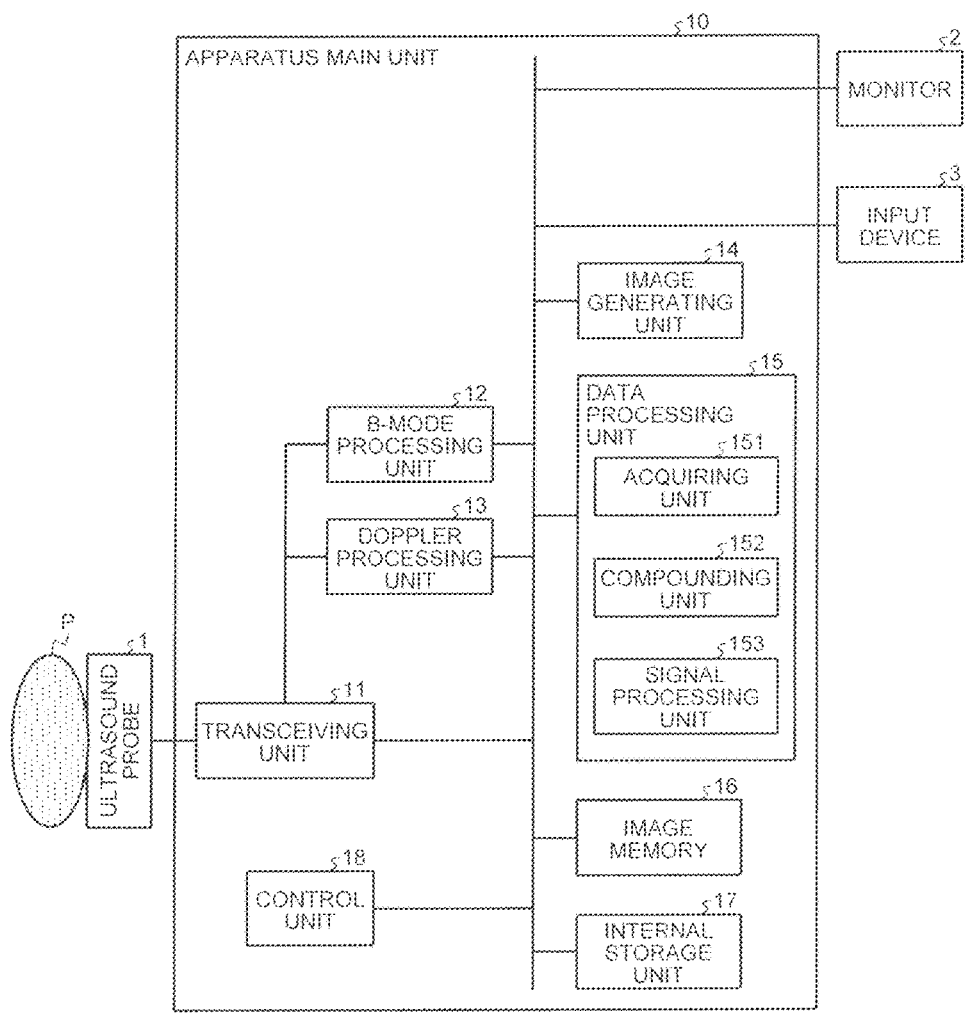
FIG. 1 is a block diagram indicating a configuration example of an ultrasonography apparatus according to a first embodiment.

First, a configuration of an ultrasonography apparatus according to a first embodiment is explained. FIG. 1 is a block diagram indicating a configuration example of the ultrasonography apparatus according to the first embodiment. As exemplified in FIG. 1, the ultrasonography apparatus according to the first embodiment includes an ultrasound probe 1, a monitor 2, an input device 3, and an apparatus main unit 10.

The ultrasound probe 1 includes a plurality of transducer elements (for example, piezoelectric transducer elements). These transducer elements generate ultrasonic waves based on a driving signal that is supplied by a transceiving unit 11 described later included in the apparatus main unit 10. Moreover, the transducer elements included in the ultrasound probe 1 each receive a reflected wave from a subject P and convert the reflected wave into an electric signal. Furthermore, the ultrasound probe 1 includes a matching layer that is provided for the transducer elements and backing material to prevent propagation of an ultrasonic wave to a backward direction from the transducer elements, and the like.

When ultrasonic waves are transmitted to the subject P from the ultrasound probe 1, the transmitted ultrasonic waves are sequentially reflected on a discontinuous surface of acoustic impedance in a tissue of the subject P, and received by the transducer elements included in the ultrasound probe 1 as reflected wave signals. The amplitude of the received reflected wave signals is dependent on a difference in the acoustic impedance on the discontinuous surface on which the ultrasonic waves are reflected. When transmitted ultrasonic wave pulses are reflected on a surface of a moving bloodstream, a cardiac wall, and the like, reflected wave signals have frequency shifts dependent on a velocity component of a moving body relative to a direction of transmission of the ultrasonic waves by the Doppler effect.

The ultrasound probe 1 is detachably connected to the apparatus main unit 10. When two-dimensionally scanning the subject P, an operator connects, for example, a one-dimensional (1D) array probe in which a plurality of piezo-electric transducer elements are arranged in a single row to the apparatus main unit 10, as the ultrasound probe 1. The 1D array probe is a linear ultrasound probe, a convex ultrasound probe, a sector ultrasound probe, or the like. Furthermore, when three-dimensionally scanning the subject P, an operator connects, for example, a mechanical four-dimensional (4D) probe or a two-dimensional (2D) array probe to the apparatus main unit 10, as the ultrasound probe 1. The mechanical 4D probe is capable of two-dimensional scanning using a plurality of piezoelectric transducer elements that are arranged in a single row in the same manner as the 1D array probe, and is capable of three-dimensional scanning by swinging the piezoelectric transducer elements at a certain angle (swing angle). Moreover, the 2D array probe is capable of three-dimensional scanning by a plurality of piezoelectric transducer elements that are arranged in a matrix, and is capable of two-dimensional scanning by transmitting ultrasonic waves in a converged manner. The following describes a case in which a 1D array probe is connected to the apparatus main unit 10.

The input device 3 includes, for example, a mouse, a keyboard, a button, a panel switch, a touch command screen, a foot switch, a track ball, and a joy stick. The input device 3 receives a request for various kinds of setting from an operator of the ultrasonography apparatus, and transfers the received request for various kinds of setting to the apparatus main unit 10.

The monitor 2 displays a graphical user interface (GUI) for an operator of the ultrasonography apparatus to input a request for various kinds of setting by using the input device 3, or displays ultrasonic image data generated in the apparatus main unit 10, and the like.

The apparatus main unit 10 is an apparatus that generates ultrasonic image data based on a reflected wave signal received by the ultrasound probe 1. The apparatus main unit 10 illustrated in FIG. 1 is an apparatus that can generate two-dimensional ultrasonic image data based on two-dimensional reflected wave data received by the ultrasound probe 1. Furthermore, the apparatus main unit 10 illustrated in FIG. 1 is an apparatus that can generate three-dimensional ultrasonic image data based on three-dimensional reflected wave data received by the ultrasound probe 1.

The apparatus main unit 10 includes the transceiving unit 11, a B-mode processing unit 12, a Doppler processing unit 13, an image generating unit 14, a data processing unit 15, an image memory 16, an internal storage unit 17, and a control unit 18 as illustrated in FIG. 1.

The transceiving unit 11 is a transmission beam former that controls the transmission directivity in transmission of ultrasonic waves. Specifically, the transceiving unit 11 includes a rate pulse generator, a transmission delaying unit, a transmission pulser, and the like, and provides the ultrasound probe 1 with a driving signal. The rate pulse generator generates rate pulses to form transmission ultrasonic waves repeatedly at a certain rate frequency (pulse repetition frequency (PRF)). Each of the rate pulses applies a voltage to the transmission pulser in a state in which a transmission delay time is given to the rate pulse by passing through the transmission delaying unit. That is, the transmission delaying unit gives a transmission delay time for each of the transducer elements that is required to cause ultrasonic waves generated by the ultrasound probe 1 to converge to a beam and to determine the transmission directivity, to each rate pulse generated by the rate pulse generator. The transmission pulser applies a driving signal (driving pulse) to the ultrasound probe 1 at timing based on the rate pulse.

The driving pulse is transferred to the transducer element inside the ultrasound probe 1 through a cable from the transmission pulser, and then converted into a mechanical vibration from an electrical signal by the transducer element. This mechanical vibration is transmitted as ultrasonic waves in a living body. Ultrasonic waves each having a different transmission delay time for the corresponding transducer element are caused to converge and propagated in a certain transmission direction. The transmission delaying unit varies transmission delay times to be given to the respective rate pulses, to adjust the transmission direction from a surface of the transducer element arbitrarily. The transceiving unit 11 controls the number and positions of transducer elements (transmission aperture) to be used to transmit an ultrasonic beam, and transmission delay times corresponding to the positions of the respective transducer elements structuring the transmission aperture, to give the transmission directivity.

The transceiving unit 11 has a function that is capable of changing a transmission frequency (transmission center frequency), a transmission driving voltage, and the like of an ultrasonic beam instantaneously to execute a certain scan sequence based on an instruction of the control unit 18 described later. In particular, a change in transmission driving voltage is achieved by a linear-amplifier transmission circuit that can change the value instantaneously, or a mechanism of electrically switching a plurality of power supply units.

After reaching the transducer element inside the ultrasound probe 1, a reflected wave of an ultrasonic wave transmitted by the ultrasound probe 1 is converted into an electrical signal (reflected wave signal) from mechanical vibration by the transducer element. The reflected wave signal is input, through a cable, to the transceiving unit 11 functioning as a reception beam former that controls the reception directivity in ultrasonic wave reception.

Specifically, the transceiving unit 11 as the reception beam former has a preamplifier, an analog/digital (A/D) converter, a reception delaying unit, an adding unit, and the like, and generates reflected wave data by performing various kinds of processing on a reflected wave signal received by the ultrasound probe 1. The reflected wave data is converted into ultrasonic image data (B-mode image data), for example, by processing of the B-mode processing unit 12 and the image generating unit 14 described later, to be output to the monitor 2.

The preamplifier performs gain correction processing by amplifying a reflected wave signal per channel. The A/D converter performs A/D conversion of the reflected wave signal subjected to the gain correction, thereby converting the reflected wave signal subjected to the gain correction into digital data. The reception delaying unit gives the digital data a reception delay (reception delay time) that is required to determine the reception directivity. Specifically, the reception delaying unit gives a reception delay time to the digital data based on the distribution of reception delay times (reception delay pattern) for each convergence point calculated from a sonic speed value set in advance as an average sonic speed in a tissue of the subject P for which ultrasonic image is imaged. Accordingly, by giving an output signal of each transducer element the reception delay time by the reception delaying unit, a data string of the signals from the same sample point on a reception scan line is input to the adding unit.

The adding unit performs addition processing (phasing addition processing) of the reflected wave signal (digital data) to which the reception delay time is given by the reception delaying unit. That is, the adding unit adds signals from the same sample point received by the respective transducer elements at the reception aperture. By the addition processing by the adding unit, a reflection component from a direction according to the reception directivity of the reflected wave signal is emphasized. A signal output by the adding unit is output to a processing unit in a later stage as reflected wave data (reception signal).

The transceiving unit 11 as the reception beam former controls the number and positions of transducer elements (reception aperture) to be used to receive reflected waves, and reception delay times corresponding to the positions of the respective transducer elements structuring the reception aperture, to give the reception directivity. The reception delay time varies according to a position of a reception focus together with the position of the transducer element.

The transceiving unit 11 is capable of performing the dynamic variable aperture focus (DVAF) method. In the case of performing the DVAF method, when receiving a signal that is returned from a close position, the transceiving unit 11 decreases a reception aperture width to make a reception beam of a short distance thin. Moreover, in the case of performing the DVAF method, when receiving a signal that is returned from a far position, the transceiving unit 11 increases the reception aperture width according to a distance because as the reception aperture width increases, a stronger focus can be applied. The reception aperture width is set based on an "F-number" set in advance. The "F-number" is a value that is defined by a ratio between the depth of a reception focus and the reception aperture width, and is changed, for example, by an operator arbitrarily. When performing the DVAF method, the transceiving unit 11 changes the reception aperture width at each depth position, according to the "F-number". Specifically, the transceiving unit 11 sets the reception aperture having the reception aperture width that is determined by the reception focus position and the "F-number" such that the reception scan line is in the center.

Furthermore, the transceiving unit 11 performs reception apodization. That is, the adding unit performs addition processing after weighting is performed, by an aperture function (apodization function), on signals (signals input in a state in which the reception delay time is given) from the same sample point received by the respective transducer elements at the reception aperture. For example, the control unit 18 described later creates an aperture function and sets the aperture function to the transceiving unit 11. The aperture function (reception aperture function) is a function to which a weight is assigned to the position of each transducer element. Moreover, the transceiving unit 11 can also perform parallel simultaneous reception in which reflected waves corresponding to a plurality of respective reception scan lines that are obtained with ultrasonic wave transmission performed on one transmission scan line are received simultaneously.

The form of an output signal from the transceiving unit 11 can be a signal including phase information, or can be amplitude information (amplitude signal) subjected to envelope detection processing, and various kinds of forms can be chosen. The signal including phase information is a radio frequency (RF) signal, or an IQ signal that includes an in-phase signal (I-signal) and a quadrature-phase signal (Q-signal) that are extracted from the RF signal. The embodiment explained below describes a case in which the transceiving unit 11 uses an IQ signal to perform various kinds of processing, thereby generating and outputting an IQ signal as reflected wave data of a reception scan line. In one example described above, the transceiving unit 11 is a reception beam former that performs the delay and sum (DAS) method. The transceiving unit 11 illustrated in FIG. 1 may, however, be a reception beam former that generates reflected wave data having the reception directivity based on the adaptive array method, or a reception beam former that can perform both the DAS method and the adaptive array method.

The transceiving unit 11 transmits, when two-dimensionally scanning the subject P, a two-dimensional ultrasonic beam from the ultrasound probe 1. The transceiving unit 11 then generates two-dimensional reflected wave data from a two-dimensional reflected wave signal that is received by the ultrasound probe 1. Furthermore, the transceiving unit 11 transmits, when three-dimensionally scanning the subject P, a three-dimensional ultrasonic beam from the ultrasound probe 1. The transceiving unit 11 then generates three-dimensional reflected wave data from a three-dimensional reflected wave signal that is received by the ultrasound probe 1.

The B-mode processing unit 12 generates data (B-mode data) in which a signal intensity (amplitude intensity) is expressed by the intensity of brightness for each sample point, by performing logarithm amplification, the envelope detection processing, logarithm compression, and the like on the reflected wave data output by the transceiving unit 11.

The Doppler processing unit 13 generates data (Doppler data) in which movement information of a moving body (blood stream and tissue, a contrast-agent echo component, and the like) is extracted based on the Doppler effect, by performing frequency analysis on the reflected wave data output by the transceiving unit 11. Specifically, the Doppler processing unit 13 generates Doppler data in which an average speed, a dispersion value, a power value, and the like are extracted as the movement information of a moving body for a plurality of points.

The B-mode processing unit 12 and the Doppler processing unit 13 are capable of processing both two-dimensional reflected wave data and three-dimensional reflected wave data.

The ultrasonography apparatus illustrated in FIG. 1 can perform harmonic imaging such as contrast harmonic imaging (CHI) and tissue harmonic imaging (THI).

For example, in the harmonic imaging, imaging methods called an amplitude modulation (AM) method, a phase modulation (PM) method, and an AMPM method in which the AM method and the PM method are combined are performed. In the AM method, the PM method, and the AMPM method, transmission of ultrasonic waves having various amplitudes and phases is performed more than one time to the same scan line. Thus, the transceiving unit 11 generates more than one piece of reflected wave data (reception signal) for each scan line. The transceiving unit 11 extracts harmonic components by performing addition/subtraction processing according to a modulation method on the pieces of the reflected wave data of each scan line. Subsequently, the B-mode processing unit 12 performs the envelope detection processing and the like on the reflected wave data (reception signal) of the harmonic components to generate B-mode data.

For example, when the PM method is performed, the transceiving unit 11 transmits ultrasonic waves of the same amplitude for which the phase polarity is reversed, for example, as (−1, 1), two times for each scan line by a scan sequence specified by the control unit 18. The transceiving unit 11 then generates a reception signal by transmission of "−1" and a reception signal by transmission of "1". The transceiving unit 11 then adds these two reception signals. Thus, a signal from which a basic wave component is removed and in which a secondary harmonic component mainly remains is generated. The B-mode processing unit 12 performs the envelope detection processing and the like on this signal, to generate B-mode data of THI or B-mode data of CHI.

Furthermore, in THI, a method of performing visualization using a secondary harmonic component and a difference tone component included in the reception signal has been in practical use. In a visualization method using a difference tone component, for example, a transmission ultrasonic wave having a composite waveform in which a first base wave the center frequency of which is "f1", and a second base wave the center frequency of which is "f2" that is larger than "f1" are combined is transmitted from the ultrasound probe 1. This composite waveform is a waveform in which a waveform of the first base wave and a waveform of the second base wave are combined for which phases thereof are adjusted so that a difference tone component having the same polarity as that of the secondary harmonic component is generated. The transceiving unit 11 transmits the transmission ultrasonic wave of the composite waveform, for example, two times, while reversing the phase. In such a case, the transceiving unit 11 generates two reception signals that respectively correspond to the two times of transmission. The transceiving unit 11 then adds these two reception signals. Thus, a signal from which the base wave component is removed, and in which the difference tone component and the secondary harmonic component mainly remain is generated. The B-mode processing unit 12 performs the envelope detection processing and the like on this signal, to generate B-mode data of THI. The addition/subtraction processing of a plurality of pieces of the reflected wave data (reception signals) for each scan line can be performed by the B-mode processing unit 12.

The image generating unit 14 generates ultrasonic image data from the data that is generated by the B-mode processing unit 12 and the Doppler processing unit 13. That is, the image generating unit 14 generates two-dimensional B-mode image data in which the intensity of a reflected wave is expressed by brightness, from two-dimensional B-mode data generated by the B-mode processing unit 12. Furthermore, the image generating unit 14 generates two-dimensional Doppler image data that indicates moving body information, from two-dimensional Doppler data generated by the Doppler processing unit 13. The two-dimensional Doppler image data is speed image data, dispersion image data, power image data, or image data in which these are combined.

Generally, the image generating unit 14 converts (scan converts) a scan-line signal string of ultrasonic scanning into a scan-line signal string of a video format represented by television and the like, to generate ultrasonic image data for display. Specifically, the image generating unit 14 generates the ultrasonic image data for display by performing coordinate conversion according to a scanning form of an ultrasonic wave by the ultrasound probe 1. Moreover, the image generating unit 14 performs image processing (smoothing) to regenerate a brightness average-value image, image processing (edge enhancement) using a differential filter in an image, and the like as various kinds of image processing other than the scan conversion, by using image frames after scan conversion, for example. Furthermore, the image generating unit 14 composites character information of various kinds of parameters, scales, body marks, and the like with the ultrasonic image data.

The B-mode data and the Doppler data are the ultrasonic image data before performing the scan conversion processing, and data generated by the image generating unit 14 is ultrasonic image data for display after the scan conversion processing is performed. The B-mode data and the Doppler data are also referred to as raw data. The image generating unit 14 has a function that performs the above described smoothing and filtering such as edge enhancement on an amplitude signal obtained by amplitude conversion of reflected wave data, or an image signal obtained by logarithm compression conversion of the amplitude signal. In the following description, the filtering performed by the image generating unit 14 may be described as "raw filtering".

Moreover, the image generating unit 14 generates three-dimensional B-mode image data by performing coordinate conversion on three-dimensional B-mode data generated by the B-mode processing unit 12. Furthermore, the image generating unit 14 generates three-dimensional Doppler image data by performing coordinate conversion on three-dimensional Doppler data generated by the Doppler processing unit 13. That is, the image generating unit 14 generates the "three-dimensional B-mode image data and the three-dimensional Doppler image data" as "three-dimensional ultrasonic image data (volume data)". The image generating unit 14 then performs various kinds of rendering processing on the volume data to generate various kinds of two-dimensional image data to display the volume data on the monitor 2.

The data processing unit 15 is a processing unit that performs various kinds of processing on data generated in the apparatus main unit 10, and as illustrated in FIG. 1, includes an acquiring unit 151, a compounding unit 152, and a signal processing unit 153. Data acquired by the acquiring unit 151 includes a signal obtained by performing phasing addition on signals including phase information (an IQ signal), an amplitude signal obtained by performing phase detection on this signal, and an image signal obtained by performing logarithm compression on this amplitude signal. The compounding unit 152 and the signal processing unit 153 perform various kinds of processing on the data acquired by the acquiring unit 151. The data processing unit 15 according to the first embodiment is described in detail later.

The image memory 16 is a memory that stores therein image data generated by the image generating unit 14. Moreover, the image memory 16 can also store therein data generated by the B-mode processing unit 12 and the Doppler processing unit 13. B-mode data and Doppler data stored in the image memory 16 can be retrieved, for example, by an operator after diagnosis, and are to be ultrasonic image data for display through the image generating unit 14. Furthermore, the image memory 16 can also store therein data output by the transceiving unit 11, or data output by the data processing unit 15.

The internal storage unit 17 stores therein a control program to perform ultrasonic wave transmission/reception, image processing, and display processing, diagnosis information (for example, patient identification (ID), observations of a doctor, and the like), or various kinds of data such as a diagnosis protocol and various kinds of body marks. Moreover, the internal storage unit 17 is also used to archive data stored in the image memory 16, and the like as necessary.

The control unit 18 controls overall processing of the ultrasonography apparatus. Specifically, the control unit 18 controls processing of the transceiving unit 11, the B-mode processing unit 12, the Doppler processing unit 13, the image generating unit 14, and the data processing unit 15 based on various kinds of setting requests input by an operator through the input device 3, or various kinds of control programs and data read from the internal storage unit 17. Furthermore, the control unit 18 performs control to display ultrasonic image data for display that is stored in the image memory 16 on the monitor 2.

As above, the entire configuration of the ultrasonography apparatus according to the first embodiment has been explained. With such a configuration, generation and display of ultrasonic image data (for example, B-mode image data) are performed.

Figure 2:
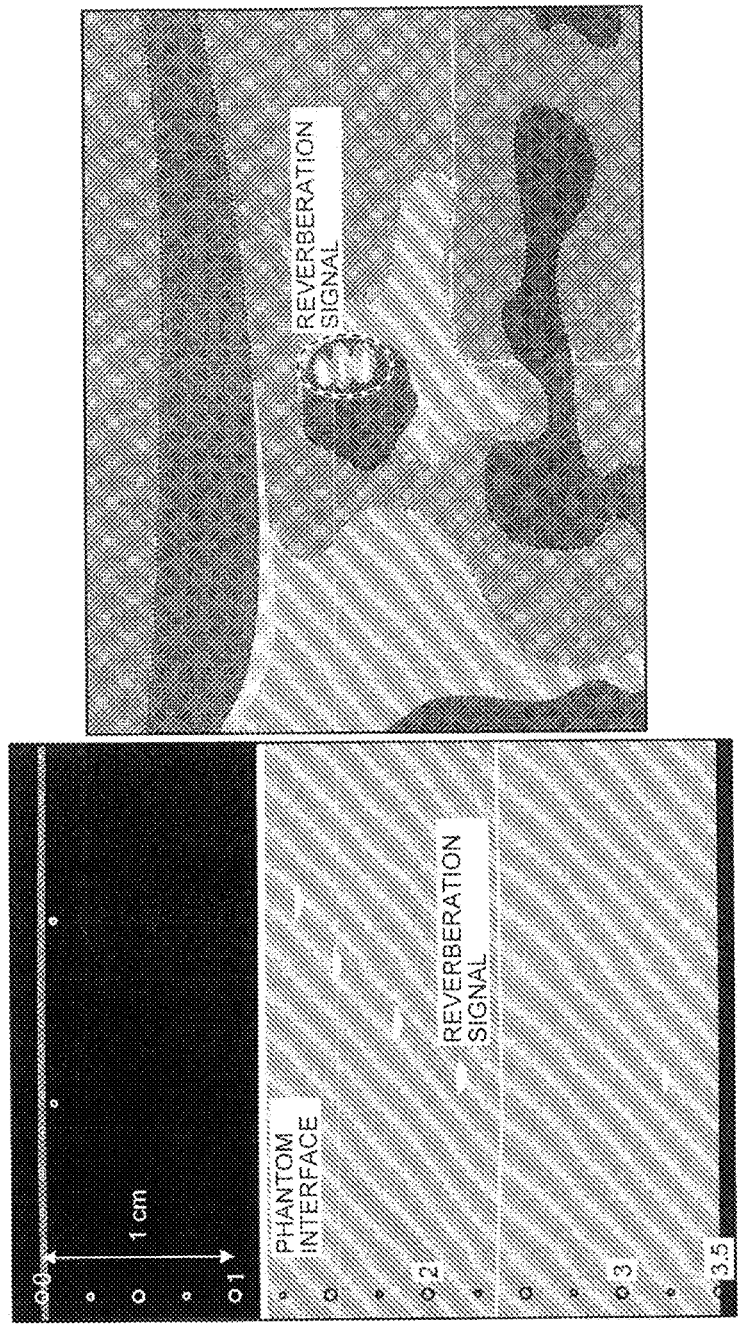
FIG. 2 is a diagram for explaining multiple reflection artifacts.

Conventionally, various methods have been applied to reduce noise signals (multiple reflection signals and side lobes, for example) of B-mode image data. Visualized noise signals degrade image quality and interfere with a diagnosis. In other words, a doctor who refers to a visualized noise signal may determine that some object is present on the position where the noise signal is drawn. FIG. 2 is a diagram for explaining multiple reflection artifacts. The left figure in FIG. 2 indicates B-mode image data that visualizes reflected signals from a phantom covered with water on a surface. In this image, a multiple reflection signal generated by a phantom interface located at a depth of approximately 1.1 centimeters (cm) is drawn at a depth of approximately 2.2 cm. The right figure in FIG. 2 illustrates B-mode image data that visualizes reflected signals from a human carotid artery. In this image, multiple reflection signals are present in a vascular lumen of the carotid artery.

For example, in order to reduce the multiple reflection signals exemplified in FIG. 2, what is called spatial compounding processing has been conventionally performed. FIG. 3, FIG. 4A, FIG. 4B, and FIG. 5 are diagrams for explaining conventional spatial compounding processing.

One example of methods for reducing multiple reflection signals by the compounding processing is a method in which a plurality of pieces of B-mode image data with various deflection angles in ultrasonic wave transmission/reception are compounded by signal averaging. A method is also known that applies the above described method, in which a degree and a position of a multiple reflection echo component are estimated from B-mode image data with various deflection angles, and weight at signal averaging is adaptively controlled from an estimation result. These methods are methods of compounding a plurality of pieces of ultrasonic image data with various deflection angles that are generated by ultrasonic scanning in which deflection angles in ultrasonic wave transmission/reception are varied among frames.

The deflection angle in a direction perpendicular to a direction of arrangement of the transducer elements is defined herein as "0 degrees". The deflection angle "0 degrees" is a direction of normal ultrasonic wave transmission/reception that is performed without deflection. Furthermore, a deflection angle in a leftward direction relative to the direction of arrangement of the transducer elements is defined as a "positive angle", and a deflection angle in a rightward direction relative to the direction of arrangement of the transducer elements is defined as a "negative angle".

Figure 3:
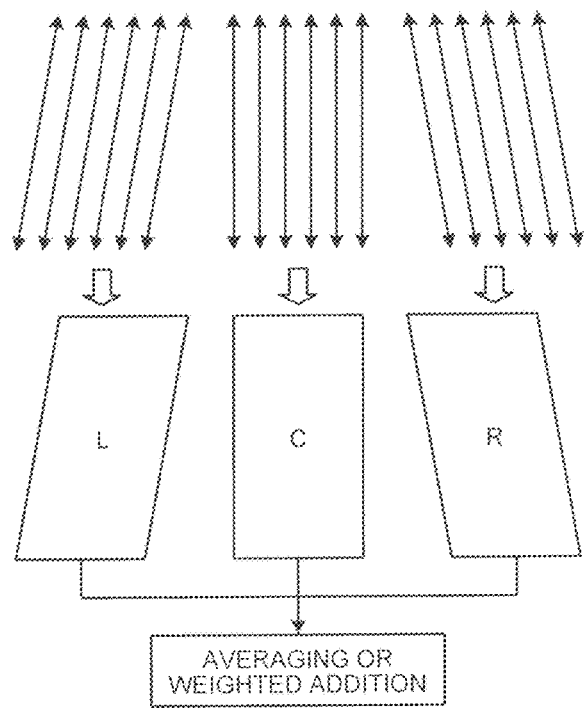
FIG. 3 is a diagram (1) for explaining conventional spatial compounding processing.

When the definition is applied, "C" illustrated in FIG. 3 is B-mode image data that is generated by performing ultrasonic wave transmission/reception with the deflection angle of "0 degrees". Moreover, "L" illustrated in FIG. 3 is B-mode image data that is generated by performing ultrasonic wave transmission/reception deflected leftward with the deflection angle of "+θ degrees". Furthermore, "R" illustrated in FIG. 3 is B-mode image data that is generated by performing ultrasonic wave transmission/reception deflected rightward with the deflection angle of "−θ degrees". Hereinafter, "L" illustrated in FIG. 3 is described as left-deflected image data L. Moreover, hereinafter, "R" illustrated in FIG. 3 is described as right-deflected image data R. Furthermore, hereinafter, "C" illustrated in FIG. 3 that is a center image between the left-deflected image data L and the right-deflected image data R is described as center image data C.

In the conventional method illustrated in FIG. 3, image data in which the center image data C, the left-deflected image data L, and the right-deflected image data R are subjected to signal averaging is output. Alternatively, in the conventional method illustrated in FIG. 3, a degree and a position of a multiple reflection echo component are estimated from the center image data C, the left-deflected image data L, and the right-deflected image data R. Furthermore, in the conventional method illustrated in FIG. 3, weight at signal averaging is calculated from an estimation result, and weighting addition is performed on the center image data C, the left-deflected image data L, and the right-deflected image data R, to output image data.

Figure 4A:
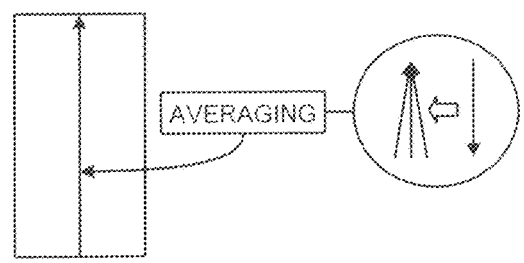
FIG. 4A and FIG. 4B are diagrams (2) for explaining conventional spatial compounding processing.
Figure 4B:
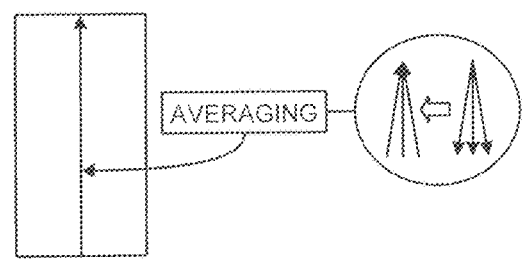

Moreover, two conventional methods exemplified in FIG. 4A and FIG. 4B are used as general spatial compounding processing to reduce multiple reflection echoes, other than the above "conventional method of compounding a plurality of images with various deflection angles". The method exemplified in FIG. 4A is a method in which signal averaging is performed on a plurality of reception signal groups with various reception deflection angles that are obtained simultaneously by parallel simultaneous reception for the same transmission beam when a reception signal of a single scan line is acquired. In the method exemplified in FIG. 4A, fixing the transmission aperture and the reception aperture, reflected waves with reception deflection angles (for example, 0 degrees, +θ degrees, and −θ degrees) in three directions are acquired by parallel simultaneous reception for a transmission ultrasonic wave at one scan line, thereby acquiring simultaneous reception signals in the three directions. In the conventional method illustrated in FIG. 4A, by signal averaging the simultaneous reception signals in the three directions, one reception signal with the reception deflection angle of "0 degrees" is acquired. The processing is performed for all of scan lines in a frame.

On the other hand, the method exemplified in FIG. 4B is a method in which reception signals from corresponding directions are acquired while varying the deflection angles of transmission among rates when a reception signal of a single scan line is acquired, and the reception signals at the rates are signal averaged. FIG. 4B indicates reception signals in three directions generated by performing ultrasonic wave transmission/reception with transmission/reception deflection angles (0 degrees, +θ degrees, and −θ degrees) in three directions, fixing the transmission aperture and the reception aperture. In the conventional method illustrated in FIG. 4B, by signal averaging the reception signals in the three directions, one reception signal with the reception deflection angle of "0 degrees" is acquired. The processing is performed for all of scan lines in a frame.

These three kinds of conventional methods are techniques that, by using the fact that a position at which a multiple reflection echo (noise) appears varies according to a deflection angle when the deflection angle of an ultrasonic beam to the subject P is changed (when the ultrasonic beam is inclined), improve a signal-to-noise ratio in an image by maintaining a signal component (for example, a signal component originated in a tissue) having relatively small intensity variation even if inclined, by compounding processing. For the change of the deflection angle at transmission, a control by transmission delay patterns is suitable. Moreover, as for the change of the deflection angle at reception, there is a case in which a control of changing the reception delay pattern is performed, and a case in which a control of unbalancing reception aperture distribution (apodization) on right and left is performed.

The conventional method exemplified in FIG. 4A is more in real time because parallel simultaneous reception is applied. However, because the deflection angles are varied between transmission and reception in the conventional method exemplified in FIG. 4A, to obtain multiple reflection reducing effect, it is necessary to make the deflection angle large. However, in the conventional method exemplified in FIG. 4A, if the deflection angles between transmission and reception are large, the sensitivity is degraded.

On the other hand, in the conventional method exemplified in FIG. 4B, the deflection angles can be the same between transmission and reception, and therefore, the deflection angle can be set large while suppressing degradation of the sensitivity, and the multiple reflection reducing effect higher than that in the conventional method exemplified in FIG. 4A can be obtained. However, the conventional method exemplified in FIG. 4B requires a rate sequence, and the frame rate decreases.

Figure 5:
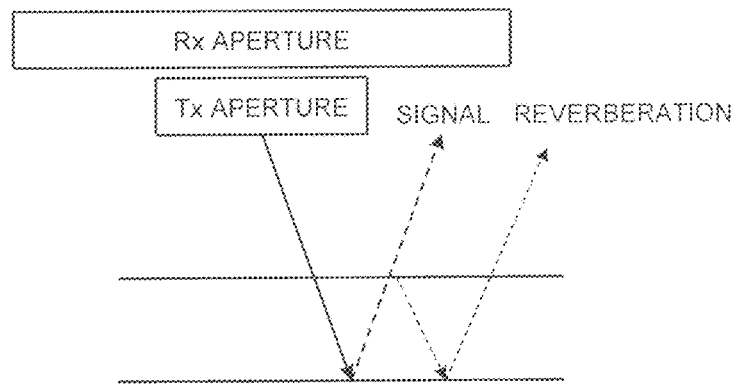
FIG. 5 is a diagram (3) for explaining conventional spatial compounding processing.

On the other hand, in the conventional method exemplified in FIG. 3, because the deflection angle is changed per frame (per image), the deflection angle between transmission and reception can be the same, thereby suppressing degradation of the sensitivity, and decrease of the frame rate is small. That is, when the deflection angle is change per frame, the transmission/reception deflection angle can be changed by the control of the transmission/reception delay pattern, fixing the reception aperture size (reception aperture width), and therefore, a relatively large deflection angle can be obtained while maintaining the sensitivity. If the deflection angle is large, for example, as illustrated in FIG. 5, among reflected waves of ultrasonic waves transmitted from the transmission aperture (Tx Aperture) in an inclined manner, while a true signal component (Signal) of single reflection is received by the reception aperture (Rx Aperture), a multiple reflection component (Multiple reflection) that repeats reflection is received outside the reception aperture (Rx Aperture). As described, in the method in which the deflection angle is change per frame, by making the deflection angle large, the multiple reflection reducing effect is enhanced. Therefore, in the conventional method exemplified in FIG. 3, it is possible to achieve both the multiple reflection reducing effect and maintenance of the frame rate and the sensitivity to some extent.

However, in the method in which the deflection angle is changed per frame, the influence of reduced amplitude when a deflection angle is increased cannot be avoided due to the constraint of element factors. Particularly, at a transducer element at an end portion of the aperture, transmission and reception are performed at relatively large deflection angles, and therefore, the degree of reduction of amplitude is large. This corresponds to reduction in an effective aperture width. That is, in deflected image data (for example, the left-deflected image data L and the right-deflected image data R), the lateral resolution is degraded compared to that of image data with the deflection angle of "0 degrees" (the center image data C). Furthermore, in the deflected image, the sensitivity (signal-to-noise (S/N) ratio) to the center image data C is also degraded. Therefore, in an output image that is obtained by compounding a plurality of images with various deflection angles, the lateral resolution and the sensitivity are degraded compared to those of the image not deflected (for example, the center image data C).

Moreover, these days, a method of effectively reducing specular multiple reflection by reception apodization has been developed other than the spatial compounding method explained using FIG. 3 through FIG. 5. The reception apodization is one of parameters used in reception beam forming. The reception apodization is performed by using a pattern in accordance with a purpose as the weighting pattern of the aperture function described above. In this developed method, reception apodization is performed to remove multiple reflection components as much as possible. An aperture function used in this developed method of reception apodization is explained using FIG. 6 through FIG. 9, together with an aperture function used in a conventional reception apodization. FIG. 6 through FIG. 9 are diagrams for explaining aperture functions.

Figure 6:
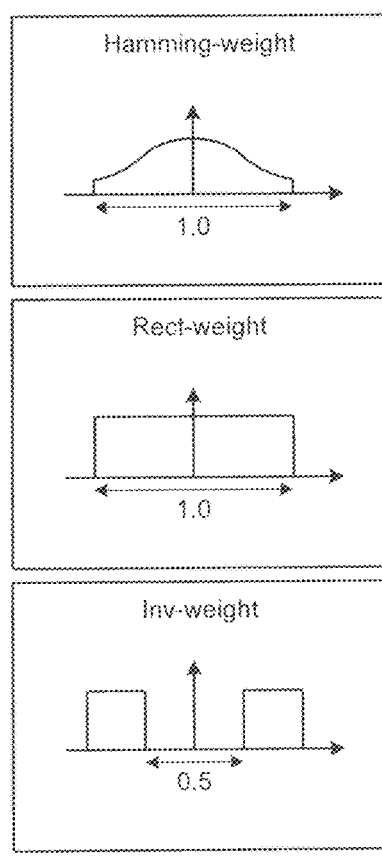
FIG. 6 is a diagram (1) for explaining aperture functions.

In the conventional reception apodization, to acquire the main lobe of a signal component, for example, an aperture function to weight by a "hamming window" is used (refer to "Hamming-weight" in the upper diagram in FIG. 6). Alternatively, in the conventional reception apodization, to acquire a signal component with high frequency resolution, for example, an aperture function to weight by a "rectangular window" is used (refer to "Rect-weight" in the middle diagram in FIG. 6). In FIG. 6, a reception aperture width is indicated as "1.0".

Furthermore, in the above developed method, for the purpose of removing multiple reflection components, an aperture function that makes a weight of a center portion of the reception aperture substantially "0" is used. For example, in this developed method, an aperture function in which a half (0.5) of the reception aperture width has a weight of "0" at an aperture center portion is used as indicated in "Inv-weight" in the lower diagram in FIG. 6.

As illustrated in FIG. 6, the aperture function using the hamming window is an aperture function having a weighting pattern in which a weight of a transducer element in the center portion of the reception aperture is larger than a weight of a transducer element at an end portion of the reception aperture. The aperture function using the rectangular window is one example of an aperture function in which a weight of a transducer element at an end portion of the reception aperture is larger than that in the weighting pattern of the aperture function using the hamming window.

On the other hand, as illustrated in FIG. 6, the aperture function of "Inv-weight" is an aperture function in which a weight of a transducer element in the center portion of the reception aperture is smaller than a weight of a transducer element at an end portion of the reception aperture. In the following, based on the difference in a form of weighting patterns, the conventional reception apodization may be described as "normal apodization", and the developed reception apodization such as the above may be described as "inverse apodization". Moreover, in the following, the aperture function used in the "normal apodization" may be described as a "normal aperture function", and the aperture function used in the "inverse apodization" may be described as an "inverse aperture function".

Figure 7:
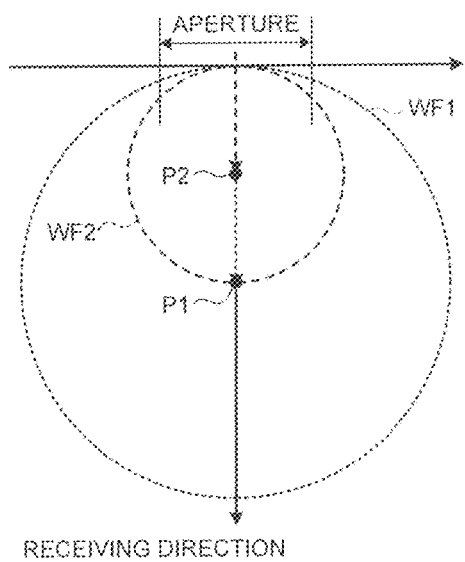
FIG. 7 is a diagram (2) for explaining aperture functions.

The fact that the inverse aperture function used in the above developed method is effective for reducing multiple reflection is explained using FIG. 7. "Aperture" illustrated in FIG. 7 is the reception aperture. In FIG. 7, the width of the reception aperture is indicated by a bidirectional arrow. FIG. 7 indicates positional relation between the reception aperture and a scan line direction (refer to "Receiving direction" in the figure) when a reflected wave is received from a reflection source that is positioned right under (in front of) the reception aperture in linear scanning or sector scanning. Furthermore, P1 illustrated in FIG. 7 is a reflection source positioned in the scan line direction, and P2 illustrated in FIG. 7 is a reflection source positioned closer to the reception aperture than the reflection source P1. In FIG. 7, a distance between the reflection source P1 and the reception aperture is twice as large as a distance between the reflection source P2 and the reception aperture.

It is supposed that a reflected wave that has been reflected on the reflection source P2 is reflected once on a surface of the ultrasound probe 1 to re-enter a living body, and the re-entered reflected wave is reflected on the reflection source P2 to be received as a reflected wave signal. A wavefront of the reflected wave reflected from the reflection source P2 in this single multiple reflection is observed as a wavefront of a reflected wave that is reflected on the reflection source P1. In FIG. 7, a signal wavefront from the normal reflection source P2 is indicated by "WF2", and a multiple reflection wavefront from the reflection source P1 of the single multiple reflection is indicated by "WF1".

By reception delay processing using a position near the reflection source P2 as a reception focus, for the signal wavefront WF2, phases match at all of the transducer elements structuring the reception aperture. On the other hand, due to the difference between the depth in which a signal component from front is finally reflected and the depth in which a multiple reflection component from front is finally reflected, even if the reception delay processing using a position near the reflection source P2 as a reception focus is performed, for the multiple reflection wavefront WF1, phases match only at transducer elements in a limited range in the center portion of the reception aperture. The inverse apodization is a method of reducing multiple reflection components using such a phenomenon, for example, by making a multiple reflection component entering the center portion of the reception aperture "0" by applying the inverse aperture function (the inverse aperture function in which the center portion is zero) indicated in the lower diagram in FIG. 6.

Figure 8:
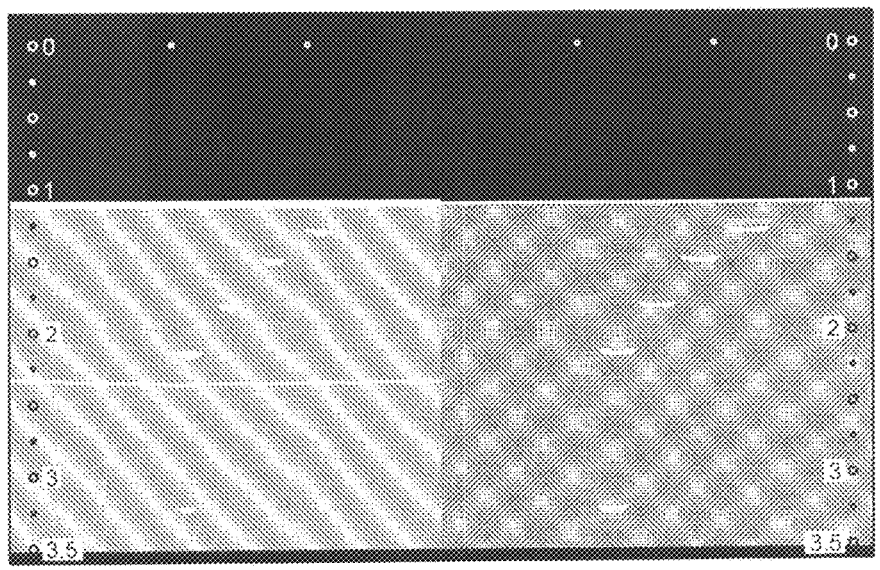
FIG. 8 is a diagram (3) for explaining aperture functions.

However, in the inverse apodization, although multiple reflection components can be reduced, a side lobe component (particularly, a 1st side-lobe component) is high and the lateral resolution is degraded compared to the case of normal apodization, causing degradation of image quality. The left figure in FIG. 8 illustrates B-mode image data that visualizes reflected signals from a phantom using the normal aperture function of the hamming window. The right figure in FIG. 8 illustrates B-mode image data that visualizes reflected signals from a phantom using the inverse aperture function in which the center portion is zero. As illustrated in FIG. 8, although the B-mode image data using the normal aperture function of the hamming window has higher lateral resolution, a multiple reflection signal generated by a phantom interface located at a depth of approximately 1.1 cm is drawn at a depth of approximately 2.2 cm. On the other hand, as illustrated in FIG. 8, for the B-mode image data using the inverse aperture function in which the center portion is zero, a multiple reflection signal occurring at a depth of approximately 2.2 cm is reduced but lateral resolution is degraded.

Figure 9:
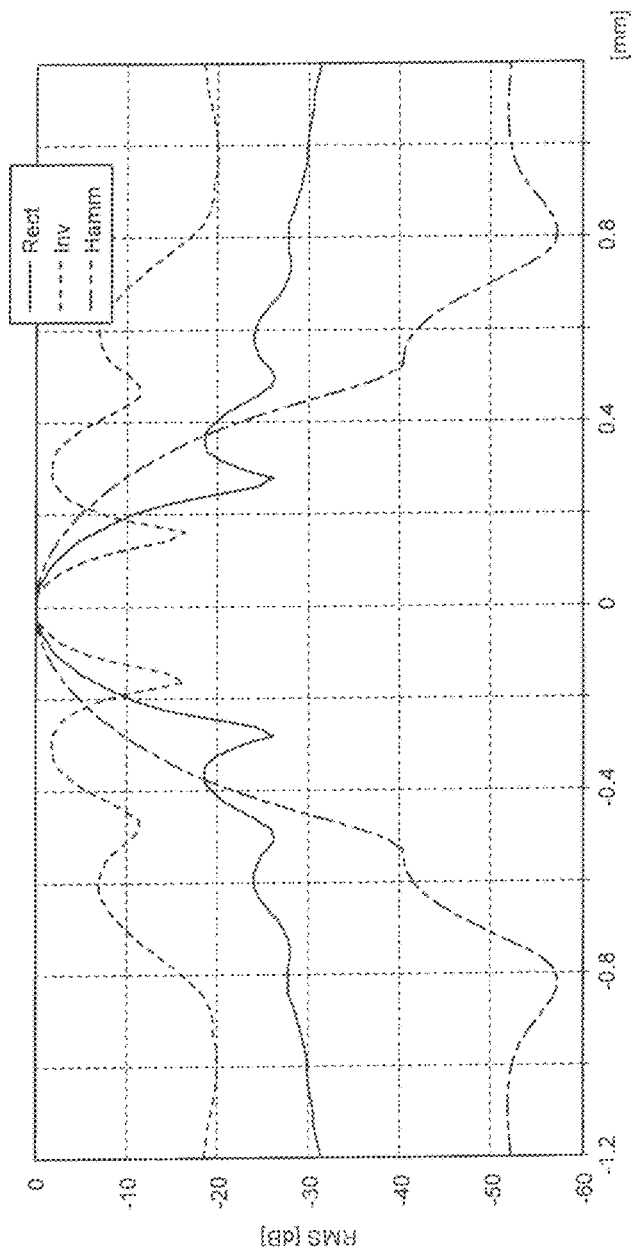
FIG. 9 is a diagram (4) for explaining aperture functions.

This is explained using FIG. 9. FIG. 9 indicates a result of calculation of a sound field distribution (received sound-field distribution) near a focus that is acquired by the three aperture functions illustrated in FIG. 6. The horizontal axis in FIG. 9 indicates a position in a lateral direction (unit: millimeter (mm)), and the vertical axis in FIG. 9 indicates a root mean square (RMS, unit: decibel (dB)) of a sound field near a focus. It has been known that the sound field distribution near a focus is given by the Fourier transform of the aperture function. For example, the Fourier transform of the rectangular function is a sinc function.

As illustrated in FIG. 9, when a sound field distribution of the normal aperture function of the hamming window and a sound field distribution of the normal aperture function of the rectangular window are compared, in the normal aperture function of the hamming window, although the width of the main lobe component in the lateral direction is wide, the main lobe component of high intensity is obtained and the side lobe component can be maintained low. On the other hand, as illustrated in FIG. 9, with the inverse aperture function in which the center portion is zero, the intensity of the main lobe component is lower than that of the normal aperture function of the rectangular window, and the intensity ratio of the side lobe component to the main lobe component is higher than that of the normal aperture function of the rectangular window. The sound field distribution in FIG. 9 indicates how a point being a reflection source is drawn in an image. FIG. 9 indicates that the lateral resolution of B-mode image data that is obtained by the inverse apodization using the inverse aperture function in which the center portion is zero is lower than that in the normal apodization.

To ease degradation of the image quality in the inverse apodization, aperture compounding processing in which the normal apodization and the inverse apodization are combined can also be performed. However, in the aperture compounding processing with a reception signal acquired by the normal aperture function and a reception signal acquired by the inverse aperture function, the lateral resolution of an image after compounding is degraded by the influence of the side lobe component (particularly, the 1st side-lobe component) that becomes high in the inverse apodization. Moreover, the position of the 1st side-lobe component that is generated in the inverse apodization corresponds to the position of the main lobe component in the normal apodization as illustrated in FIG. 9, and therefore, a moire (striped pattern) can be created in an image by phase interference of the both. Furthermore, in general transmission/reception sound-field generation, side lobe components are suppressed by narrowing a relatively wide transmission beam with a narrow reception beam. However, in the inverse apodization, as illustrated in FIG. 9, not only the 1st side-lobe component but also a 2nd side-lobe component and the like are also high. From this fact, if a wide transmission beam is used, a side lobe component in the inverse apodization becomes higher compared to a case in the normal apodization. As a result, when the general transmission/reception sound-field generation in which a wide transmission beam is narrowed by a narrow reception beam is performed, in an image after the aperture compounding, these surrounding noises are folded in, and the image quality tends to be degraded.

As described above, in the processing in which spatial compounding processing or inverse reception apodization processing is performed for the purpose of reducing multiple reflection signals, enhancing a multiple reflection signal reducing effect incurs a trade-off such as removing inherent reflected signals, degrading image resolution, or impairing real-time generation and display of images, which is an advantage of ultrasonography apparatuses. A method is also known in which side lobes are reduced by obtaining a correlation coefficient between an RF signal acquired using the aperture function of the hamming window and an RF signal acquired using the aperture function of the rectangular window, for example. In such a method, however, it is difficult to enhance real-time performance because addition processing for a certain section using RF signals is needed for each point, which involves large amount of calculation.

From these facts, development has been conventionally desired for an ultrasonic imaging method that does not incur the above described trade-offs, or an ultrasonic imaging method that performs processing on an image acquired by processing involving the trade-offs so as to acquire the image without the trade-offs.

The spatial compounding processing, which is most frequently used these days for reducing noise, is a method that, for example, deflects an ultrasonic wave to acquire a plurality of signal groups, and compounds the signal groups by addition processing that is linear processing, thereby improving image quality.

However, as explained using FIG. 4A and FIG. 4B, for example, performing the addition processing by the spatial compounding at the stage of IQ signals changes a speckle pattern due to phase interference. This change may interfere with diagnosis for a part, such as a liver, for which speckles are used as a basis of the diagnosis. As explained using FIG. 3, for example, performing the addition processing at the stage of amplitude values provides an absolute value, thereby losing phase information. The lack of the phase information makes other processing than filtering by image processing (such as the raw filtering described above) difficult to be performed as later-stage processing after the spatial compounding, which narrows an application range.

The following describes reasons for the difficulty in obtaining an image without the trade-offs from a signal obtained by compounding processing (addition processing) used in a conventional spatial compounding method.

For example, two output signals (IQ signals) "$IQ_1$" and "$IQ_2$" obtained by two processing with different conditions are expressed by Equation 1 below.

$$IQ_1 = A \cdot \exp(-j\theta_1) = A_i + jA_q \brace IQ_2 = B \cdot \exp(-j\theta_2) = B_i + jB_q} \quad (1)$$

"j" presented in Equation 1 is an imaginary number, "A" and "B" presented in Equation 1 are the amplitudes of "$IQ_1$" and "$IQ_2$", respectively, and "$\theta_1$" and "$\theta_2$" presented in Equation 1 are the phases of "IV" and "$IQ_2$", respectively. "$A_i$" and "$A_q$" presented in Equation 1 are the real part and the imaginary part of "$IQ_1$", respectively, and "$B_i$" and "$B_q$" presented in Equation 1 are the real part and the imaginary part of "$IQ_2$", respectively.

A signal "$IQ_{compound}$" obtained by compounding "A" and "B" presented in Equation 1 by the addition processing "$IQ_1+IQ_2$" of the spatial compounding at the stage of complex numbers, that is, the stage of IQ signals, is expressed by Equation 2 below.

$$IQ_{compound}=IQ_1+IQ_2=(A_i+B_i)+j(A_q+B_q) \quad (2)$$

The phase of the signal "$IQ_{compound}$" after the spatial compounding is expressed by Equation 3 below.

$$\theta_{IQ_{compound}} = \tan^{-1}\frac{A_i + B_i}{A_q + B_q} \quad (3)$$

Performing the spatial compounding by the addition processing at the stage of IQ signals changes the phase term, and thus can change a speckle domain in image data in particular. Specifically, adding signals with low correlation can provide an effect of speckle reduction. However, the change in speckle reduction may change a speckle pattern due to phase interference caused by compounding in some cases, and may interfere with diagnosis for a part, such as a liver, for which speckles are used as a basis of the diagnosis.

When the spatial compounding (for example, the spatial compounding in FIG. 3) is performed after absolute values of the IQ signals are obtained and converted to amplitude values (amplitude signals) by logarithmic conversion, "$Amp_{compound}$" expressed by Equation 5 below is output by adding the amplitude values of "$IQ_1$" and "$IQ_2$" expressed by Equation 4 below.

$$Amp_{IQ_1} = 10\log_{10}(A_i^2 + A_q^2) \brace Amp_{IQ_2} = 10\log_{10}(B_i^2 + B_q^2)} \quad (4)$$

$$Amp_{compound} = Amp_{IQ_1} + Amp_{IQ_2} = 10\log_{10}(A_i^2 + A_q^2)(B_i^2 + B_q^2) \quad (5)$$

The spatial compounding of amplitude values is a method for improving image quality similarly to the spatial compounding of IQ signals. The spatial compounding of amplitude values, however, provides absolute values at a stage before the compounding, and thus loses phase information and obtains only amplitude information. That is, the spatial compounding of amplitude values is a compounding method for a stage without phase information, and therefore does not incur phase interference due to compounding by addition such as in the case of the spatial compounding of IQ signals. Thus, image data to which an image interpreter has no sense of incompatibility can be obtained compared to the case of the spatial compounding of IQ signals. However, if image quality of image data obtained by the compounding by addition is still low and some kind of processing is needed at a later stage after the spatial compounding of amplitude values, signal processing using phase information such as complex filtering or inverse filtering cannot be performed on complex signals because only amplitude information is present. In other words, executable processing at a later stage after the spatial compounding of amplitude values is limited to image processing using amplitude information.

Therefore, the ultrasonography apparatus according to the first embodiment performs processing by the data processing unit 15 and the control unit 18 illustrated in FIG. 1 in order to ensure improvement in image quality of image data obtained by signal compounding.

First, the acquiring unit 151 according to the first embodiment acquires a plurality of IQ signals output by a plurality of processing with different conditions. Specifically, the acquiring unit 151 acquires a plurality of IQ signals obtained by performing a plurality of processing with different conditions on reflected wave signals generated at a transducer element included in an ultrasound probe. The compounding unit 152 according to the first embodiment generates a compound signal compounded by non-linear processing of the IQ signals. Specifically, the compounding unit 152 generates a compound signal from the IQ signals by performing multiplication processing among the IQ signals as non-linear processing. More specifically, the compounding unit 152 generates a compound signal from the IQ signals by calculating the numerator term defined by a complex correlation as non-linear processing. The control unit 18 then causes at least the monitor 2 to display image data based on the compound signal.

The following describes a compounding method using non-linear processing performed by the compounding unit 152 by assuming that IQ signals acquired by the acquiring unit 151 are two IQ signals output by two different processing. As one example of the non-linear processing, the compounding unit 152 compounds "$IQ_1$" and "$IQ_2$" expressed by Equation 1 by the multiplication processing expressed by Equation 6 to output a compound signal "IQ". Equation 6 indicates that the compound signal "IQ" of "$IQ_1$" and "$IQ_2$" is obtained by multiplying "$IQ_1$" by a complex conjugate "$IQ_2^*$" of "$IQ_2$". "$IQ_1 \cdot IQ_2^*$" is the numerator term (numerator) of the complex correlation when "$IQ_1$" and "$IQ_2$" are not ensemble averaged.

$$IQ = IQ_1 \cdot IQ_2^* = A \cdot B \exp[-j(\theta_1 - \theta_2)] = (A_i B_i + A_q B_q) - j(A_q B_i - A_i B_q) \quad (6)$$

"$IQ_{compound}$" in Equation 2, which is compounded by adding the two IQ signals, can be expressed as the product of the amplitude term and the phase term as expressed by Equation 7 below. "$Amp_{compound}$" in Equation 5, which is compounded by adding the amplitude values of the two IQ signals, can be expressed as an equation with only the amplitude term as expressed by Equation 8 below. "IQ" in Equation 6, which is compounded by multiplying the two IQ signals, can be expressed as the product of the amplitude term and the phase term as expressed by Equation 9 below.

$$IQ_{compound} = \underbrace{\sqrt{(A_i + B_i)^2 + (A_q + B_q)^2}}_{\text{Amplitude term}} \exp\left(\tan^{-1}\frac{A_i + B_i}{A_q + B_q}\right) \quad (7)$$

$$Amp_{compound} = \underbrace{\sqrt{(A_i^2 + A_q^2)(B_i^2 + B_q^2)}}_{\text{Amplitude term}} \quad (8)$$

$$IQ = \underbrace{\sqrt{(A_i^2 + A_q^2)(B_i^2 + B_q^2)}}_{\text{Amplitude term}} \underbrace{\exp(\theta_1 - \theta_2)}_{\text{Phase term}} \quad (9)$$

The amplitude term in Equation 9, that is, the amplitude term of the compound signal after the multiplication processing as one example of non-linear compounding processing by the compounding unit 152, is expressed by the same equation as that of conventional spatial compounding of amplitude values. In other words, amplitude resulted from Equation 9 is equivalent to that of the spatial compounding of amplitude values expressed in Equation 8. An amplitude "$Amp_{IQ}$" obtained by Equation 9 is expressed by Equation 10 below.

$$\begin{aligned} Amp_{IQ} &= 20\log_{10}[(A_i B_i + A_q B_q)^2 + (A_q B_i - A_i B_q)^2] \\ &= 20\log_{10}[(A_i B_i)^2 + (A_q B_q)^2 + (A_q B_i)^2 + (A_i B_q)^2] \\ &= 20\log_{10}[A_i^2(B_i^2 + B_q^2) + A_q^2(B_i^2 + B_q^2)] \\ &= 20\log_{10}[(A_i^2 + A_q^2)(B_i^2 + B_q^2)] \end{aligned} \quad (10)$$

The phase term in Equation 9 differs between before and after the compounding in the same manner as the spatial compounding at the stage of IQ signals. However, as described above, the amplitude of the compound signal after the multiplication processing is equivalent to the result of the spatial compounding of the amplitude values. For this reason, even if the phase term changes, an image that causes no sense of incompatibility in a speckle domain can be obtained from the compound signal generated by the compounding unit 152.

A major difference between the compound signal after the multiplication processing and the result of the spatial compounding of the amplitude values is that, as expressed by Equation 9, the compound signal after the multiplication processing includes phase information at a stage after the compounding similarly to the case of IQ signals. The phase term of the compound signal includes phase information "$\theta_{IQ}$" expressed by Equation 11.

$$\theta_{IQ} = \theta_1 - \theta_2 \quad (11)$$

The phase information "$\theta_{IQ}$" is "$\theta_1 - \theta_2$" as expressed by Equation 11. "$\theta_1 - \theta_2$" is the phase difference between the IQ signals output by the two different processing. This phase difference means that the phase information "$\theta_{IQ}$" differs from the phase information included in "$IQ_{compound}$" and is a significant index.

In other words, a compound signal obtained by performing compounding using the non-linear processing as described above (multiplication processing by a complex conjugate) is a complex signal including phase information such as the phase difference between IQ signals. Accordingly, in the first embodiment, "signal processing using a spatial complex filter and phase information", which cannot be applied in conventional compounding processing that performs compounding by addition, can be performed on a compound signal output by the compounding unit 152.

As illustrated in FIG. 1, the data processing unit 15 includes the signal processing unit 153 having a function that performs signal processing on the complex signal. The signal processing unit 153 can detect a phase difference between two IQ signals to be compounded. By using the phase difference, the correlation between the two signals to be compounded can be utilized. The signal processing unit 153 can also perform spatial complex filtering as signal processing. For example, the signal processing unit 153 can perform complex filtering that eliminates noise signals by smoothing. In the case described above, a phase changes by a complex filter, and thus the complex filtering is preferably performed after processing that uses phase information. In another case, the signal processing unit 153 performs, for example, inverse filtering that restores deteriorated signals using convolution such as "Wiener Filter".

For example, the signal processing unit 153 performs signal processing on a compound signal. In such a case, the control unit 18 causes at least the monitor 2 to display image data generated from the compound signal subjected to the signal processing.

Alternatively, the following processing may be performed on the precondition that signal processing is performed on a compound signal. That is, the signal processing unit 153 performs signal processing (pre-compounding signal processing) on each of a plurality of IQ signals acquired by the acquiring unit 151. In such a case, the compounding unit 152 compounds, using non-linear processing, the IQ signals subjected to the signal processing and outputs the signal as a compound signal to the signal processing unit 153. The signal processing unit 153 performs signal processing (post-compounding signal processing) on the compound signal. The control unit 18 then causes at least the monitor 2 to display image data generated from the compound signal subjected to the signal processing (post-compounding signal processing).

Figure 10:
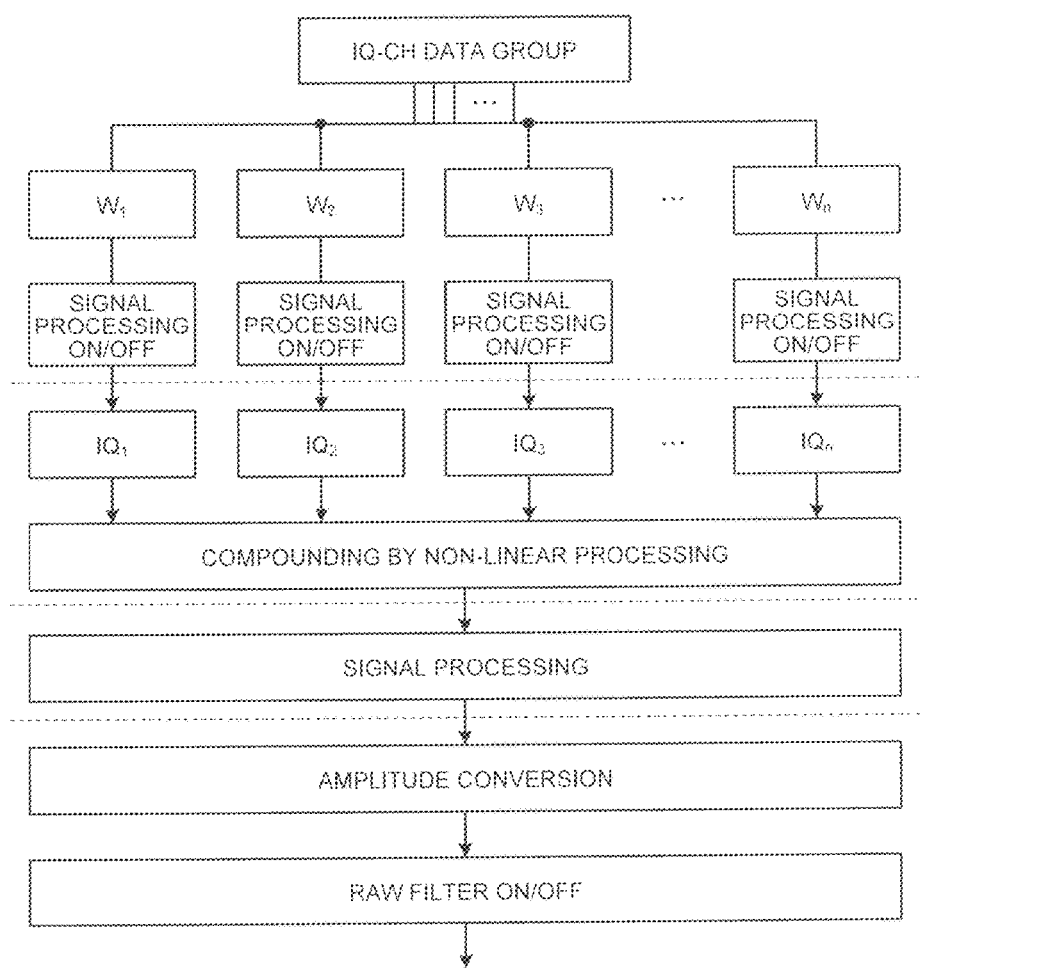
FIG. 10 is a diagram for explaining an outline of processing performed in the first embodiment.

FIG. 10 is a diagram for explaining an outline of the processing performed in the first embodiment. First, by the control of the control unit 18, the transceiving unit 11 performs ultrasonic wave transmission/reception at each scan line forming a scanning range. At this time, by the control of the control unit 18, various processing with different conditions are performed on an "IQ-CH data group" acquired by the ultrasonic wave transmission/reception. "$W_1, W_2, W_3, \ldots, W_n$" illustrated in FIG. 10 indicate that "n" types of processing are performed and the acquiring unit 151 acquires a data string of "n" number of IQ signals at a scan line.

Turning "On" or "Off" of the signal processing (pre-compounding signal processing) on the data string of "n" number of IQ signals can be set by an operator arbitrarily, for example. When the pre-compounding signal processing is performed, the operator specifies, for example, inverse filtering as the signal processing on each of the IQ signals.

Regardless of "On" or "Off" of the pre-compounding processing, a data string of "n" number of IQ signals "$IQ_1, IQ_2, IQ_3, \ldots, IQ_n$" are input to the compounding unit 152 as illustrated in FIG. 10, and the compounding unit 152 performs compounding by non-linear processing on "$IQ_1, IQ_2, IQ_2, \ldots, IQ_n$". This processing inputs a compound signal of each scan line to the signal processing unit 153. The signal processing unit 153 performs signal processing on the compound signal of each scan line as illustrated in FIG. 10. In the first embodiment, for example, the signal processing unit 153 can perform smoothing by performing spatial complex filtering on a compound signal in a region specified by an operator as the post-compounding signal processing. A speckle domain where scattered signals are acquired has large phase distribution, and thus performing smoothing by a complex filter on a compound signal having the same characteristics as that of IQ signals can provide an effect of speckle reduction. The compound signal (compound signal after the post-compounding signal processing) of each scan line output by the signal processing unit 153 is, as illustrated in FIG. 10, subjected to amplitude conversion by the B-mode processing unit 12, and then, with raw filtering (On) by the image generating unit 14 or without the raw filtering (Off) by the image generating unit 14, transmitted as image data (B-mode image data) for display. The image data is output to the monitor 2. Performing only spatial raw filtering used for image processing on the output data of the B-mode processing unit 12 without the post-compounding signal processing by the signal processing unit 153 can provide an effect of smoothing but not the effect of speckle reduction. Accordingly, image quality of the image data acquired based on the concept illustrated in FIG. 10 is improved by a synergistic effect of the effects of speckle reduction and smoothing, compared to conventional spatial compounding processing, for example.

When the acquiring unit 151 acquires three IQ signals ($IQ_1, IQ_2, IQ_3$) output by three processing, the compounding unit 152 performs the following compounding processing as one example. For example, the compounding unit 152 generates a compound signal by multiplying "$IQ_1 \cdot IQ_2^*$" by the complex conjugate of "$IQ_2 \cdot IQ_3^*$". Alternatively, the compounding unit 152 generates a compound signal by multiplying "$IQ_1 \cdot IQ_2^*$" by "$IQ_3^*$". The above processing is merely an example. The compounding unit 152 can perform compounding processing using any method as long as it is non-linear processing that provides phase information reflecting the phase information of a plurality of IQ signals that are compounding-sources.

The processing "$W_1, W_2, W_3, \ldots, W_n$" with different conditions illustrated in FIG. 10 are explained in detail in the section of a second embodiment and the following sections.

As described above, in the first embodiment, a group of IQ signals of each scan line obtained by various processing are compounded by non-linear processing, thereby outputting a compound signal including phase information that is useful for performing complex signal processing. As a result, in the first embodiment, various complex signals processing such as complex filtering and inverse filtering can be performed on the resultant compound signal, enabling improvement in image quality. Therefore, the first embodiment can ensure improvement in image quality of image data obtained by signal compounding.

Second Embodiment

Figure 11:
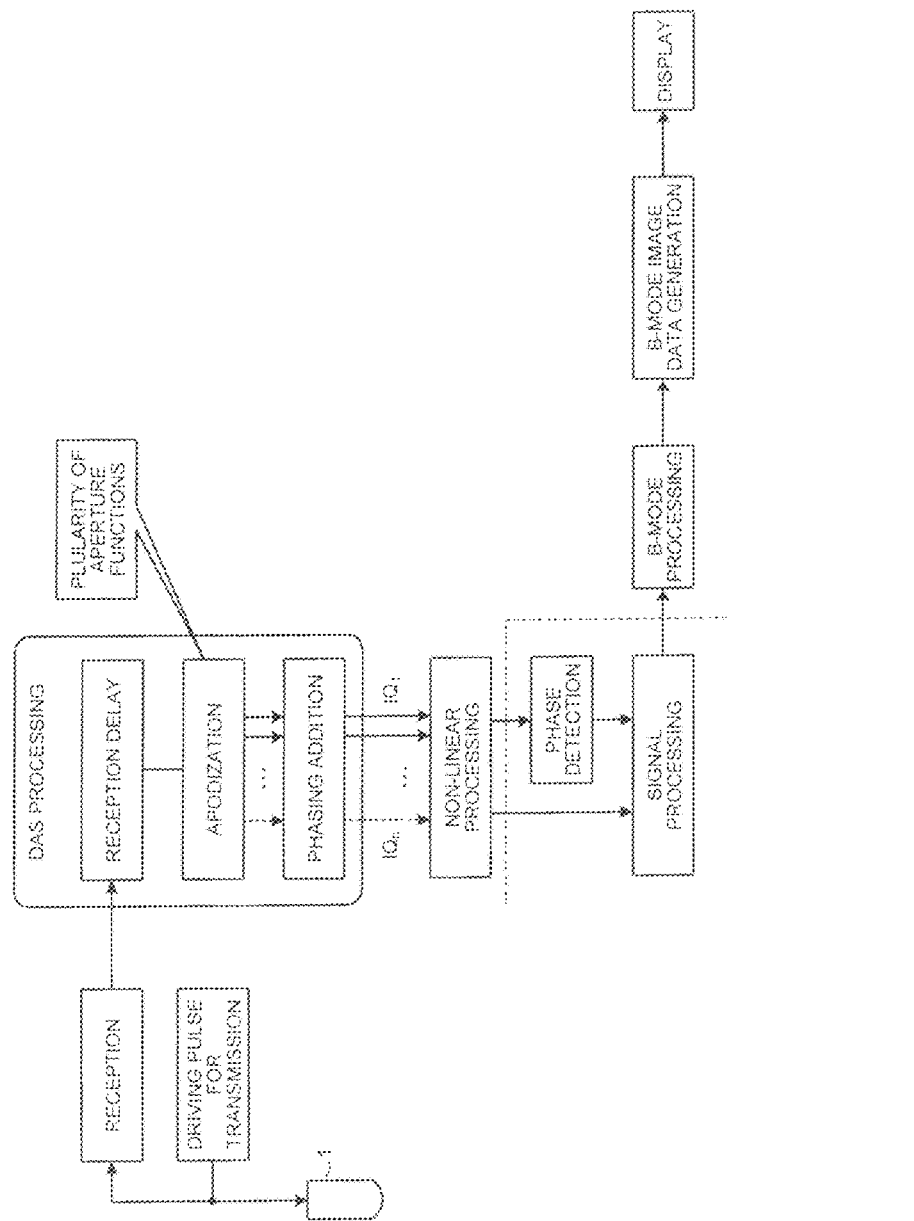
FIG. 11 is a diagram (1) for explaining a second embodiment.
Figure 12:
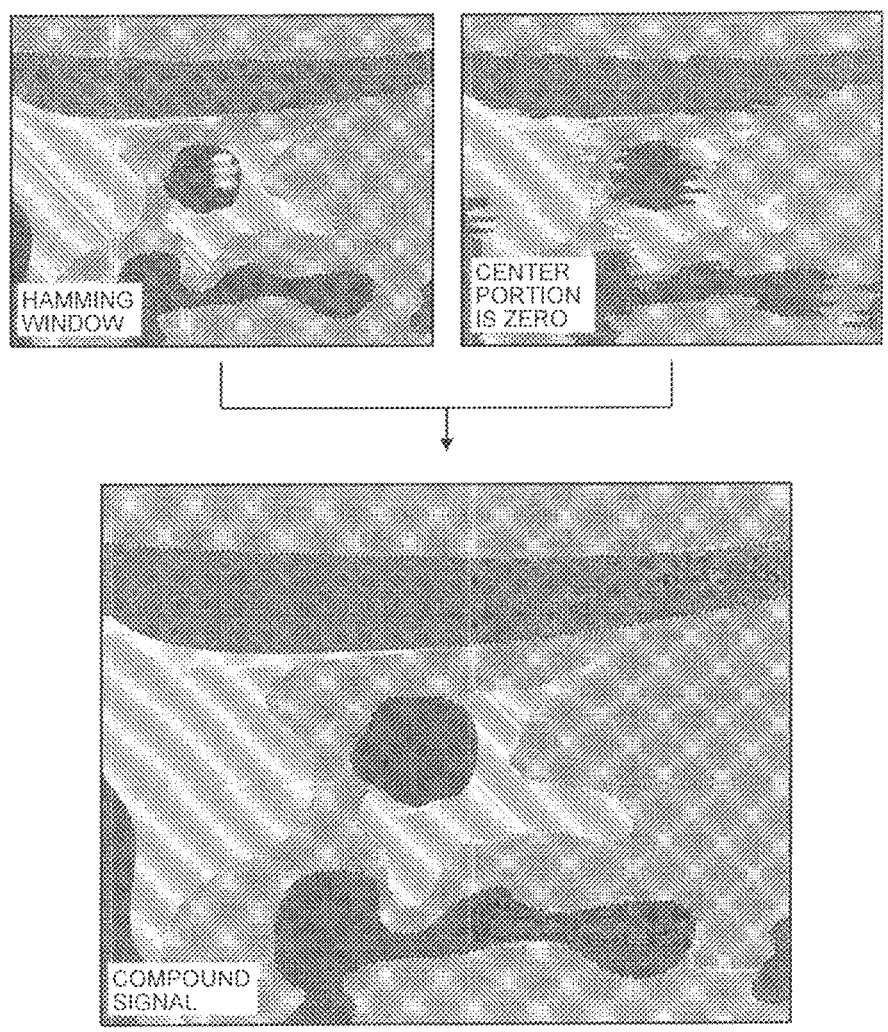
FIG. 12 is a diagram (2) for explaining the second embodiment.

In the second embodiment, a case is explained in which the "plurality of processing" explained in the first embodiment are "parallel processing of reception beam forming in a plurality of systems" that are performed by using a plurality of various parameters for at least one parameter in a parameter group used for the reception beam forming. FIG. 11 and FIG. 12 are diagrams for explaining the second embodiment.

Specifically, in the second embodiment, the "parallel processing of reception beam forming in a plurality of systems" is performed by using a plurality of aperture functions having different weighting patterns as aperture functions used for apodization (reception apodization) as illustrated in FIG. 11.

First, in the second embodiment, a plurality of IQ signals are output for each scan line based on a plurality of different aperture functions. Specifically, in the second embodiment, the aperture functions include at least one of the above described normal aperture function and inverse aperture function. In the following description, both of the normal aperture function and the inverse aperture function are used as the different aperture functions.

The normal aperture function is an aperture function to acquire a signal component. The "aperture function of the hamming window" is conceptually one example of the normal aperture function in which a weight of a range including a reception position at which a signal component is received at a reception aperture is larger than a weight of the outside of the range. For example, when a "boundary formed with objects causing multiple reflection and a probe surface are parallel", and a "direction of ultrasonic wave transmission/reception is perpendicular to the probe surface", a "reception position at which a signal component is received" is a "position in the center of the reception aperture". When a "reception position at which a signal component is received" is fixed to the center of the reception aperture, the normal aperture function is an aperture function in which a weight of a transducer element in the center portion is larger than a weight of a transducer element at an end portion of the reception aperture. The "aperture function of the hamming window" is one example of the normal aperture function for which the "reception position at which a signal component is received" is fixed to the "position in the center of the reception aperture".

The "aperture function of the rectangular window" is a normal aperture function in which weights of respective transducer elements at the reception aperture are uniform, and is one example of an aperture function having a weighting pattern in which a weight of a transducer element at an end portion is larger than that in the weighting pattern of the "aperture function of the hamming window". Alternatively, the normal aperture function applicable to the second embodiment may be the "aperture function of the hanning window" or an "aperture function of a flat-top window".

Moreover, the inverse aperture function is an aperture function to reduce multiple reflection components. The inverse aperture function is an aperture function in which a weight of a "range including a reception position at which a multiple reflection component is received at the reception aperture" is smaller than a weight of the outside of the range. By using the inverse function that is designed based on such a concept, a reception signal in which information of a signal received in the range of the reception aperture is reduced less than that of a signal received outside the range can be output as a reception signal of the reception aperture.

For example, when a "boundary formed with objects causing multiple reflection and a probe surface are parallel", and a "direction of ultrasonic wave transmission/reception is perpendicular to the probe surface", a "reception position at which a multiple reflection component is received" is a "position in the center of the reception aperture". When the "reception position at which a multiple reflection component is received" is fixed to the center of the reception aperture, the inverse aperture function is an aperture function in which a weight of a transducer element in the center portion is smaller than a weight of a transducer element at an end portion of the reception aperture. The "inverse aperture function in which the center portion is zero" described above is one example of a "center-fixed inverse aperture-function" for which the reception position is fixed to the "position in the center of the reception aperture". Furthermore, the "inverse aperture function in which the center portion is zero" is one example in which the "range including a reception position" corresponds to a "range having a reception position (center of the reception aperture) as its center", and the width of the "range including a reception position" is half of the reception aperture width.

The "range" used to create the inverse aperture function can be changed by the control unit 18 or by an operator arbitrarily. Furthermore, the position of the "reception position at which a multiple reflection component is received" in the "range" is not limited to the center of the "range", and can be changed by the control unit 18 or by an operator arbitrarily, for example, to the center of gravity of the "range" or the like. Moreover, the weight of the "range" of the inverse aperture function is not limited to be uniformly "0", and as long as the above design concept is satisfied, it can be changed by the control unit 18 or by an operator arbitrarily. For example, the weight pattern in the "range" of the inverse aperture function may be such that a weight of positions at both ends of the range is "1", and a weight of the reception position is "0" sequentially decreasing toward the reception position from the ends.

By the control of the control unit 18, the transceiving unit 11 performs ultrasonic wave transmission/reception at each scan line forming a scan range. In other words, as illustrated in FIG. 11, the transceiving unit 11 applies a driving pulse for transmission to the ultrasound probe 1, receives a reflected wave signal from the ultrasound probe 1, and performs the DAS processing. Specifically, the reception delaying unit in the transceiving unit 11 gives an IQ signal of each transducer element, which is a reception signal, a reception delay and outputs the resultant signal to the adding unit. When "n types" of aperture functions are set in this case, as illustrated in FIG. 11, the adding unit separates a data string of the IQ signal into n systems, performs weighting by using a corresponding aperture function at each of the systems, and then performs phasing addition processing. Accordingly, as illustrated in FIG. 11, the acquiring unit 151 acquires a data string of "n" number of IQ signals "$IQ_1$, $IQ_2$, $IQ_3$, . . . , $IQ_n$" at a scan line. Subsequently, the compounding unit 152 compounds "$IQ_1$, $IQ_2$, $IQ_3$, . . . , $IQ_n$" by non-linear processing (multiplication processing). For example, when two types of aperture functions, namely the "normal aperture function of the hamming window" and the "inverse aperture function in which the center portion is zero", have been set, the compounding unit 152 multiplies "$IQ_1$" obtained using the "normal aperture function of the hamming window" by "$IQ_2$" obtained using the "inverse aperture function in which the center portion is zero" to generate a compound signal.

Subsequently, as illustrated in FIG. 11, the signal processing unit 153 performs phase detection on the compound signal (detection of phase information) and then performs signal processing using the phase information. For example, the signal processing unit 153 detects a phase difference between the two IQ signals of the compound signal composed of the two IQ signals from the phase term of the compound signal to perform the signal processing on the compound signal. A signal of each scan line output by the signal processing unit 153 is subjected to B-mode processing by the B-mode processing unit 12 and generation processing of B-mode image data by the image generating unit 14, and displayed on the monitor 2.

FIG. 12 illustrates B-mode image data of a short-axis plane of a human carotid artery. The upper left figure in FIG. 12 illustrates B-mode image data that visualizes "$IQ_1$" obtained using the "normal aperture function of the hamming window". The upper right figure in FIG. 12 illustrates B-mode image data that visualizes "$IQ_2$" obtained using the "inverse aperture function in which the center portion is zero". The lower figure in FIG. 12 illustrates B-mode image data that visualizes the compound signal of "$IQ_1$" and "$IQ_2$" without signal processing.

When focusing on a lumen of the carotid artery located in the center of each of the images illustrated in FIG. 12, the B-mode image data obtained using the "normal aperture function of the hamming window" has higher lateral resolution, but multiple reflection signals are superimposed, thereby degrading the visibility of the vascular lumen. On the other hand, the B-mode image data obtained using the "inverse aperture function in which the center portion is zero" presents degradation of image quality due to a reduction in lateral resolution, but multiple reflection signals are not present in the vascular lumen. The B-mode image data that visualizes the compound signal presents an image in which the lateral resolution is maintained by the effect of the "normal aperture function of the hamming window" and a reduction in the multiple reflection signals is ensured by the effect of the "inverse aperture function in which the center portion is zero".

The signal processing unit 153, for example, performs complex filtering that implements spatial smoothing on the compound signal of each of scan lines. The B-mode processing unit 12 and the image generating unit 14 generate image data from the compound signal subjected to the signal processing. The resultant image data has further improved image quality than that of the B-mode image data illustrated in the lower figure in FIG. 12 by the effect of the post-compounding signal processing by the signal processing unit 153.

As described above, in the second embodiment, a group of IQ signals that are output using a plurality of aperture functions having different effects of improving image quality, are compounded by non-linear processing, thereby generating a compound signal in which the effects provided by the respective aperture functions are maintained. Furthermore, in the second embodiment, significant phase information included in the compound signal is used for complex signal processing, thereby ensuring improvement in image quality of image data obtained by the signal compounding of the group of IQ signals output by using the aperture functions.

The second embodiment is applicable, for example, to the case of using only the various types of normal aperture functions as described above, and to the case of using a plurality of types of normal aperture functions and the "inverse aperture function in which the center portion is zero".

Figure 13:
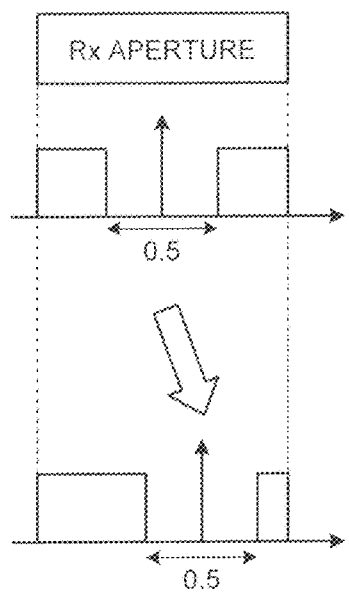
FIG. 13 is a diagram (1) for explaining a modification of the second embodiment.
Figure 14:
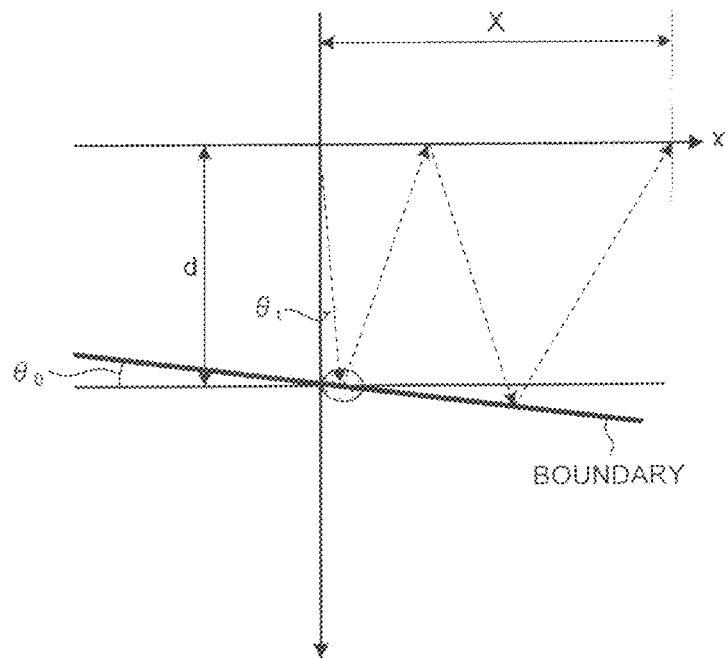
FIG. 14 is a diagram (2) for explaining the modification of the second embodiment.
Figure 15:
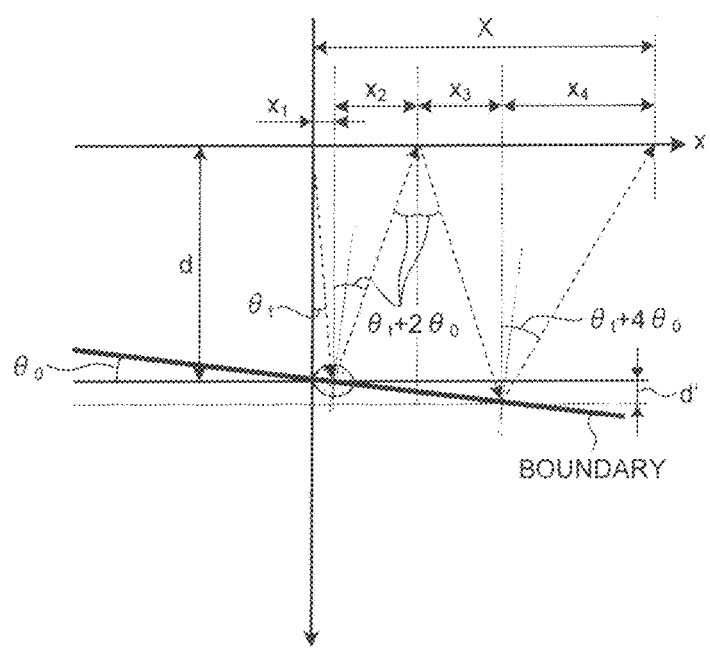
FIG. 15 is a diagram (3) for explaining the modification of the second embodiment.

In the above description, the case of using the "inverse aperture function in which the center portion is zero" has been described, which is one example of the "center-fixed inverse aperture-function" for which the reception position at which a multiple reflection component is received is fixed to the center of the reception aperture. As a modification, the second embodiment may be a case in which an IQ signal is acquired that is subjected to non-linear processing, using an inverse aperture function that adaptively shifts the "reception position at which a multiple reflection component is received" according to an imaging condition and an imaging part. FIG. 13 through FIG. 15 are diagrams for explaining the modification of the second embodiment.

When a "boundary formed at a subject causing multiple reflection and the probe surface are parallel", and a "direction of ultrasonic wave transmission/reception is perpendicular to the probe surface", "the directivity of a main beam of a reflected signal and the directivity of a main beam of a multiple reflection signal are in an identical direction", and "a reception position of a multiple reflection component is substantially at the center portion of the reception aperture similarly to the reception position of a reflection component". When these preconditions are satisfied, it is possible to remove multiplex signals by the "center-fixed inverse aperture-function".

However, in the inverse apodization with the "center-fixed inverse aperture-function", if a subject is inclined relative to the probe surface, the above preconditions are not satisfied, and it can be ineffective. Furthermore, in the inverse apodization with the "center-fixed inverse aperture-function", if a transmission beam is steered, the above preconditions are not satisfied, and it can be ineffective. That is, when the above preconditions are not satisfied, a reception position at which a multiple reflection component is received at the reception aperture is shifted toward an aperture end portion from the aperture center portion. In such a case, if the "center-fixed inverse aperture-function" is used, a multiple reflection signal is to be received at a transducer element position having a weight, and the multiple reflection reducing effect is degraded.

That is, a reception position at which a multiple reflection component is received at the reception aperture is shifted according to the relation between the direction of ultrasonic wave transmission/reception and the direction of a subject causing multiple reflection. However, assuming that multiple reflection by an angle formed with a direction of an ultrasonic wave transmission/reception and a direction of a subject (boundary formed by a subject being multiple reflection source) is caused by specular reflection, a position at which a reflected signal and a multiple reflection signal are received at the reception aperture can be estimated by geometrical operation.

Therefore, in the modification of the second embodiment, for example, the control unit 18 illustrated in FIG. 1 calculates a reception position based on a direction of ultrasonic wave transmission/reception and a direction of a subject causing multiple reflection, to create an inverse aperture function. For example, the control unit 18 uses the inverse aperture function of the aperture function in which the center portion is zero as a base as illustrated in FIG. 13. When the control unit 18 derives that a reception position in the reception aperture (Rx Aperture) is on a right side relative to the aperture center, from the direction of the ultrasonic wave transmission/reception and the direction of the subject, as illustrated in FIG. 13, a range in which a "weight: 0" is applied is shifted rightward. In the following, the inverse aperture function created by the concept illustrated in FIG. 13 is described as a "shifted inverse aperture-function" in some cases. Moreover, in the following, the inverse apodization by the "shifted inverse aperture-function" is described as "shifted inverse apodization" in some cases. Furthermore, in the following, the inverse apodization by the "center-fixed inverse aperture-function" is described as "fixed inverse apodization" in some cases.

The shifted inverse apodization is performed by the control unit 18 acquiring parameters illustrated in FIG. 14. In FIG. 14, a direction of arrangement of transducer elements (lateral direction) is indicated by an x axis. Moreover, in FIG. 14, a direction that passes through a center position of the reception aperture (that is, a depth direction) perpendicular to the x axis is indicated by a downward arrow. In the following, explanation is given assuming that the center position of the reception aperture (and the transmission aperture) is an origin (0, 0).

Furthermore, FIG. 14 indicates that an angle "$A_r$" formed by a direction of a transmission/reception beam and the depth direction is used as one example of a parameter indicating the direction of the transmission/reception beam. Moreover, FIG. 14 indicates that an angle "$\theta_0$" formed by the direction of the transmission/reception beam and the x axis is used as one example of a parameter indicating the direction of the subject. Furthermore, "d" illustrated in FIG.

14 indicates a depth of a position at which an ultrasonic beam transmitted at the angle "$\theta_t$" is first reflected on a boundary formed by the subject inclined at the angle "$\theta_0$". That is, "d" illustrated in FIG. 14 indicates the depth at which the subject is positioned on a scan line.

Moreover, "X" illustrated in FIG. 14 indicates a distance from the center position of the reception aperture to a reception position at which a main beam of a single multiple reflection is received at the reception aperture. That is, "X" indicates a reception position that is a reference used to set a range in which a weight is reduced, and is to be, for example, a center of gravity position (center position) of a range in which a transducer element group a weight of which is set to "0" by the shifted inverse aperture-function occupies. The control unit 18 calculates "X" by, for example, multiplying a function $F(\theta_t,\theta_0)$ that is formulated with the angle "$\theta_t$" and the angle "$\theta_0$" by "d". This $F(\theta_t,\theta_0)$ is explained in detail later using mathematical expressions.

First, a method of acquiring various kinds of parameters illustrated in FIG. 14 is explained. Because the control unit 18 controls ultrasonic wave transmission/reception, the control unit 18 can acquire the angle "$\theta_n$" indicating a direction of a transmission/reception beam. That is, the control unit 18 acquires the angle "$\theta_t$" from various kinds of transmission/reception conditions that are set prior to ultrasonic scanning. For example, the control unit 18 acquires the angle "$\theta_t=0$" in normal B-mode imaging.

Furthermore, the control unit 18 acquires the angle "$\theta_0$" indicating a direction of a subject by various methods explained below. In the simplest method, the control unit 18 acquires a value that is initially set as the angle "$\theta_0$" in advance. For example, the control unit 18 acquires the angle "$\theta_0=0$", "$\theta_0=3$", or the like from setting values stored in the internal storage unit 17. In such a case, an operator can change the value "$\theta_0$" initially set, arbitrarily according to information of an examined part, and the like.

Alternatively, the angle "$\theta_0$" indicating a direction of a subject can be acquired using ultrasonic image data that is acquired by imaging in advance a scanning range in which actual ultrasonic scanning is performed by normal B-mode. In such a case, the control unit 18 acquires a direction of a subject based on information input by an operator referring to ultrasonic image data that has been acquired in advance. For example, the control unit 18 causes the monitor 2 to display B-mode image data that is acquired beforehand by preliminary imaging. For example, the operator measures the inclination of a blood vessel wall causing a multiplex signal, by turning a knob for the angle measurement included in the input device 3, to measure an angle of the "signal". The control unit 18 acquires the angle measured with the knob by the operator as the angle "$\theta_0$" indicating a direction a subject.

Because measuring a direction of a subject manually is processing needing an effort for an operator, the control unit 18 may acquire a direction of a subject automatically. When automation of acquisition processing for the angle "$\theta_0$" is specified, the control unit 18 analyzes ultrasonic image data that has been acquired in advance, to estimate a direction of a subject. For example, the control unit 18 estimates the angle "$\theta_0$" indicating a direction of a subject by performing edge detection or main component analysis as analysis processing of the B-mode image data acquired by preliminary imaging. For example, the control unit 18 performs edge enhancement processing of the B-mode image data to acquire a normal vector and then detects an edge from the acquired normal vector. Subsequently, the control unit 18 estimates the angle "$\theta_0$" from a direction of the detected edge. The above method is merely an example, and the control unit 18 can estimate the angle "$\theta_0$" by various widely known methods.

When the angle "$\theta_s$" is performed by detection processing of image information, to reduce a load, the control unit 18 may perform the following processing. Specifically, the control unit 18 performs the detection processing of image information, limiting to a region of interest (ROI) specified for B-mode image data imaged in advance. For example, the ROI is specified by an operator that has referred to the B-mode image data. Alternatively, to reduce a load on an operator, the control unit 18 may automatically set the ROI. Usually, a region drawn in the center of an image is a region that is particularly focused in image diagnosis. Therefore, to avoid a multiplex signal being drawn in the center of an image, the control unit 18 automatically sets the ROI in a certain shape while setting the center of the image as a center.

Alternatively, the control unit 18 uses a depth at which a tissue of a subject of examination is positioned from a contact surface of the ultrasound probe 1, as a parameter used for automatic setting of the ROI. For example, the control unit 18 acquires information indicating that a tissue of a subject of examination is a "carotid artery" from information relating to examination that has been input in advance. Usually, the depth at which a carotid artery is positioned from a contact surface of the ultrasound probe 1 is near "10 mm". For example, the internal storage unit 17 stores therein, for each tissue of a subject of examination, a table containing a setting of a representative depth at which the tissue is positioned. The control unit 18 refers to the table to acquire a depth that is associated with the tissue acquired from the examination information, to set the ROI in a certain shape. The control unit 18 automatically sets the ROI setting the depth at which the tissue of a subject of examination is positioned in center, to avoid a multiplex signal being drawn in a region in which the tissue of a subject of examination is to be drawn.

Alternatively, the control unit 18 uses a position of a transmission focus as a parameter used for automatic setting of the ROI. A region having the position of the transmission focus as its center is also a region that is particularly focused in image diagnosis. Therefore, to avoid a multiplex signal being drawn in a region including the position of the transmission focus, the control unit 18 automatically sets the ROI while setting the depth position of the transmission focus as a center.

The control unit 18 according to the second embodiment can perform two patterns of the shifted inverse apodization. In a first pattern, the control unit 18 calculates a reception position of a multiple reflection component without acquiring a depth "d" at which a subject is positioned on a scan line. Specifically, the control unit 18 calculates a reception position assuming that the subject is positioned at respective depths of reception focuses set on a reception scan line.

For example, the control unit 18 sets depths of a plurality of reception focuses on a scan line as "d" that is used to calculate the reception position. The control unit 18 causes the transceiving unit 11 to perform the DVAF method for changing a width of the reception aperture according to a position of a reception focus. The control unit 18 then calculates the reception position at the reception aperture at each reception focus. The control unit 18 calculates the reception position at the reception aperture at each reception focus for each of reception scan lines from the angle "$\theta_t$" and the angle "$\theta_0$".

The control unit 18 then creates a "shifted inverse aperture-function" based on a reception position at the reception aperture of each reception focus, and informs the transceiving unit 11 of the "shifted inverse aperture-function", thereby performing the shifted inverse apodization in parallel with normal apodization.

A calculation method of a reception position of a multiple reflection component is explained in detail using FIG. 15 and mathematical expressions. FIG. 15 indicates that a position (hereinafter, P1) where an ultrasonic beam that has been transmitted at the angle "$\theta_t$" first reaches on a boundary inclined by "$\theta_0$" is ($x_1$, d). Moreover, FIG. 15 indicates that a reception position (hereinafter, P2) on the probe surface of the reflected wave that has been reflected at P1 by specular reflection with the angle "$\theta_f$" and the angle "$\theta_s$" is ($x_t+x_2$, 0). Furthermore, FIG. 15 indicates that a position (hereinafter, P3) where the reflected wave reflected at P2 reaches the boundary again, by the specular reflection with the angle "$\theta_t$" and the angle "$\theta_0$" is ($x_1+x_2+x_3$, d+d'). Moreover, FIG. 15 indicates that a reception position (hereinafter, P4) on the probe surface of the reflected wave that has been reflected at P3 by specular reflection with the angle "$\theta_t$" and the angle "$\theta_0$" is ($x_1+x_2+x_3+x_4$, 0).

"X" illustrated in FIG. 15 calculated in shifted inverse-reception apodization, that is, the reception position "X" to be a reference for setting a range in which a transducer element group a weight of which is set to substantially "0" by the aperture function occupies is "X=$x_1+x_2+x_3+x_4$" as illustrated in FIG. 15.

First, an "angle between a direction from the origin to P1 and a depth direction" is "$\theta_t$" as illustrated in FIG. 15. Furthermore, by geometrical operation assuming that reflection occurring between the angle "$\theta_t$" and the angle "$\theta_0$" is specular reflection, the "angle between a direction from P1 to P2 and a depth direction" and the "angle between a direction from P2 to P3 and a depth direction" are "$\theta_t+2\theta_0$" as illustrated in FIG. 15. Moreover, by similar geometrical operation, an "angle between a direction from P3 to P4 and a depth direction" is "$\theta_t+4\theta_0$" as illustrated in FIG. 15.

First, from "$\theta_t$" and "d", the control unit 18 calculates "$x_1$" by Equation 12 below. Furthermore, the control unit 18 calculates "$x_2$" from "$\theta_t+2\theta_0$" and "d" by Equation 13 below.

$$x_1 = d \cdot \tan(\theta_t) \tag{12}$$

$$x_2 = d \cdot \tan(\theta_t + 2\theta_0) \tag{13}$$

On the other hand, from "$\theta_t+2\theta_0$", "d", and "d'", "$x_3$" can be expressed by Equation 14 below. Furthermore, from "$\theta_t+4\theta_0$", "d", and "d'", "$x_4$" can be expressed by Equation 15 below.

$$x_3 = (d + d') \cdot \tan(\theta_t + 2\theta_0) = x_2 + d' \cdot \tan(\theta_t + 2\theta_0) \tag{14}$$

$$x_4 = (d + d') \cdot \tan(\theta_t + 4\theta_0) \tag{15}$$

Moreover, "d'" can be expressed by Equation 16 below.

$$d' = (x_2 + x_3) \cdot \tan(\theta_0) = (2x_2 + d' \cdot \tan(\theta_t + 2\theta_0)) \cdot \tan(\theta_0) \tag{16}$$

By developing Equation 16, Equation 17 below can be obtained.

$$d'(1 - \tan(\theta_t + 2\theta_0) \cdot \tan(\theta_0)) = 2x_2 \cdot \tan(\theta_0) \tag{17}$$

When an addition theorem of a trigonometric indicated in Equation 18 is applied, "$1-\tan(\theta_t+2\theta_0)\cdot\tan(\theta_0)$" expressed in the left side of Equation 17 is to be the right side of Equation 19 below.

$$\tan(\alpha + \beta) = \frac{\tan\alpha + \tan\beta}{1 - \tan\alpha \, \tan\beta} \tag{18}$$

$$1 - \tan(\theta_t + 2\theta_0) \cdot \tan(\theta_0) = [\tan(\theta_t + 2\theta_0) + \tan(\theta_0)]/\tan(\theta_t + 3\theta_0) \tag{19}$$

It is illustrated that by substituting Equation 19 into Equation 17, "d'" can be calculated from "$x_2$", "$\theta_t$", and "$\theta_0$" as indicated in Equation 20 below.

$$d' = 2x_2 \cdot \tan(\theta_0) \tan(\theta_t + 3\theta_0) / [\tan(\theta_t + 2\theta_0) + \tan(\theta_0)] \tag{20}$$

From the above, "$x_3$" can be calculated by Equation 21 below, and "$x_4$" can be calculated by Equation 22 below.

$$\begin{aligned}x_3 &= (d + d') \cdot \tan(\theta_t + 2\theta_0) \\ &= x_2 \cdot (1 + 2 \cdot \tan(\theta_t + 2\theta_0) \cdot \tan(\theta_0) \cdot \tan(\theta_t + 3\theta_0) / \\ &\quad [\tan(\theta_t + 2\theta_0) + \tan(\theta_0)])\end{aligned} \tag{21}$$

$$\begin{aligned}x_4 &= (d + d') \cdot \tan(\theta_t + 4\theta_0) \\ &= x_2 \cdot (1 + 2 \cdot \tan(\theta_t + 4\theta_0) \cdot \tan(\theta_0) \cdot \tan(\theta_t + 3\theta_0) / \\ &\quad [\tan(\theta_t + 2\theta_0) + \tan(\theta_0)])\end{aligned} \tag{22}$$

The control unit 18 acquires the angle "$\theta_t$" and the angle "$\theta_0$" by the above method, and calculates "$x_1$" and "$x_2$" by substituting the depth "d" of a reception focus, by Equation 12 and Equation 13. Using calculated "$x_2$", "$\theta_t$", and "$\theta_0$", the control unit 18 then calculates "$x_3$" and "$x_4$" by Equation 21 and Equation 22, respectively. Subsequently, the control unit 18 calculates "$x_1+x_2+x_3+x_4$" to acquire a reception position "X". As is obvious from Equation 12, Equation 13, Equation 21, and Equation 22, when "d" is factored as a common factor, "X=$x_1+x_2+x_3+x_4$" can be formulated by a product of a function $F(\theta_t,\theta_0)$ that is expressed with the angle "$\theta_t$" and the angle "$\theta_0$", and "d". The control unit 18 can calculate the reception position "X" at the reception aperture set for each reception focus by multiplying a value obtained by substituting the acquired angles "$\theta_t$" and "$\theta_0$" into $F(\theta_t,\theta_0)$ by an arbitrary depth "d".

This is the first pattern of the shifted inverse apodization. In the first pattern, a depth of a subject is a reception focus position, and a position of "X" is automatically calculated with $F(\theta_t,\theta_0)$ and "F-number". However, in the first pattern, because a transducer element group a weight of which is "0" at each depth "d" is always present, the effective aperture width is small compared to the normal reception apodization.

On the other hand, in a shifted inverse apodization of a second pattern, the control unit 18 further acquires a depth "d" at which a subject is present on a scan line, to calculate a reception position "X". That is, in the shifted inverse apodization of the second pattern, the control unit 18 calculates a reception position "X" based on a direction of ultrasonic wave transmission/reception, a direction of a subject causing multiple reflection, and a depth of the subject causing multiple reflection, to create the inverse aperture function.

In the second pattern, for example, an operator measures the angle "$\theta_0$", and also measures a depth "$d_0$" of the subject at the same time by referring to B-mode image data imaged in advance. The control unit 18 acquires the depth measured by the operator as the depth "$d_0$" of the subject.

Alternatively, the control unit 18 estimates the angle "$\theta_0$" by edge detection or main component analysis as described above, and for example, acquires the depth "$d_0$", regarding an edge extracted by the edge detection as a boundary formed on the subject, by automatically measuring a position of the edge in an image.

Alternatively, the control unit 18 acquires "$d_0$" from among various parameters that are used for setting the ROI described above. Specifically, the control unit 18 acquires an "image center", a "representative depth of a tissue of a subject of examination", or a "transmission focus" that is used for setting the ROI as "$d_0$". By setting as "transmission focus=$d_0$", it is possible to respond immediately to a change of a transmission/reception condition during imaging.

For example, "$d_0$" input by an operator is a depth at a right end of a subject drawn in an image. In such a case, the control unit 18 calculates a depth "$d_i$" of a subject on each scan line from the angle "$\theta_0$" and "$d_0$", and creates the shifted inverse aperture-function at each scan line by "$d_i \cdot F(\theta_i, \theta_0)$". Subsequently, the control unit 18 instructs the transceiving unit 11 to use the created shifted inverse aperture-function at a reception focus of the depth "$d_i$", or at a reception focus near the depth "$d_i$", and further instructs the transceiving unit 11 to use the normal aperture function at reception focuses other than this reception focus.

That is, the shifted inverse apodization of the second pattern is inverse apodization that applies a shifted inverse aperture-function to a reception focus corresponding to a depth of a subject, and applies a normal aperture function to a reception focus far from the depth of the subject. In other words, the first pattern that does not use a depth of a subject is a pattern for setting a uniform shifted inverse aperture-function in an entire image (all sample points), and the second pattern that uses a depth of a subject is a pattern for setting a shifted inverse aperture-function that is adaptively created for a local region in an entire image (all sample points).

In the modification of the second embodiment, by the processing described above, the inverse aperture function for which a reception position is shifted according to an imaging condition and a position of a subject in a portion to be imaged can be applied to the inverse apodization. In a reception signal that is acquired by the shifted inverse apodization of the first pattern or the shifted inverse apodization of the second pattern, a multiple reflection component is reliably reduced compared to a reception signal that is acquired by the fixed inverse apodization. Moreover, the reception signal that is acquired by the shifted inverse apodization of the second pattern is a reception signal that is acquired by performing the inverse apodization limiting to a local region, and therefore, the sensitivity thereof is higher than that of a reception signal that is acquired by the shifted inverse apodization of the first pattern in which the overall effective aperture width is narrow.

In the modification of the second embodiment, for example, an IQ signal acquired by the normal apodization and an IQ signal acquired by the shifted inverse apodization are compounded by non-linear processing to generate a compound signal, and various complex signal processing are performed on the compound signal. Accordingly, a high quality image in which, for example, multiple reflection is reduced, and the lateral resolution and the sensitivity are maintained can be acquired reliably.

A concept of the shifted inverse apodization described above is also applicable, for example, to the normal apodization that uses the normal aperture function of the hamming window. For example, "$x_1+x_2$" that can be calculated by Equation 12 and Equation 13 is to be a position at which a signal component is received. Therefore, for example, the control unit 18 may create a shifted normal aperture-function for which a position at which a weight in the hamming window is "1" is "$x_1+x_2$" when a position of "$x_1+x_2$" is distant more than a certain distance from the center of the reception aperture, and inform the transceiving unit 11 of the shifted normal aperture-function. That is, in the modification of the second embodiment, a plurality of IQ signals may be acquired by performing the shifted normal apodization and the shifted inverse apodization in parallel.

Third Embodiment

Figure 16:
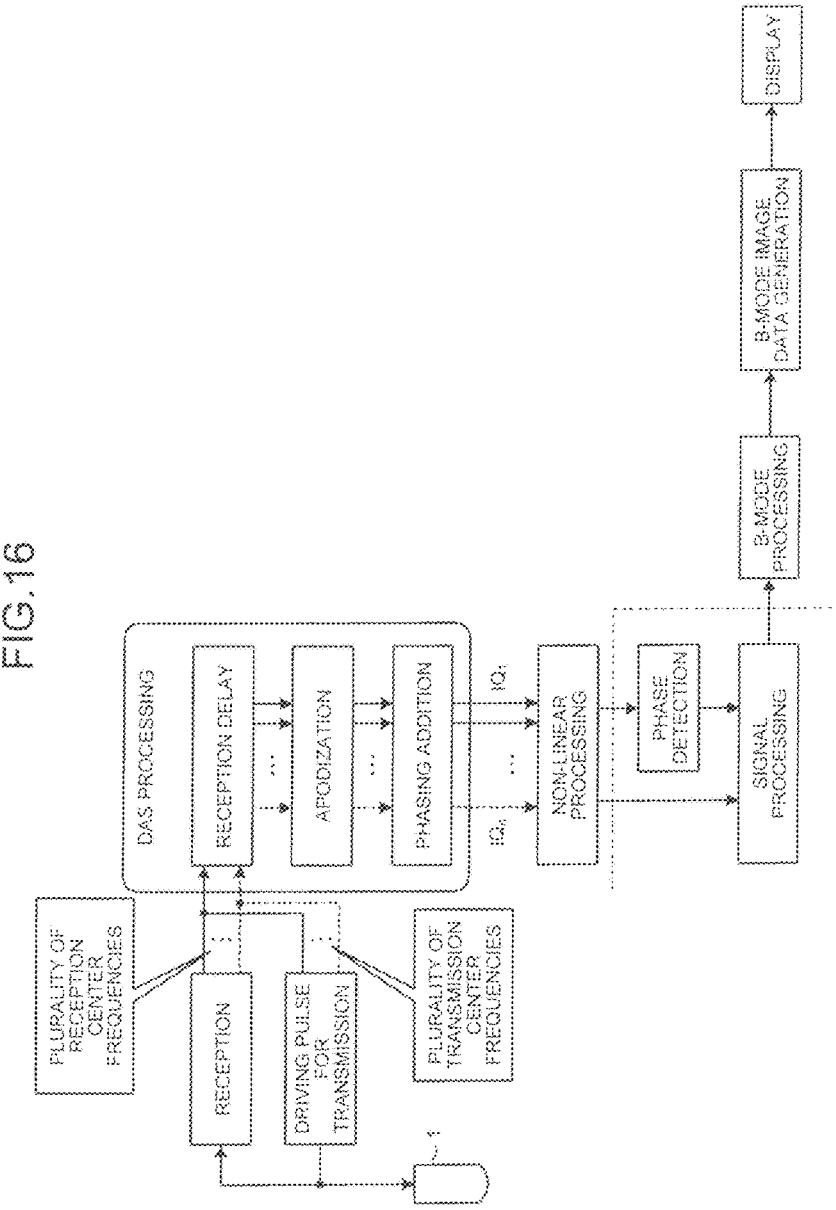
FIG. 16 is a diagram for explaining a third embodiment.

In the third embodiment, a case is explained in which the "plurality of processing" explained in the first embodiment are "a plurality of processing" based on different ultrasonic wave transmission/reception conditions. FIG. 16 is a diagram for explaining the third embodiment.

For example, in the third embodiment, as illustrated in FIG. 16, a plurality of processing are processing that use a plurality of different frequencies for at least one of the transmission center frequency of an ultrasonic wave and the reception center frequency of the ultrasonic wave. For example, the transceiving unit 11 causes the ultrasound probe 1 to transmit ultrasonic beams having different center frequencies at each scan line, and outputs a plurality of IQ signals "$IQ_1, IQ_2, IQ_3, \ldots, IQ_n$" at each scan line by the DAS processing using reflected wave signals having the respective transmission center frequencies.

Alternatively, for example, the transceiving unit 11 causes the ultrasound probe 1 to transmit ultrasonic beams having one type of center frequency and detects a plurality of frequencies from received reflected wave signals, and performs the DAS processing on each of the reception center frequencies so as to output the IQ signals "$IQ_1, IQ_2, IQ_3, \ldots, IQ_n$" at each scan line. Alternatively, for example, the transceiving unit 11 uses a plurality of center frequencies for both transmission and reception so as to output the IQ signals "$IQ_1, IQ_2, IQ_3, \ldots, IQ_n$" at each scan line. Accordingly, the acquiring unit 151 acquires the IQ signals "$IQ_1, IQ_2, IQ_3, \ldots, IQ_n$", and the compounding unit 152 generates a compound signal by non-linear processing as illustrated in FIG. 16.

The above described plurality of processing are what is called frequency compounding processing for the purpose of the effect of speckle reduction. For example, a compound signal that is compounded by performing multiplication processing on a plurality of IQ signals obtained by detecting a plurality of frequencies at reception, can provide the same effect of speckle reduction as that of frequency compounding processing. Furthermore, because a main beam width depends on a frequency (proportional to the inverse of a center frequency), the compound signal maintains the effect of lateral resolution obtained by IQ signals having center frequencies on the high frequency side.

Subsequently, as illustrated in FIG. 16, the signal processing unit 153 performs phase detection on the compound signal (detection of phase information) and then performs signal processing using the phase information. A signal of each scan line output by the signal processing unit 153 is subjected to B-mode processing by the B-mode processing unit 12 and generation processing of B-mode image data by the image generating unit 14, and displayed on the monitor 2.

Accordingly, in the third embodiment, the effect of image quality improvement provided by the frequency compounding processing can be increased by performing signal compounding by non-linear processing, thereby obtaining image data having higher image quality than that of the image data acquired by the frequency compounding processing.

Fourth Embodiment

Figure 17:
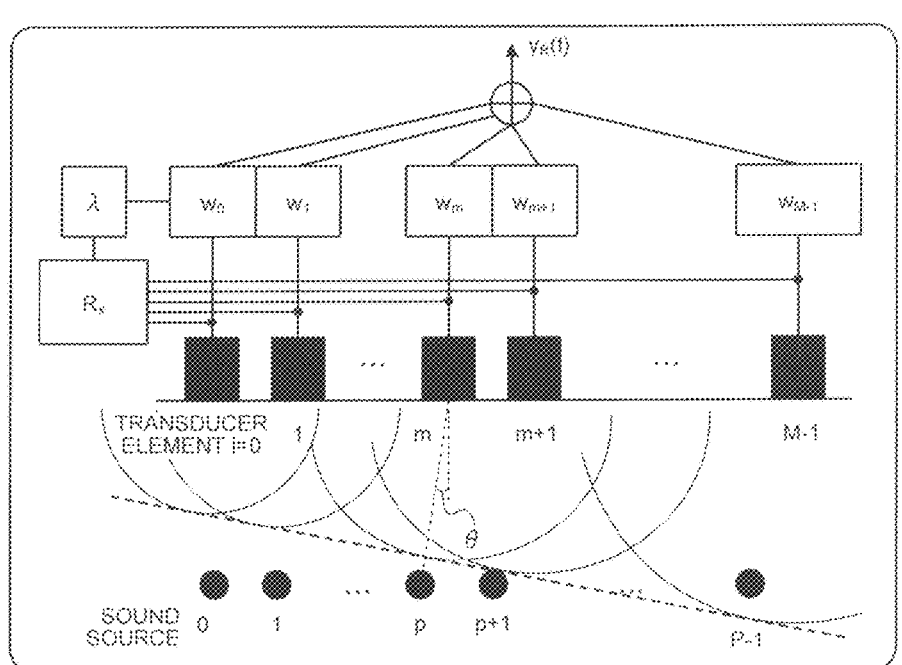
FIG. 17 is a diagram (1) for explaining a fourth embodiment.

In the fourth embodiment, a case is explained in which "parallel processing of reception beam forming in a plurality of systems" that is different from that of the second embodiment is performed as the "plurality of processing" explained in the first embodiment, using FIG. 17 and FIG. 18, for example. FIG. 17 and FIG. 18 are diagrams for explaining the fourth embodiment.

For example, the "parallel processing of reception beam forming in a plurality of systems" may be performed by using a plurality of sonic speeds having different values as sonic speeds used for setting a reception delay pattern. For example, as preliminary processing, the control unit 18 analyzes a plurality of pieces of B-mode image data acquired by a reception delay pattern using a plurality of sonic speeds, and acquires a first sonic speed at which B-mode image data having a high contrast is obtained at a shallow portion and a second sonic speed at which B-mode image data having a high contrast is obtained at a deep portion. Alternatively, for example, an operator inputs the first sonic speed and the second sonic speed using the input device 3.

Subsequently, by the control of the control unit 18, the transceiving unit 11 separates IQ signals of each transducer element received at the reception aperture in this imaging into two systems, and outputs, to the acquiring unit 151, an IQ signal subjected to the DAS processing in a reception delay pattern using the first sonic speed, and an IQ signal subjected to the DAS processing in a reception delay pattern using the second sonic speed. The compounding unit 152 generates a compound signal by compounding the two IQ signals by multiplication processing, for example. The compound signal is a signal capable of generating image data that presents a high contrast at both of a shallow portion and a deep portion. The signal processing unit 153 performs complex signal processing on the compound signal and outputs the resultant signal to the B-mode processing unit 12. Accordingly, the image generating unit 14 can generate B-mode image data that presents a high contrast at both of a shallow portion and a deep portion, and has image quality improved by the complex signal processing. The above description is merely an example. The present embodiment may be a case in which processing using three or more sonic speeds are performed.

Alternatively, for example, the "parallel processing of reception beam forming in a plurality of systems" may be performed by using a plurality of aperture widths having different values as the aperture width of the reception aperture. For example, when the width of the reception aperture is wide, although the lateral resolution is improved, not only a region in which reflected waves having a matching phase enter but also a region in which reflected waves having non-matching phases are mixed in a direction of arrangement of the transducer elements at the reception aperture. As a result, noise is superimposed on a signal obtained at the reception aperture having a large diameter, and the possibility of obtaining image data having a low S/N ratio is increased. On the other hand, when the width of the reception aperture is narrow, only a region in which reflected waves having a matching phase enter can be an effective aperture and image data having a high S/N ratio is obtained. However, an effective aperture is narrowed and the lateral resolution is possibly reduced.

Therefore, for example, by the control of the control unit 18, the transceiving unit 11 outputs, to the acquiring unit 151, an IQ signal from a large diameter obtained by the DAS processing performed on an IQ signal group obtained at an entire region of the reception aperture having the large diameter as one system, and an IQ signal from a small diameter obtained by the DAS processing performed on an IQ signal group obtained at a part of the region of the reception aperture having the large diameter as another system. The compounding unit 152 generates a compound signal by compounding the two IQ signals by multiplication processing, for example. The compound signal is a signal capable of generating image data having high lateral resolution and a high S/N ratio. The signal processing unit 153 performs complex signal processing on the compound signal and outputs the resultant signal to the B-mode processing unit 12. Accordingly, the image generating unit 14 can generate B-mode image data having high lateral resolution, a high S/N ratio, and image quality improved by the complex signal processing. The above description is merely an example. The present embodiment may be a case in which processing using three or more aperture widths are performed.

Alternatively, for example, the "parallel processing of reception beam forming in a plurality of systems" may be performed by using other aperture function than the various aperture functions described in the second embodiment. For example, a plurality of aperture functions for performing the "parallel processing of reception beam forming in a plurality of systems" may include an aperture function in which a weighting pattern is changed according to phase distribution of signals received by a plurality of transducer elements structuring the reception aperture. Such an aperture function is, for example, an aperture function obtained by adaptive array (AA) processing that designs reception apodization adaptively. The AA processing is a method that is applied to a model for an array imaging system in which a delay is applied to channel signals to form directivity and weighting addition is adaptively performed on the channel signals having the delay. More specifically, the AA processing sets an array transducer element group in which a plurality of transducer elements are arranged, and adaptively controls a weight (generally a complex number coefficient) assigned to channel signals obtained from the transducer elements according to a propagation environment, thereby giving optimized directivity to the reception signals depending on the environment. The AA processing is explained using FIG. 17.

FIG. 17 exemplifies a transducer element group (channel group) structuring the reception aperture by M−1 number of transducer elements (i=0, 1, . . . , m, m+1, . . . M−1). FIG. 17 also exemplifies reflection sources (sample points) positioned at the same depth from an arrangement surface of the transducer element group by P number of sound sources (0, 1, p, p+1, . . . , P−1).

The transceiving unit 11 that performs the AA processing receives input of reception signals (IQ signals) of the transducer elements in a state in which a delay is given by the reception delaying unit, and calculates a correlation matrix "$R_x$" of the reception signals of the transducer elements after the delay is given. The transceiving unit 11 then determines an optimum weight coefficient w ($w_0$, $w_1$, . . . , $w_m$, $w_{m+1}$, . . . , $w_{M-1}$) for each point (each of the transducer elements) from the correlation matrix "$R_x$". Specifically, the transceiving unit 11 calculates a characteristic value "λ" of the correlation matrix "$R_x$", and determines an optimum weight coefficient using the characteristic value "λ". Accordingly, the transceiving unit 11 outputs an IQ signal "$y_R(t)$" based on the AA processing. Because an input data set includes IQ signals, the weight coefficient determined by the transceiving unit 11 is a complex number. The weight coefficient is determined for each transducer element and sample point. The transceiving unit 11 may use not only a method for determining an optimum weight coefficient from a characteristic value of a correlation matrix, but also an iterative method or the like as long as it is equivalent to the above described method.

As illustrated in FIG. 17, a deflection angle "θ" varies depending on the positions of a sound source and a transducer element. Thus, the characteristic value "X" varies depending on the deflection angle "θ". The correlation matrix "$R_x$" also depends on the status of an input signal. Therefore, the transceiving unit 11 determines, for each transducer element, the weight coefficient w that varies adaptively depending on a propagation environment. The transceiving unit 11 uses, for example, a minimum variance (MV) method or an amplitude and phase estimation (APES) method as a design method for determining the weight coefficient w from the correlation matrix "$R_x$". Alternatively, the transceiving unit 11 may use another design method as long as it is a method for reducing a side lobe adaptively.

The MV method is a method that sets an array gain in a direction to be visualized to "1", and determines a weight coefficient such that signal energies from other directions are minimized. For example, in the MV method, when a finite number of sound sources are present, a weight coefficient is determined by setting the response to a sound source in a direction to be visualized to a gain "1", and setting the directivity to the rest of the sound sources to "0 (Null point)". In the APES method, a weight coefficient is determined such that an error with respect to a plane wave from a direction to be visualized is minimized.

By performing the design methods described above, the transceiving unit 11 can generate IQ signals at each scan line in a state in which a side lobe and the main lobe included in a reception signal are minimized and maximized, respectively, depending on an environment, that is, a status of a living body. By applying the design methods described above, the transceiving unit 11 (or the control unit 18) can adaptively design an aperture function that can provide the same effect as that of the center-fixed inverse aperture-function and the shifted inverse aperture-function described in the second embodiment.

For example, an inverse aperture function in which the center portion is zero is an aperture function that uses a tendency in which the phase distribution of reflected signals from a tissue in a direction of transducer elements and the phase distribution of multiple reflection signals in the direction of transducer elements are the same in the center portion of the reception aperture. When focusing on the phase distribution in the direction of transducer elements in the reception aperture, phase information is present in which a strong linear relation between signals of adjacent transducer elements indicates reflected signals from a tissue, and a weak linear relation indicates scattered signals. By using the phase information, an inverse aperture function can be designed adaptively by the AA processing. For example, transceiving unit 11 (or the control unit 18) analyzes a phase of a detected frequency used for visualization, and designs an inverse aperture function in which an weight on a transducer element at a position having a strong linear relation in a direction of transducer elements is small while an weight on a transducer element at a position having a weak linear relation is large.

Subsequently, for example, as illustrated in FIG. 18, the transceiving unit 11 separates an IQ signal group in which a reception delay is given to signals acquired by the transducer elements at the reception aperture into two systems, and, for example, performs the DAS processing using the normal aperture function of the hamming window and the AA processing using an inverse aperture function designed adaptively based on phase distribution. Accordingly, the acquiring unit 151 acquires an IQ signal "$IQ_1$" based on the DAS processing and an IQ signal "$IQ_2$" based on the AA processing, and the compounding unit 152 generates a compound signal by compounding the two IQ signals by multiplication processing, for example. Similarly to the compound signal obtained in the second embodiment, the compound signal is a signal capable of generating image data having a reduced multiple reflection component and high lateral resolution. The signal processing unit 153 performs complex signal processing on the compound signal and outputs the resultant signal to the B-mode processing unit 12. Accordingly, the image generating unit 14 can generate B-mode image data having a reduced multiple reflection component, high lateral resolution, and image quality improved by the complex signal processing.

The above description is merely an example. The present embodiment may be a case in which a normal aperture function is designed by an adaptive concept described above, and the AA processing is performed using the adaptively designed inverse aperture function and normal aperture function. Furthermore, the present embodiment may be a case in which the DAS processing is performed using the inverse aperture function and normal aperture function described in the second embodiment, and the AA processing is further performed using an inverse aperture function and normal aperture function obtained by the above described adaptive design methods.

In the above processing, the AA processing may be performed either by the APES method or the MV method. Moreover, an aperture function adaptively designed by the AA processing may be, as described above, an aperture function for reducing side lobes that is an original purpose of adaptive array. For example, while the APES method provides the effect of reducing side lobes, a normal APES method designs a weight coefficient so as to give directivity to effective reception transducer elements in the front direction, thereby decreasing the weight of other signals than that reflected in the front direction. Therefore, the normal APES method has a disadvantage in which, if an inclined tissue is present in a scanning region, a signal originated in the tissue is possibly eliminated by a small weight. By compounding an IQ signal obtained by using a weight coefficient determined based on a normal APES method in the AA processing and an IQ signal obtained by using the aperture function of the hamming window in a general DAS processing, the disadvantage can be reduced, and the effect of reducing side lobes, which is provided by the APES method, can be provided.

The plurality of processing described in the second embodiment and the third embodiment can be performed in any combination. In any case, by compounding, using non-linear processing, a plurality of IQ signals obtained by a plurality of respective processing, a compound signal can be obtained in which advantages of the respective processing are maintained and disadvantages of the respective processing are compensated by the advantages of other processing.

Fifth Embodiment

In the fifth embodiment, various display modes are explained that can be implemented in the first embodiment through the fourth embodiment.

The first embodiment through the fourth embodiment acquire a plurality of IQ signals by a plurality of parallel processing, to perform compounding processing and post-compounding signal processing and to perform pre-compounding signal processing, compounding processing, and post-compounding signal processing. Thus, image data for display that can be finally output to the monitor 2 present in plurality.

That is, if pre-compounding signal processing is not performed, the control unit 18 can output, to the monitor 2, image data generated from a compound signal subjected to signal processing (post-compounding signal processing) as well as at least one image data among a plurality of pieces of image data generated from a plurality of respective IQ signals and image data generated from a compound signal, as an image data group for display.

If the pre-compounding signal processing is performed, the control unit 18 can output, to the monitor 2, image data generated from a compound signal subjected to signal processing (post-compounding signal processing) as well as at least one image data among a plurality of pieces of image data generated from a plurality of respective IQ signals, a plurality of pieces of image data generated from a plurality of respective IQ signals subjected to signal processing (pre-compounding signal processing), and image data generated from a compound signal, as an image data group for display.

By an instruction from the control unit 18, the monitor 2 can implement a display mode in which the image data group for display is displayed at the same time. However, a large number of pieces of image data for display provide a large quantity of information, thus making diagnosis difficult in some cases. Therefore, by an instruction from the control unit 18, the monitor 2 can implement a display mode in which display is performed by switching the pieces of image data constituting the image data group for display.

For allowing an image interpreter to confirm that the effects obtained from the plurality of respective processing are maintained in the image data obtained by the non-linear compounding processing and the post-compounding signal processing, the control unit 18 may control inclusion of at least one image data among a plurality of pieces of image data generated from a plurality of respective compounding-source IQ signals in the image data group for display. Furthermore, for allowing an image interpreter to confirm improvement of image quality before and after the post-compounding signal processing, the control unit 18 may control inclusion of image data generated from a compound signal in the image data group for display.

Specific examples of the above described display control are explained using FIG. 19 and FIG. 20A through FIG. 20C. FIG. 19 and FIG. 20A through FIG. 20C are diagrams for explaining the fifth embodiment.

For example, FIG. 19 illustrates an image data group for display that can be output to the monitor 2 when parallel processing of a plurality of reception apodization is performed using a plurality of various aperture functions explained in the second embodiment. The following describes a case of not performing pre-compounding signal processing as one example.

For example, FIG. 19 illustrates that a signal "IQ" obtained by the non-linear processing and the post-compounding signal processing is output to the B-mode processing unit 12 and a plurality of compounding-source IQ signals "$IQ_1, \ldots, IQ_2$," are output to the B-mode processing unit 12. If the compounding-source IQ signals are "$IQ_1$" obtained using the normal aperture function of the hamming window and "$IQ_2$" obtained using the inverse aperture function in which the center portion is zero, by an instruction from the control unit 18, the monitor 2 displays image data ($IQ_1$), image data ($IQ_2$), and the image data (IQ) at the same time as illustrated in FIG. 20A.

Figure 20A:
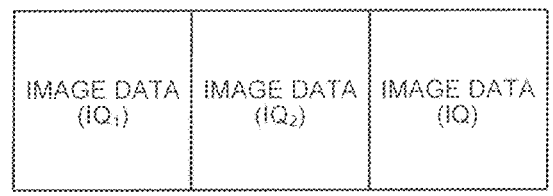
FIGS. 20A, 20B, and 20C are diagrams (2) for explaining the fifth embodiment.

In a display mode exemplified in FIG. 20A, an image interpreter can refer to the image data ($IQ_1$) having high lateral resolution so as to identify a portion where signals deemed to be multiple reflection signals are superimposed. From the image data ($IQ_2$), the image interpreter can refer to a portion corresponding to the portion identified in the image data ($IQ_1$) so as to confirm that the signals deemed to be multiple reflection signals are reduced. By the confirmation, the image interpreter can determine whether the signals are actually reflected signals or multiple reflection signals, thereby proceeding with image diagnosis. Furthermore, the image interpreter can refer to the image data (IQ) to confirm that image quality specific to the image data ($IQ_1$) and image quality specific to the other image data ($IQ_2$) are maintained, or the image qualities are further improved, and proceed with the image diagnosis using the image data (IQ).

Figure 20B:
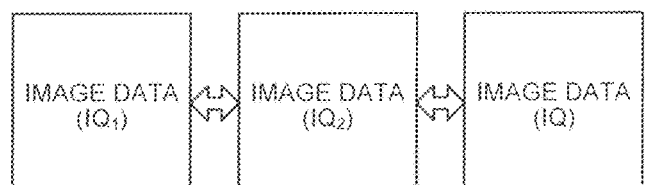
Figure 20C:
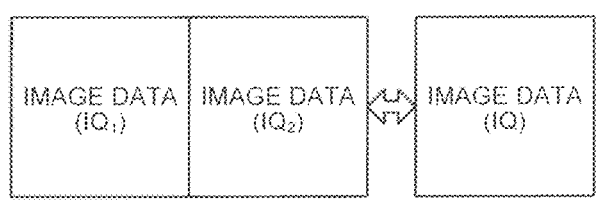

Alternatively, based on the above described reason, the monitor 2 performs display by selectively switching among the image data ($IQ_1$), the image data ($IQ_2$), and the image data (IQ), as illustrated in FIG. 20B, by the control of the control unit 18 that has received an instruction from an image interpreter, for example. Alternatively, as illustrated in FIG. 20C, the monitor 2 performs display by selectively switching between the image data ($IQ_1$) and the image data ($IQ_2$), and the image data (IQ), for example.

In the example described above, the image data for display may include image data generated from a compound signal "$IQ_1 \cdot IQ_2^*$".

Furthermore, in order to enable an image interpreter to identify a change in image data between before and after various processing such as compounding processing and signal processing, the control unit 18 may include difference image data of any combination of pieces of image data constituting the image data group for display, in the image data group for display. Alternatively, the control unit 18 may further include superimposed compound image data obtained by superimposing and compounding any combination of pieces of image data constituting the image data group for display, in the image data group for display.

For example, in "arithmetic processing" illustrated in FIG. 19, the B-mode processing unit 12 generates a differential signal by obtaining a difference between signals and generates B-mode data from the differential signal. Subsequently, the image generating unit 14 generates B-mode image data. For example, the B-mode processing unit 12 generates B-mode data from a differential signal obtained by subtracting "IQ" from "$IQ_1$". In image data generated and displayed from the B-mode data, multiple reflection signals that have been reduced by non-linear processing are mainly drawn.

Alternatively, for example, in "arithmetic processing" illustrated in FIG. 19, the B-mode processing unit 12 generates a superimposed signal by performing superimposing and compounding signals and generates B-mode data from the superimposed signal. Subsequently, the image generating unit 14 generates B-mode image data. For example, the B-mode processing unit 12 generates B-mode data from a superimposed signal obtained by adding "$IQ_1$" and "$IQ_2$" with respect to RBG. In image data generated and displayed from the B-mode data, for example, a signal specific to "$IQ_1$" is drawn in a red color, a signal specific to "$IQ_2$" is drawn in a blue color, and a signal obtained from both "$IQ_1$" and "$IQ_2$" is drawn in a green color.

When generating superimposed compound image data, the control unit 18 may control a change of compounding ratio (superimposing ratio) for superimposing and compounding according to, for example, an instruction from an image interpreter. For example, an image interpreter can easily identify a change in image data according to a change in parameters of the reception apodization by operating a slide bar or a knob that is provided as the input device 3. The above described superimposing processing may be, for example, performed using a superimposed signal obtained by adding "$IQ_1$" and "IQ" with respect to RBG.

As described above, in the fifth embodiment, the monitor 2 outputs, in various display modes, image data that is finally acquired and generated from a compound signal after signal processing, and various image data that can be generated from IQ signals during processing and provide useful information for image diagnosis. In the fifth embodiment, selection of such image data for display and selection of a display mode can be changed arbitrarily according to a demand of an image interpreter. Therefore, the fifth embodiment can improve efficiency of image diagnosis.

Sixth Embodiment

Figure 21:
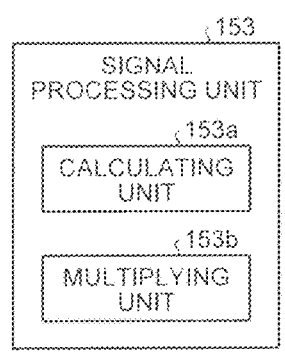
FIG. 21 is a diagram indicating a configuration example of a signal processing unit according to a sixth embodiment.
Figure 22:
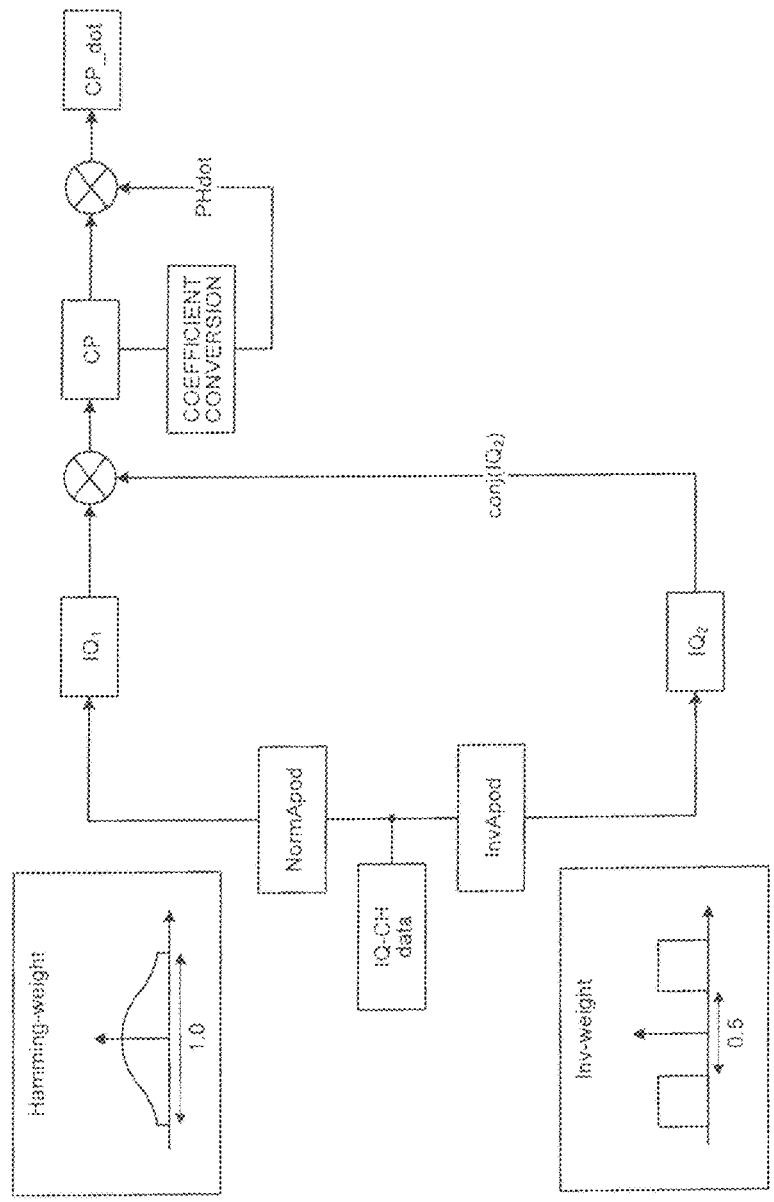
FIG. 22 is a diagram (1) for explaining the signal processing performed in the sixth embodiment.
Figure 23:
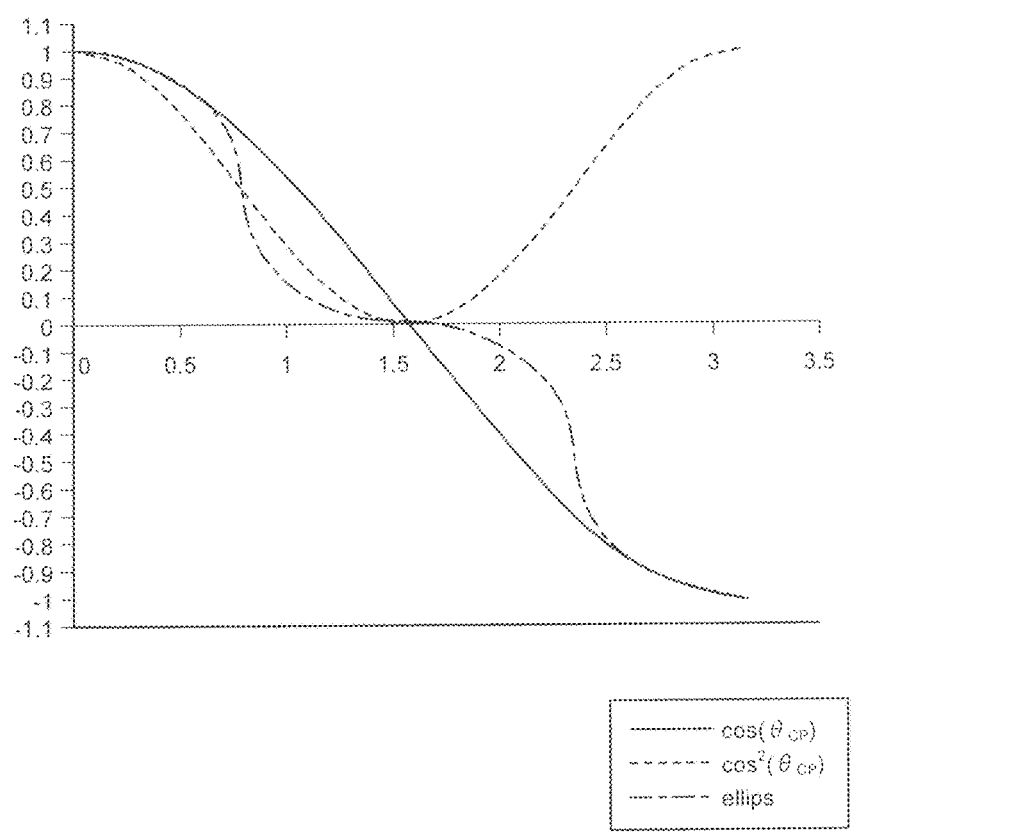
FIG. 23 is a diagram (2) for explaining the signal processing performed in the sixth embodiment.
Figure 24:
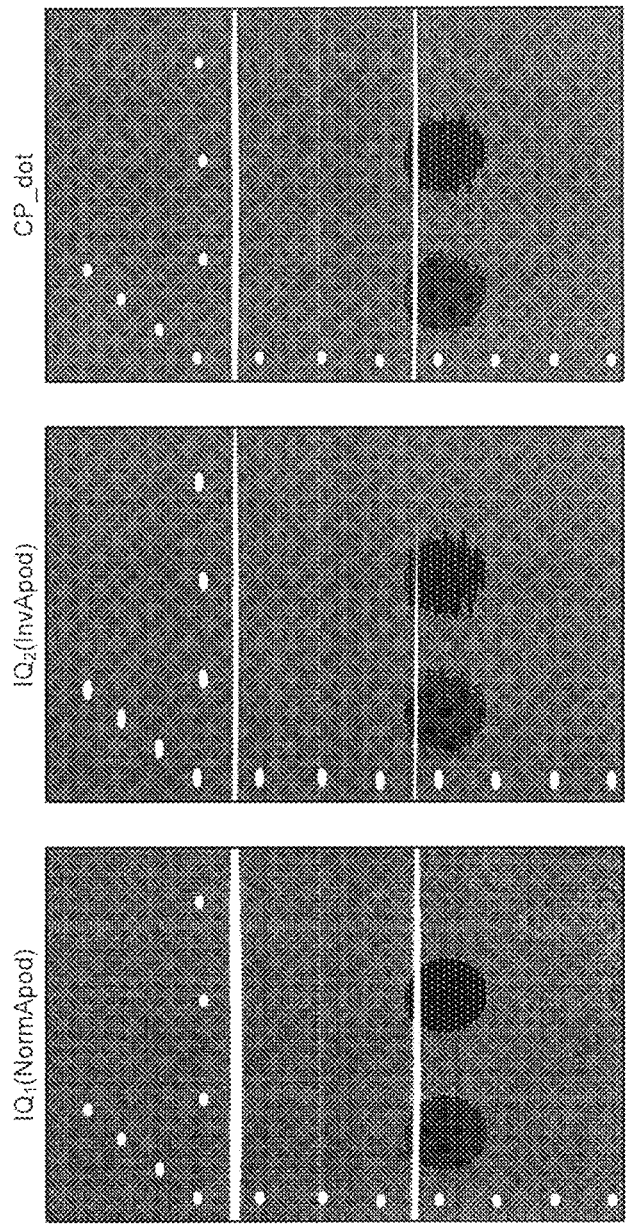
FIG. 24 is a diagram (3) for explaining the signal processing performed in the sixth embodiment.

In the sixth embodiment, one example of signal processing performed by the signal processing unit 153 in parallel processing of reception apodization in a plurality of systems using a plurality of types of aperture functions explained in the second embodiment is explained using FIG. 21 through FIG. 24, for example. FIG. 21 is a diagram indicating a configuration example of a signal processing unit according to the sixth embodiment. FIG. 22 through FIG. 24 are diagrams for explaining signal processing performed in the sixth embodiment.

In the sixth embodiment, as the "parallel processing of reception beam forming in a plurality of systems" explained in the second embodiment, parallel processing of reception beam forming in two systems using two aperture functions having different weighting patterns is performed. For example, two aperture functions having different weighting patterns are the normal aperture function of the hamming window and the inverse aperture function in which the center portion is zero. The parallel processing of reception beam forming in two systems is parallel processing of fixed normal apodization and fixed inverse apodization. However, the processing explained below is applicable to a case in which, as a normal aperture function and an inverse aperture function, various normal aperture functions and inverse aperture functions explained in the second embodiment are used.

The ultrasonography apparatus according to the sixth embodiment is configured similarly to the ultrasonography apparatus illustrated in FIG. 1. The signal processing unit 153 according to the sixth embodiment, however, includes a calculating unit 153a and a multiplying unit 153b as exemplified in FIG. 21.

The acquiring unit 151 according to the sixth embodiment acquires two IQ signals corresponding to respective two aperture functions. The compounding unit 152 according to the sixth embodiment generates a compound signal from the two IQ signals by multiplication processing that is non-linear processing.

"$IQ=IQ_1 \cdot IQ_2^*$" expressed by Equation 6 and Equation 9 is power of "$IQ_1$" or "$IQ_2$" if "$IQ_1=IQ_2$". In the present embodiment and the subsequent embodiments, a compound signal "IQ" is defined as CP (Cross-Power) as expressed by Equation 23 below.

$$CP = IQ = IQ_1 \cdot IQ_2^* \tag{23}$$

In the present embodiment and the subsequent embodiments, a phase (phase angle) of CP that is the compound signal, specifically, "$\theta_{IQ} = \theta_1 - \theta_2$" in Equation 11 that is a phase difference between "$IQ_1$" and "$IQ_2$", is defined as "$\theta_{CP}$" as expressed by Equation 24 below.

$$\theta_{CP} = \theta_1 - \theta_2 \tag{24}$$

By using such definitions, the signal processing unit 153 performs signal processing on the compound signal CP. That is, in the sixth embodiment, the calculating unit 153a illustrated in FIG. 21 calculates one coefficient or a plurality of types of coefficients from the phase information included in the compound signal CP. Specifically, a coefficient calculated by the calculating unit 153a from the compound signal CP has a value that increases or decreases depending on the magnitude of correlation between two IQ signals detected from the phase information included in the compound signal CP.

More specifically, a coefficient calculated by the calculating unit 153a from the compound signal CP has a value that changes according to the phase angle "$\theta_{CP}$" indicating a phase difference of two IQ signals detected from the phase term of the compound signal CP. The coefficient is zero when the phase angle indicates that the two IQ signals are perpendicular to each other. The absolute value of the coefficient is 1 when the phase angle indicates that the two IQ signals are in parallel. For example, a coefficient calculated by the calculating unit 153a from the compound signal CP is a cosine value of the phase angle "$\theta_{CP}$".

In the sixth embodiment, the multiplying unit 153b illustrated in FIG. 21 obtains a signal by multiplying the compound signal CP by one coefficient or any one of the coefficients, and outputs the signal as a compound signal subjected to signal processing.

The above described processing is explained using FIG. 22. First, by the control of the control unit 18, the transceiving unit 11 performs ultrasonic wave transmission/reception at each scan line forming a scanning range. To the adding unit of the transceiving unit 11, a reception signal ("IQ-CH data" illustrated in FIG. 22) of each transducer element to which required delay is given by the reception delaying unit is input as an input signal. "IQ-CH data" indicates a data string of IQ signals. The adding unit separates the input signal "IQ-CH data" into two systems as illustrated in FIG. 22. The adding unit then performs phasing addition by performing weighting using the normal aperture function of the hamming window as normal apodization (NormApod) in one system. The above processing outputs "$IQ_1$" to the acquiring unit 151. The adding unit performs phasing addition by performing weighting using the inverse aperture function in which the center portion is zero as inverse apodization (InvApod) in the other system. The above processing outputs "$IQ_2$" to the acquiring unit 151.

In the sixth embodiment, it is preferable that at least one of the two signals "$IQ_i$" and "$IQ_2$" be a signal for which a non-linear component is extracted. A signal for which a non-linear component is extracted means a signal from which a linear component is substantially removed and in which a non-linear component remains. Specifically, the inverse apodization using the inverse aperture function in which the center portion is zero has high side lobes of reception beams, and it is preferable that an IQ signal for which a tissue harmonic component in which mixing of an artifact component by transmission beams is few is extracted, be used as "$IQ_2$".

For an IQ signal "$IQ_1$" in the normal apodization, a signal of a basic wave component that is suitable for imaging with high sensitivity even to a deep portion may be used, or a signal of a tissue harmonic component (a non-linear component of a tissue) having small side lobes of transmission beams, and in which mixing of an artifact component is few may be used. In terms of simplifying a configuration of the transceiving unit 11, it is advantageous to regard, in both the normal apodization and the inverse apodization, "IQ-CH data" illustrated in FIG. 22 as a data string of IQ signals for which a tissue harmonic component is extracted. In such a case, for example, the transceiving unit 11 performs ultrasonic wave transmission/reception by the PM method described above to acquire a signal for which a non-linear component is extracted, and performs the normal apodization and the inverse apodization.

The compounding unit 152 multiplies "$IQ_1$" by a complex conjugate (conj($IQ_2$) illustrated in FIG. 22) of "$IQ_2$" so as to output CP. The calculating unit 153a then calculates a coefficient from CP. Specifically, the calculating unit 153a converts a phase "$\theta_{CP}$" of CP to a coefficient "PHdot". The multiplying unit 153b then multiplies CP by "PHdot". Output data from the multiplying unit 153b is subjected to processing by the B-mode processing unit 12 and the image generating unit 14, and is output as image data "CP_dot".

As one example of converting the phase "$\theta_{CP}$" of CP to the coefficient "PHdot", it is preferable to use "$\cos(\theta_{CP})$" as described above.

CP can be defined as an input IQ signal at one point. "$\cos(\theta_{CP})$" as a coefficient value can be calculated by the four arithmetic operations and a square root of the components of CP, thereby enabling a high-speed arithmetic operation. "$\cos(\theta_{CP})$" corresponds to a correlation coefficient between "$IQ_1$" and "$IQ_2$". When the absolute value of the correlation efficient is large, an output is enhanced. When the correlation efficient is small, an output is reduced.

The above description is explained below. Reconsideration of the meaning of CP on a complex plane indicates that, when "$\theta_{CP}$" that is a phase difference between "$IQ_1$" and "$IQ_2$" is "zero" or "$2\pi$", CP presents only on a real axis and is the signal power itself of "$IQ_1$" or "$IQ_2$". On the other hand, when the phase difference "$\theta_{CP}$" is "$+\pi/2$" or "$-\pi/2$", CP presents only on an imaginary axis. When the phase difference "$\theta_{CP}$" is "$\pi$", CP is a value on a real axis having a minus sign. When the phase difference is other value than the above values, CP has both a real number component and an imaginary number component. In any of the cases, a physical dimension is a dimension of power.

Here, calculation of a ratio between the absolute value of CP and a real part (Re[CP]) of CP provides a value "$\cos(\theta_{CP})$" as expressed by Equation 25 below. On the other hand, calculation of a ratio between the absolute value of CP and an imaginary part (Im[CP]) of CP provides a value "$\sin(\theta_{CP})$" as expressed by Equation 25 below. In particular, when "$IQ_1$" and "$IQ_2$" are regarded as vectors, "$\cos(\theta_{CP})$" is equivalent to an inner product of both vectors. This inner product is a value that means a correlation coefficient between "$IQ_1$" and "$IQ_2$".

$$\left. \begin{array}{l} \dfrac{\text{Re}[CP]}{|CP|} = \dfrac{A_i B_i + A_q B_q}{|IQ_1||IQ_2|} = \dfrac{A_i B_i + A_q B_q}{\sqrt{A_i^2 + A_q^2}\sqrt{B_i^2 + B_q^2}} = \cos(\theta_{CP}) \\[1em] \dfrac{\text{Im}[CP]}{|CP|} = \dfrac{A_q B_i - A_i B_q}{|IQ_1||IQ_2|} = \dfrac{A_q B_i - A_i B_q}{\sqrt{A_i^2 + A_q^2}\sqrt{B_i^2 + B_q^2}} = \sin(\theta_{CP}) \end{array} \right\} \quad (25)$$

FIG. 23 illustrates a graph of "$\cos(\theta_{CP})$" with a solid line. As illustrated in FIG. 23, when "$\theta_{CP}$" is "zero" or "$2\pi$", the absolute value of "$\cos(\theta_{CP})$" is "1". When "$\theta_{CP}$" is "$\pi$", the absolute value of "$\cos(\theta_{CP})$" is "zero". Therefore, by multiplying CP by "$\cos(\theta_{CP})$", a signal can be obtained in which components in the center of a main beam having a matching phase remain, components near a side lobe having a low correlation are reduced, and multiple reflection components having a low correlation are also reduced.

FIG. 24 illustrates a result of imaging a phantom covered with water on a surface thereof by THI to acquire an image including a specular multiple reflection component. "$IQ_1$ (NormApod)" indicated in the left figure in FIG. 24 is B-mode image data of a tissue harmonic component acquired by the normal apodization. "$IQ_2$(InvApod)" indicated in the center figure in FIG. 24 is B-mode image data of a tissue harmonic component acquired by the inverse apodization. "CP_dot" indicated in the right figure in FIG. 24 is image data that is output by the processing exemplified in FIG. 22.

In "$IQ_1$(NormApod)", a single multiple reflection component between a surface of the phantom and a probe and a double multiple reflection component between the surface of the phantom and the probe are observed. Furthermore, it is observed that the double multiple reflection component is superimposed on black void portions indicating cysts. On the other hand, in "CP_dot", not only the double multiple reflection component superimposed on the black void portions of cysts observed in "$IQ_1$(NormApod)" but also the single multiple reflection component superimposed on a tissue having high brightness is reduced. Furthermore, when focusing on a wire in "CP_dot", it is observed that the lateral resolution is more improved than that of "$IQ_2$(InvApod)" and is equivalent to that of "$IQ_1$(NormApod)".

As described above, in the sixth embodiment, for example, by multiplying CP by "$\cos(\theta_{CP})$", a signal can be obtained in which components in the center of a main beam having a matching phase remain and components near a side lobe having a low correlation are reduced. Thus, the lateral resolution is improved and a moire can be reduced compared to the case of simply performing the aperture compounding processing. Furthermore, by multiplying CP by "$\cos(\theta_{CP})$", a signal can be obtained in which multiple reflection components having a low correlation are also reduced, thereby enabling a reduction of multiple reflection components. Moreover, a coefficient multiplied by the compound signal CP in the sixth embodiment is based on phase information. Therefore, even when a signal component originated in a tissue and a multiple reflection component are superimposed on each other, the effect of reducing multiple reflection is higher than that of conventional compounding processing.

In addition, the processing explained in the sixth embodiment involves smaller amounts of arithmetic operation for acquiring CP and "$\cos(\theta_{CP})$", and thus can be performed in real-time. Furthermore, in the sixth embodiment, using an IQ signal of a tissue harmonic component as a compounding-source signal can reduce the influence of an increase in a side lobe due to inverse apodization, for example. Accordingly, in the sixth embodiment, a high quality image in which multiple reflection is reduced, and the lateral resolution and the sensitivity are maintained can be acquired.

In the example described above, a case is explained in which "$\cos(\theta_{CP})$" having a physical meaning equivalent to an inner product or a correlation coefficient, as an example of conversion to a coefficient according to the phase "$\theta_{CP}$" of CP. As described above, however, considering the meaning of a phase difference on a complex plane, there are other coefficient converting methods that provide similar effects.

Specifically, a coefficient having a characteristic in which a weight is large when both vectors are parallel and the weight is zero when the vectors are perpendicular to each other, is applicable to the above described processing. As a modification of such a coefficient, FIG. 23 illustrates "$\cos^2(\theta_{CP})$" with a dashed line and a function "ellips" based on an ellipse having "$\theta_{CP}$" and an output weight as two variables with an alternate long and short dashed line. "ellips" is a function that uses a boundary condition in which "$\theta_{CP}$" is "$\pi/2, \pi, 3\pi/2$".

"$\cos^2(\theta_{CP})$" and "ellips" have characteristics that reduce a weight used when both vectors are perpendicular to each other to a smaller value than that in the case of the inner product "$\cos(\theta_{CP})$", thereby reducing an output when there is no correlation.

When multiplying CP by any one of the three types of coefficients, it is preferable that gain correction be performed. If "$\cos(\theta_{CP})$" is multiplied, compared to the case in which a coefficient "1" is always multiplied regardless of ($\theta_{CP}$), an integration value of the coefficient in the dimension of power is an area value surrounded by "$\cos(\theta_{CP})$" and the X axis in FIG. 23, which is ½. Thus, giving "+3 dB" to a multiplication result can equalize the result with a gain obtained when "$\cos(\theta_{CP})$" is not multiplied. By performing such gain correction, "CP_dot" can be displayed such that normal B-mode image data and the gain on appearance are equivalent.

Although "$\cos^2(\theta_{CP})$" outputs a coefficient not having a minus value, a final image is output after obtaining an amplitude component (absolute value component) of a signal, and thus "$\cos^2(\theta_{CP})$" is an applicable coefficient to the above processing. The above description is equivalent to the following: when "$\cos(\theta_{CP})$" is used, "$IQ_1$" and "$IQ_2$" are inverse to each other when "$\theta_{CP}=\pi$" and a coefficient value is a minus value, while obtaining an absolute value after coefficient multiplication enhances the signals with each other as a result.

Using "$\sin(\theta_{CP})$" as a coefficient emphasizes a low correlation. In this case, subtracting a signal obtained by multiplying CP by "$\sin(\theta_{CP})$" from CP can also provide an effect similar to that in the case of using "$\cos(\theta_{CP})$". This arithmetic processing is expressed by "$CP*(1-\sin(\theta_{CP}))$", and thus is equivalent to processing that multiplies CP by a coefficient "$1-\sin(\theta_{CP})$".

In the sixth embodiment, as described above, various aperture functions (for example, a shifted inverse aperture-function) explained in the second embodiment as the normal aperture function and the inverse aperture function are applicable. Furthermore, in the sixth embodiment, for example, the two aperture functions may be the normal aperture function of the rectangular window and the normal aperture function of the hamming window. In this example, image data in which effects of both a narrow main beam and reduced side lobes are maintained can be obtained.

Moreover, in the sixth embodiment, the two aperture functions may be an aperture function having a weighting pattern in which a weight is increased from one end portion to the other end portion of the reception aperture, and an aperture function having a weighting pattern in which a weight is increased from the other end portion to the one end portion of the reception aperture. That is, in the sixth embodiment, a right aperture function having a larger weight on the right side of the reception aperture and a left aperture function having a larger weight on the left side of the reception aperture may be used. In this example, a signal component having a high correlation when viewed from either the aperture on the right side or the left side is emphasized. Thus, image data in which speckle noise is reliably reduced can be obtained. The right aperture function and the left aperture function can be included in the aperture functions used in the processing explained in the second embodiment.

Seventh Embodiment

Figure 25:
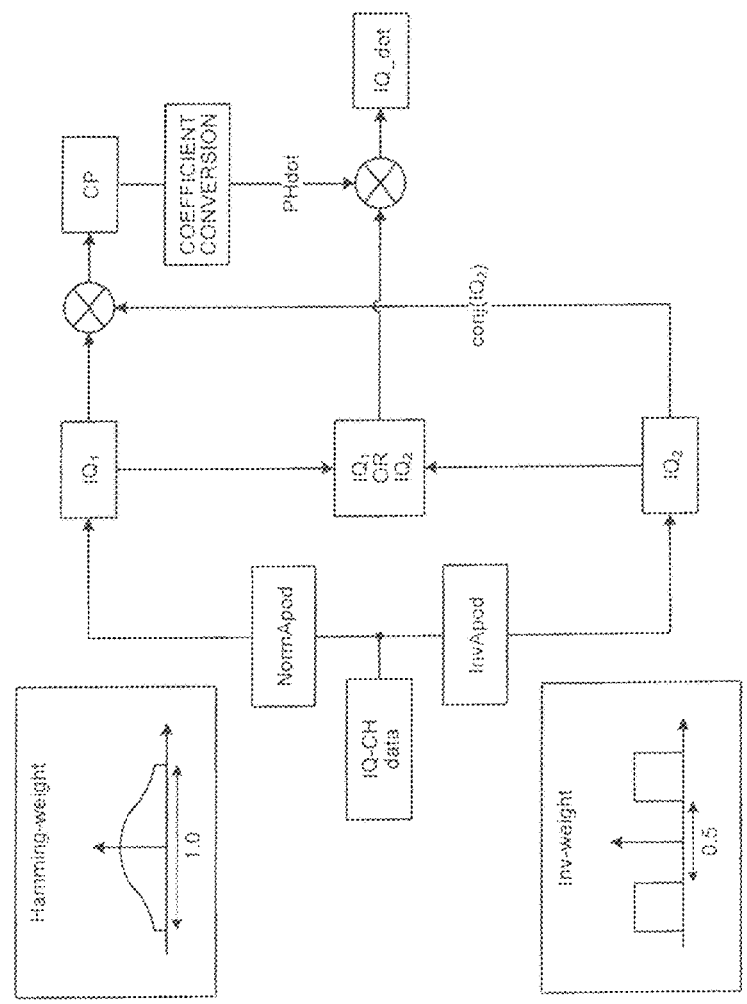
FIG. 25 is a diagram (1) for explaining a seventh embodiment.
Figure 26:
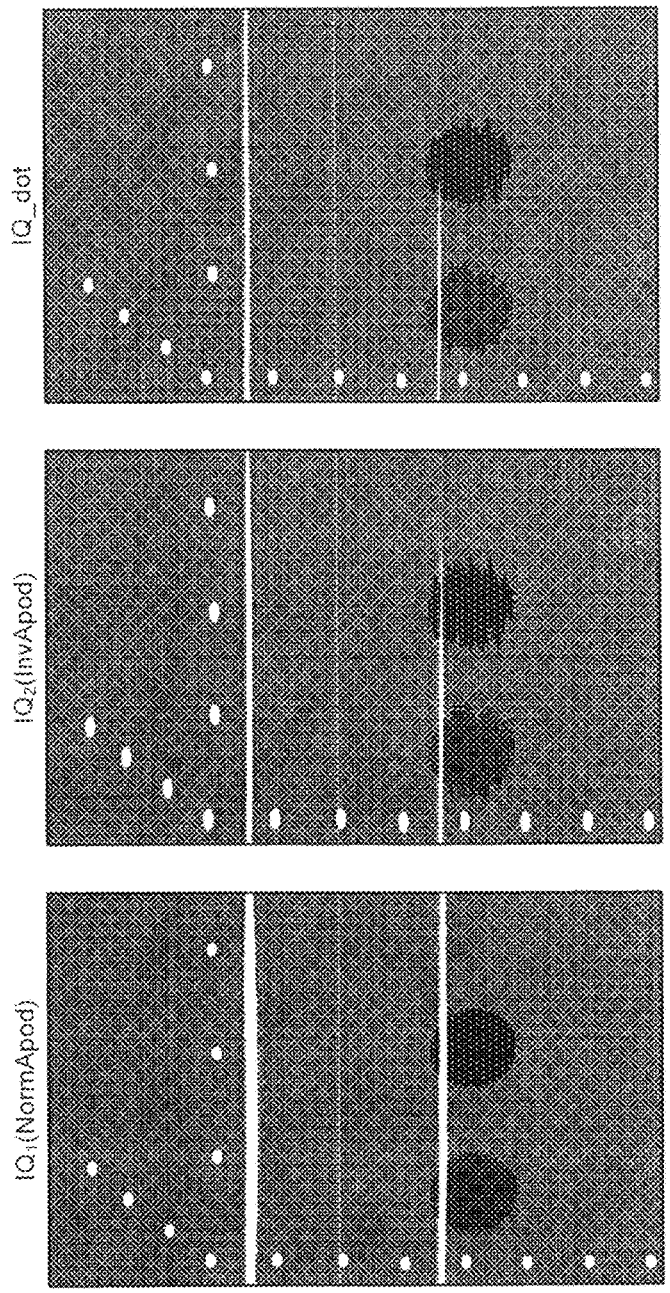
FIG. 26 is a diagram (2) for explaining the seventh embodiment.

In the sixth embodiment, a case is explained in which a compound signal CP is multiplied by a coefficient calculated from the phase "$\theta_{CP}$" of the compound signal CP so as to obtain final output image data. In the seventh embodiment, a case is explained in which an IQ signal that is a compounding-source of the compound signal CP is multiplied by a coefficient calculated from the phase "$\theta_{CP}$" of the compound signal CP so as to obtain final output image data, using FIG. 25 and FIG. 26, for example. FIG. 25 and FIG. 26 are diagrams for explaining the seventh embodiment.

The signal processing unit 153 according to the seventh embodiment includes the calculating unit 153a and the multiplying unit 153b similarly to the signal processing unit 153 according to the sixth embodiment. The calculating unit 153a according to the seventh embodiment calculates one coefficient or a plurality of types of coefficients from the phase information "$\theta_{CP}$" included in the compound signal CP, similarly to the sixth embodiment. Coefficients calculated by the calculating unit 153a include "$\cos(\theta_{CP})$", "$\cos^2(\theta_{CP})$", and "ellips" described above, for example.

The multiplying unit 153b according to the seventh embodiment obtains a signal by multiplying one of two IQ signals by one coefficient or any one of the coefficients, and outputs the resultant signal as a compound signal subjected to signal processing.

The above described processing is explained using FIG. 25. In FIG. 25, processing for obtaining "$IQ_1$" and "$IQ_2$", processing for obtaining CP by multiplying "$IQ_1$" by "$IQ_2$", and processing for obtaining a coefficient "PHdot" by converting a phase angle of CP are the same as those illustrated in FIG. 22, and thus the explanation thereof is omitted. The description in the sixth embodiment is also applicable to the seventh embodiment except that the processing by the multiplying unit 153b is different.

The multiplying unit 153b multiplies "$IQ_1$" or "$IQ_2$" by "PHdot" as illustrated in FIG. 25. Output data from the multiplying unit 153b is subjected to processing by the B-mode processing unit 12 and the image generating unit 14, and is output as image data "IQ_dot". For example, the multiplying unit 153b multiplies "$IQ_2$" by "$\cos(\theta_{CP})$" and outputs the resultant signal to B-mode processing unit 12.

"$IQ_1$(NormApod)" indicated in the left figure in FIG. 26 is the same image data as that indicated in the left figure in FIG. 24, and "$IQ_2$(InvApod)" indicated in the center figure in FIG. 26 is the same image data as that indicated in the center figure in FIG. 24. "IQ_dot" indicated in the right figure in FIG. 26 is image data that is generated from a signal obtained by multiplying "IQ$_2$" by "cos(θ$_{CP}$)".

Because "IQ$_2$" obtained by the inverse apodization that provides the least multiple reflection components is used as a base signal, multiple reflection components are sufficiently small in "IQ_dot". Furthermore, in "IQ_dot", it is observed that the lateral resolution is more improved than that of "IQ$_2$(InvApod)". In "IQ_dot", however, an aspect of the speckle pattern of tissue largely changes compared to that of "IQ$_1$(NormApod)", and is close to the pattern of "IQ$_2$ (InvApod)". This is because, at the portions in the tissue having the speckle pattern, the phase difference between "IQ$_1$" and "IQ$_2$" is statistically small, and therefore "IQ$_2$" obtained by the inverse apodization is output as it is.

As described above, in the seventh embodiment, by multiplying the IQ signal obtained by the inverse apodization of a compounding-source, by the coefficient calculated from the compound signal CP, a high quality image in which multiple reflection is reduced and the lateral resolution is maintained can be acquired. The seventh embodiment is applicable to a case in which the IQ signal obtained by the normal apodization of a compounding-source is multiplied by the coefficient calculated from the compound signal CP. In the seventh embodiment, any one of "cos(θ$_{CP}$)", "cos$^2$(θ$_{CP}$)" and "ellips" can be used as a coefficient.

In the seventh embodiment, the multiplying unit 153b may obtain two signals by multiplying two compounding-source IQ signals by two respective coefficients among the coefficients, and compound the two signals to output a signal. For example, the multiplying unit 153b may perform signal averaging on a signal obtained by multiplying "IQ$_1$" by "cos(θ$_{CP}$)" and a signal obtained by multiplying "IQ$_2$" by "cos$^2$(θ$_{CP}$)", and output the resultant signal to B-mode processing unit 12. The multiplying unit 153b may perform signal averaging on two signals obtained by multiplying "IQ$_1$" and "IQ$_2$" by the same coefficient, and output the resultant signal to B-mode processing unit 12.

Eighth Embodiment

Figure 27:
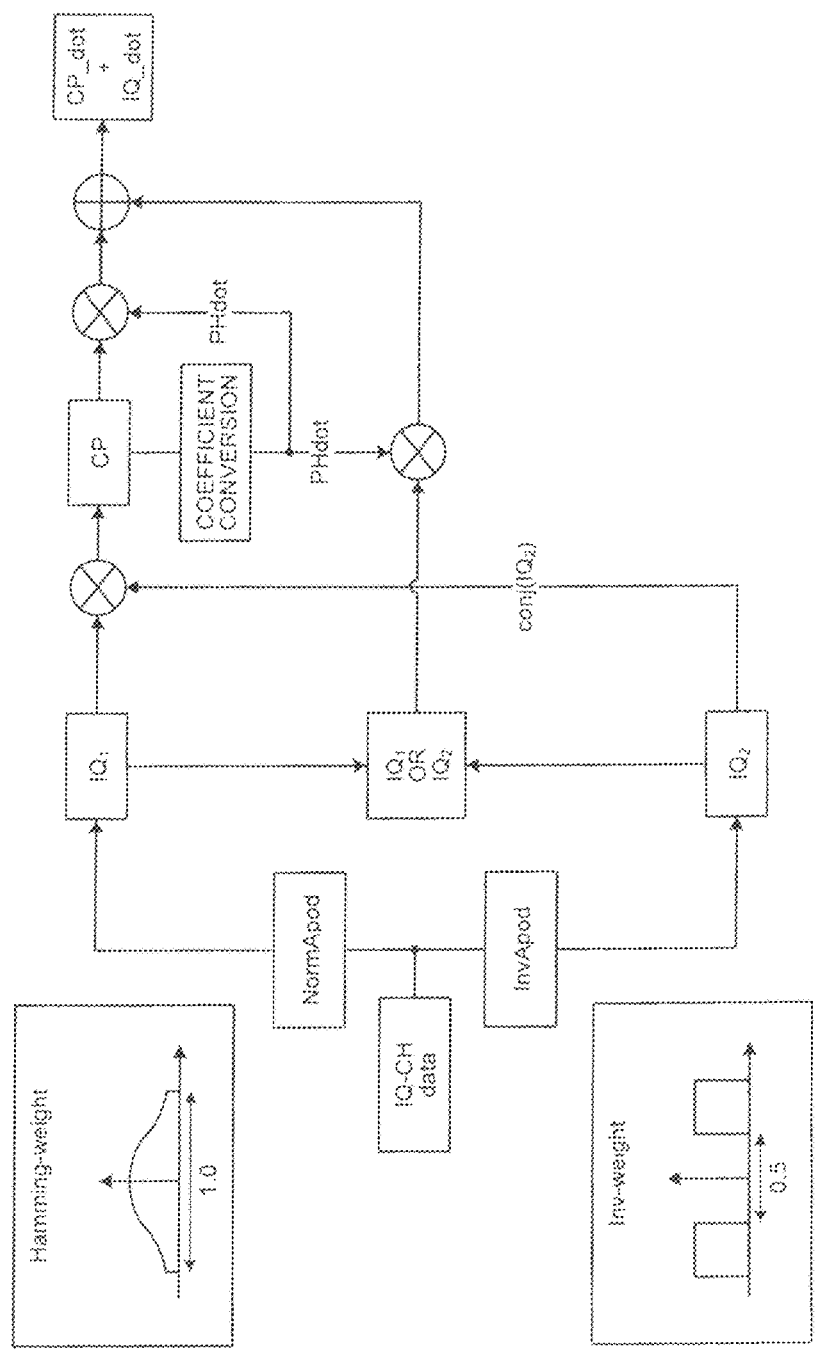
FIG. 27 is a diagram (1) for explaining an eighth embodiment.
Figure 28:
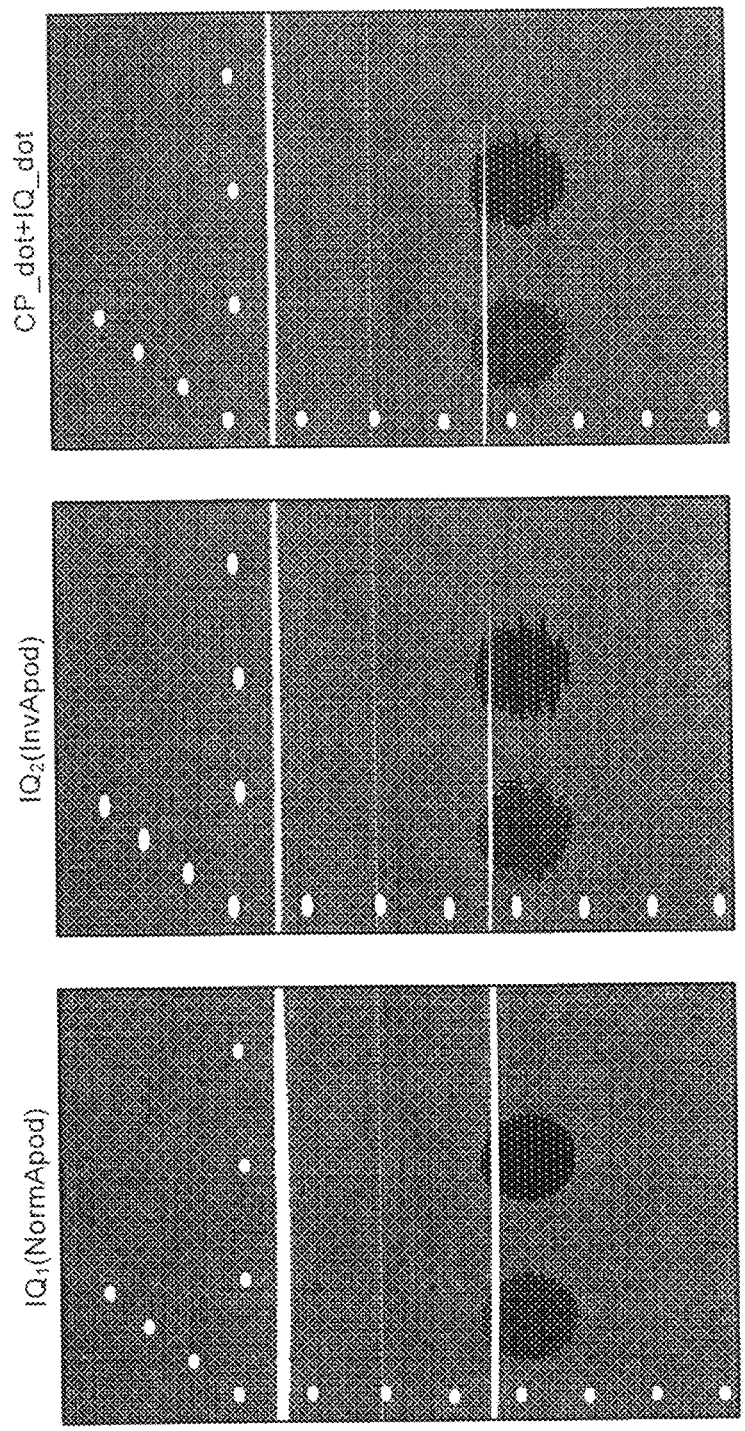
FIG. 28 is a diagram (2) for explaining the eighth embodiment.

In the eighth embodiment, a case is explained in which the compound signal CP and an IQ signal that is a compounding-source of the compound signal CP are multiplied by a coefficient calculated from the phase "θ$_{CP}$" of the compound signal CP and resultant two signals are compounded by incoherent addition so as to obtain final output image data, using FIG. 27 and FIG. 28, for example. FIG. 27 and FIG. 28 are diagrams for explaining the eighth embodiment.

The signal processing unit 153 according to the eighth embodiment includes the calculating unit 153a and the multiplying unit 153b similarly to the signal processing unit 153 according to the sixth embodiment and the seventh embodiment. The calculating unit 153a according to the eighth embodiment calculates one coefficient or a plurality of types of coefficients from the phase information "θ$_{CP}$" included in the compound signal CP, similarly to the sixth embodiment and the seventh embodiment. Coefficients calculated by the calculating unit 153a include "cos(θ$_{CP}$)", "cos$^2$(θ$_{CP}$)", and "ellips" described above, for example.

The multiplying unit 153b according to the eighth embodiment obtains a signal by multiplying the compound signal CP by one coefficient or any one of the coefficients and a signal by multiplying one of two IQ signals by one coefficient or any one of the coefficients, compounds the two signals, and outputs the resultant signal as the compound signal subjected to signal processing.

The above described processing is explained using FIG. 27. In FIG. 27, processing for obtaining "IQ1" and "IQ2", processing for obtaining CP by multiplying "IQ1" by "IQ2", and processing for obtaining coefficient "PHdot" by converting a phase angle of CP are the same as those illustrated in FIG. 22, and thus the explanation thereof is omitted. The description in the sixth embodiment is also applicable to the eighth embodiment except that the processing by the multiplying unit 153b is different.

The multiplying unit 153b multiplies "CP" by "PHdot" as illustrated in FIG. 27. From the signal obtained by multiplying "CP" by "PHdot", the multiplying unit 153b obtains an amplitude signal or a signal obtained by performing logarithm compression on the amplitude signal, by the same processing as that performed by the B-mode processing unit 12. The multiplying unit 153b also multiplies "IQ$_1$" or "IQ$_2$" by "PHdot" as illustrated in FIG. 27. From the signal obtained by multiplying "IQ$_1$" or "IQ$_2$" by "PHdot", the multiplying unit 153b obtains an amplitude signal or a signal obtained by performing logarithm compression on the amplitude signal, by the same processing as that performed by the B-mode processing unit 12. The multiplying unit 153b then compounds the two signals. Output data from the multiplying unit 153b is subjected to processing by the image generating unit 14, or processing by the B-mode processing unit 12 and the image generating unit 14, and is output as image data "CP_dot+IQ_dot".

For example, the multiplying unit 153b compounds a signal obtained by multiplying "CP" by "cos(θ$_{CP}$)" and a signal obtained by multiplying "IQ2" by "cos(θ$_{CP}$)", and outputs the resultant signal.

"IQ$_1$(NormApod)" indicated in the left figure in FIG. 28 is the same image data as that indicated in the left figure in FIG. 24, and "IQ$_2$(InvApod)" indicated in the center figure in FIG. 28 is the same image data as that indicated in the center figure in FIG. 24. "CP_dot+IQ_dot" indicated in the right figure in FIG. 28 is image data that is generated from a signal obtained by compounding a signal obtained by multiplying "CP" by "cos(θ$_{CP}$)" and a signal obtained by multiplying "IQ$_2$" by "cos(θ$_{CP}$)".

The output image data "CP_dot+IQ_dot" is image data obtained by compounding the output image data "CP_dot" explained in the sixth embodiment and the output image data "IQ_dot" explained in the seventh embodiment. The eighth embodiment aims to obtain an output that is more natural to an image interpreter by approximating the aspect of a speckle pattern to that of "IQ$_1$(NormApod)" than "IQ_dot" while enhancing the multiple reflection reducing effect more than that of "CP_dot". "CP_dot+IQ_dot" illustrated in FIG. 28 indicates that the above expected result has been achieved.

As described above, in the eighth embodiment, by multiplying the compound signal and the IQ signal obtained by the inverse apodization of a compounding-source by the coefficient calculated from the compound signal CP, and performing incoherent addition on resultant signals, a high quality image in which multiple reflection is reduced and the lateral resolution is maintained can be acquired.

The eighth embodiment may be a case in which the IQ signal obtained by the normal apodization of a compounding-source is multiplied by a coefficient. Furthermore, in the eighth embodiment, the coefficient multiplied by the compound signal and the coefficient multiplied by one of the two IQ signals may be coefficients of different type.

Moreover, in the eighth embodiment, the multiplying unit 153b may obtain a signal by multiplying the compound signal by one coefficient or any one of the coefficients and a signal by multiplying two IQ signals by two respective coefficients among the coefficients, compound the two signals by incoherent addition, and output the resultant signal as the compound signal subjected to signal processing. In such a case, the multiplying unit 153b may use different coefficients for the coefficient for CP, the coefficient for $IQ_1$, and the coefficient for $IQ_2$, or use the same coefficient for two coefficients multiplied by two signals among the three signals "CP, $IQ_1$, and $IQ_2$".

The three processing explained in the sixth embodiment, the seventh embodiment, and the eighth embodiment described above, respectively, are preferably configured such that optimal processing is selectable from, for example, a preset menu by an image interpreter according to a use in consideration of the naturalness of a speckle pattern of image data obtained finally and trade-offs relative to the multiple reflection signal reducing effect.

Ninth Embodiment

Figure 29:
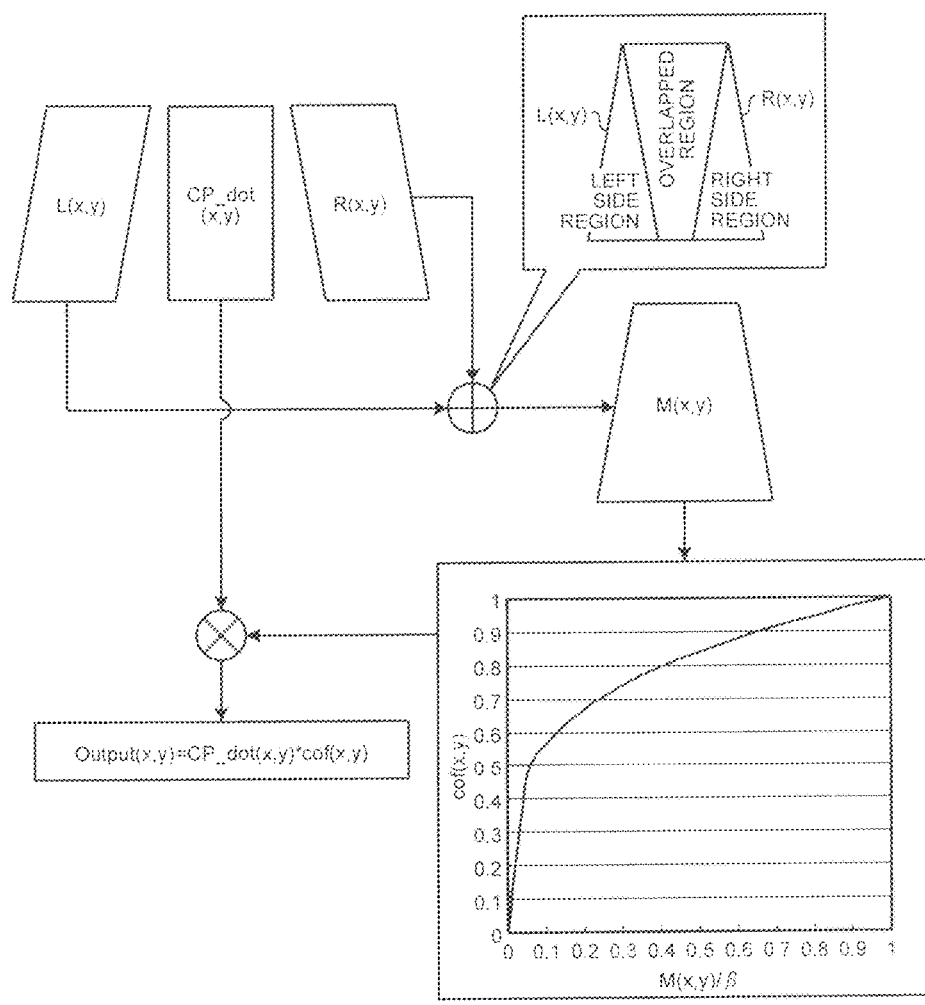
FIG. 29 is a diagram for explaining a ninth embodiment.

In the ninth embodiment, a case is explained in which the multiple reflection reducing effect is further enhanced by additionally using a coefficient distribution that is acquired independently of the coefficients acquired from the compound signal CP explained in the sixth embodiment, the seventh embodiment, and the eighth embodiment, using FIG. 29. FIG. 29 is a diagram for explaining the ninth embodiment.

The acquiring unit 151 according to the ninth embodiment acquires a reception signal group that is constituted of a plurality of reception signals with various deflection angles other than that in a certain direction used to acquire two IQ signals. The calculating unit 153a according to the ninth embodiment calculates a coefficient from the two IQ signals, and further calculates a coefficient distribution using at least one reception signal from the reception signal group. The multiplying unit 153b according to the ninth embodiment performs multiplication processing using the coefficient and the coefficient distribution. The control unit 18 according to the ninth embodiment causes the monitor 2 to display image data based on the signal output by the multiplying unit 153b.

Specifically, the acquiring unit 151 further acquires an image data group that is constituted of a plurality of pieces of ultrasonic image data with various deflection angles generated by ultrasonic scanning in which the deflection angles in ultrasonic wave transmission/reception are varied among frames. The deflection angles include the deflection angle in the certain direction (0 degrees) used to acquire the two IQ signals. The calculating unit 153a further calculates a coefficient distribution "cof(x,y)" using at least one piece of the ultrasonic image data with a deflection angle in a direction other than the certain direction, from the image data group. Subsequently, the multiplying unit 153b multiplies, from the image data group, ultrasonic image data with the deflection angle in the certain direction, or image data that is obtained by compounding ultrasonic image data with respective deflection angles in a plurality of directions including the certain direction, by the coefficient and the coefficient distribution.

That is, in the ninth embodiment, ultrasonic scanning in which the deflection angle is varied per frame (per image) explained using FIG. 3 is performed. For example, by the control of the control unit 18, the transceiving unit 11 causes the ultrasound probe 1 to perform ultrasonic wave transmission/reception in three directions (deflection angles: 0 degrees, +θ degrees, −θ degrees) in a frame unit. Thus, three pieces of B-mode image data with different deflection angles are generated by the image generating unit 14. Processing explained below is applicable to a signal at any stage as long as the signal has been subjected to phase detection by the B-mode processing unit 12.

The certain direction described above is the direction of the deflection angle of "0 degrees". The direction of the deflection angle of "0 degrees" is, for example, a direction to acquire "$IQ_1$, $IQ_2$", and is a direction used to acquire "CP_dot" explained in the sixth embodiment. "L(x,y)" and "R(x,y)" illustrated in FIG. 29 are left-deflected image data and right-deflected image data, respectively, in which a multiple reflection component is reduced by inclined transmission and reception. Moreover, "CP_dot(x,y)" illustrated in FIG. 29 is B-mode image data of the direction of the deflection angle of "0 degrees", and is "CP_dot" illustrated in FIG. 24 of the sixth embodiment. "(x,y)" indicates a position of each pixel constituting image data.

In the ninth embodiment, image data that visualizes a compound signal CP is multiplied by a coefficient calculated according to a phase difference of CP, and a coefficient distribution to be explained later. Such processing is substantially equivalent to processing that multiplies "CP_dot (x,y)" by a coefficient distribution "cof(x,y)".

Therefore, FIG. 29 illustrates a case in which the calculating unit 153a calculates the coefficient distribution with "L(x,y)" and "R(x,y)" as subjects of processing, and the multiplying unit 153b handles "CP_dot(x,y)" as a subject of multiplication of the coefficient distribution. As for "L(x,y)" and "R(x,y)" that are the input data to calculate the coefficient distribution, selecting data in which occurrence of multiple reflection decreases at a black void portion such as a cyst described above is effective. A condition under which "L(x,y)" and "R(x,y)" are acquired is selectable from among three cases. This is described in detail later.

First, the calculating unit 153a acquires mean image data "M(x,y)" of "L(x,y)" and "R(x,y)" as illustrated in FIG. 29. Specifically, the calculating unit 153a acquires "M(x,y)" by Equation 26 below.

$$\begin{aligned} M(x, y) &= (L(x, y) + R(x, y))/2 \quad \text{(Overlapped region)} \\ &= L(x, y) \quad \text{(Left side region)} \\ &= R(x, y) \quad \text{(Right side region)} \end{aligned} \quad (26)$$

As illustrated in FIG. 29, positioning "L(x,y)" and "R(x,y)", there are an overlapped region that is a region in which "L(x,y)" and "R(x,y)" are overlapped, a left side region other than the overlapped region in "L(x,y)", and a right side region other than the overlapped region in "R(x,y)". Equation 26 above indicates that a mean value of pixel values at the same position in "L(x,y)" and "R(x,y)" is allocated to the overlapped region, a pixel value of "L(x,y)" is allocated to the left side region, and a pixel value of "R(x,y)" is allocated to the right side region, thereby acquiring the mean image data "M(x,y)".

The calculating unit 153a calculates a coefficient distribution "cof(x,y)" from the mean image data "M(x,y)" as illustrated in FIG. 29. Specifically, the calculating unit 153a calculates "cof(x,y)" by Equation 27 below.

$$\begin{aligned} cof(x, y) &= \left(M(x, y)/\beta\right)^\alpha \\ &\text{(where when } M(x, y) > \beta, \, cof(x, y) = 1.0) \end{aligned} \quad (27)$$

In above Equation 27, an "α-th power" of a value obtained by dividing M(x,y) by "β" is defined as "cof(x,y)". Furthermore, in above Equation 27, it is defined that "cof(x,y)" is "1" when a value obtained by dividing "M(x,y)" by "β" is larger than "1". "α, β" are values that are set in advance. Specifically, "n" signifies an upper level of an output signal, and is set to a level equal to or lower than the maximum value "max" in an image signal. It is preferable that "β" be set to a level of about 70% to 80% of "max". Furthermore, it is preferable that an exponentiation value "α" be set to a value of about "¼ to ⅓".

A graph illustrated in FIG. 29 is a graph in which output values "cof(x,y)" that are calculated from input values "M(x,y)/β" using Equation 27 where "α=¼" are plotted. An advantage of calculating the coefficient distribution using a function including arithmetic processing in which the calculating unit 153a exponentiates an input value as in Equation 27 is explained later.

Subsequently, the multiplying unit 153b multiplies "CP_dot(x,y)" by the coefficient distribution "cof(x,y)" as illustrated in FIG. 29, and outputs output image data "Output(x,y)=CP_dot(x,y)*cof(x,y)". The control unit 18 then causes the monitor 2 to display the output image data "Output(x,y)" as B-mode image data.

The following describes reasons why "Output(x,y)" output by the above described processing becomes high quality image data in which multiple reflection is reduced and the lateral resolution and the sensitivity are maintained.

As with scattered signals, in a region where a signal level does not differ regardless of whether the region is viewed from the right or the left, the brightness of mean image data is high. In contrast, as with multiple reflection, in a region where a signal level is reduced by inclining a beam, the brightness of the mean image data is low. In particular, multiple reflection causes not only reductions in signal level due to deflection to the right and the left, but also changes in the appearance position corresponding to deflection to the right and the left. Accordingly, the degree of brightness reduction in the mean image data of the left-deflection image data and the right-deflection image data increases.

Thus, in the above described processing, in a region where the average brightness in the mean image data is high, which is considered to be a true signal component, the coefficient value contributing to the center image data to be finally output is made larger. In the above described processing, in a region where the average brightness in the mean image data is low, which is considered to be a noise component due to multiple reflection or the like, the coefficient value contributing to the center image data "CP_dot(x,y)" is made smaller. Thus, the above described processing enables further reduction of multiple reflection components for the center image data "CP_dot(x,y)". The image signal itself of the output image data derives from the center image data in which the lateral resolution is high and the sensitivity is also high, and thus the lateral resolution and the sensitivity are maintained in a region for which the coefficient value is large because of being considered to be a signal.

As for a converting method to acquire a coefficient value, which is output data, from mean image data, which is input data, it is desirable that for a degree of input intensity at such a level being a boundary of a signal and a noise, an output value be maintained high in a signal region, and an output value be sufficiently small in a noise region. As the simplest method to obtain such a conversion characteristics, threshold processing is conceivable in which an output value is set to "1" when an input value exceeds a predetermined threshold, and to "0" when the input value is equal to or smaller than the threshold.

However, a "signal-noise boundary level" used to set a threshold generally varies according to the subject P, and therefore, cannot be specifically determined. Accordingly, to obtain a robust multiple reflection reducing effect, using a conversion characteristic that smoothly varies with respect to an input and has a characteristic close to the threshold processing is effective.

For a specific method to obtain such a characteristic, it is preferable to give an output value by a "power function" according to an input level as indicated in above Equation 27. For example, in the conversion characteristics illustrated in FIG. 29, in a range in which "M(x,y)/β" is larger than "0.1", the coefficient value smoothly varies, and in a range in which "M(x,y)/β" is equal to or smaller than "0.1", the coefficient value abruptly decreases.

However, when the above coefficient control is performed, as is obvious from the graph in FIG. 29, in the output image data "Output(x,y)", a signal in a low brightness region is hardly displayed, and therefore, a display dynamic range appears to be narrow and a gain tends to decrease. Therefore, the control unit 18 may control, using a predetermined look up table (LUT), the display dynamic range and the gain at the time of displaying output image data so that image data on which the above multiplication processing is not performed and the display dynamic range and the gain on appearance are equivalent.

Next, a condition for generating "L(x,y)" and "R(x,y)" that are the input data to calculate the above described coefficient distribution is explained. For "L(x,y)" and "R(x,y)" to acquire the coefficient distribution, three cases are conceivable. In the first case, data used to calculate the coefficient distribution by the calculating unit 153a is data that is generated based on the normal aperture function. For example, the acquiring unit 151 acquires B-mode image data that is acquired by the normal apodization using the aperture function of the hamming window, as "L(x,y)" and "R(x,y)". The calculating unit 153a then calculates the coefficient distribution from mean image data of the two pieces of B-mode image data.

A reason why data acquired by the normal apodization when deflected rightward and leftward can be used as input sources of the coefficient distribution as the first case is explained below. For example, when a subject causing multiple reflection is inclined toward an upper right direction and a deflection angle is in the left direction, a reception position of a multiple reflection component is shifted toward a left end direction of the aperture a weight of which is small in the normal aperture function with elongation of a multiple reflection path. On the other hand, when the subject is inclined toward an upper right direction and the deflection angle is in the right direction, the multiple reflection component is received inside the reception aperture and the multiple reflection component becomes relatively large. However, a multiple reflection artifact of the deflection angle in the right direction is deemed to be reduced lower than that of B-mode image data with the normal deflection angle of "0 degrees".

Therefore, in terms of simplification of processing, it is preferable that each of two input sources to acquire the coefficient distribution be acquired by the normal apodization.

The second case is explained. In the second case, data used to calculate the coefficient distribution by the calculating unit 153a is data that is generated based on the inverse aperture function. Specifically, in the second case, data used to calculate the coefficient distribution by the calculating unit 153a is data that is generated based on the shifted inverse aperture-function explained in the second embodiment.

As explained in the second embodiment, by performing the shifted inverse apodization based on a direction of ultrasonic wave transmission/reception, the multiple reflection reducing effect can be reliably obtained even when deflected. Therefore, in the second case, by using data acquired in the shifted inverse apodization as the data to calculate the coefficient distribution, the coefficient distribution that can ensure reduction of a multiple reflection component can be acquired. The shifted inverse apodization used in the second case may be either of the first or of the second pattern explained in the second embodiment.

The third case is explained. In the third case, data used to calculate the coefficient distribution by the calculating unit 153a is data that is obtained by the multiplication of coefficients explained in the sixth embodiment, for example. For example, by performing the normal/inverse apodization using a left-deflected angle, "L(x,y)" is obtained by the processing explained in the sixth embodiment. For example, by performing the normal/inverse apodization using a right-deflected angle, "R(x,y)" is obtained by the processing explained in the sixth embodiment. In the third case, the shifted inverse apodization is performed as the inverse apodization, and the fixed normal apodization or the shifted normal apodization is performed as the normal apodization. In the third case, by using output data from the result of the multiplication using a coefficient of a compound signal acquired in the shifted-inverse apodization and the normal apodization as the data to calculate the coefficient distribution, the coefficient distribution that can reduce a multiple reflection component lower than that in the second case can be acquired. In the above three cases, "L(x,y)" and "R(x,y)" are preferably image data of tissue harmonic components.

In the above, a representative example in which a coefficient distribution is calculated using mean image data of left-deflected image data and right-deflected image data of any one of the first case to the third case, applying three directions (±θ degrees, 0 degrees) as the deflection angles has been given. Note that "inclined deflected image data" to calculate the coefficient distribution that can reduce multiple reflection independently of a coefficient such as "cos($\theta_{CP}$)" may be deflected image data deflected in either one direction of right or left. For example, the calculating unit 153a may calculate the coefficient distribution "cof(x,y)" by substituting "L(x,y)" into Equation 27.

However, a structure that is a multiple reflection source inside a scanning region of the subject P can be inclined, for example, relative to the direction of arrangement of transducer elements. Accordingly, to obtain a robust multiple reflection reducing effect using the coefficient distribution, it is preferable that the mean image data of the left-deflected image data and the right-deflected image data be used as described above.

Furthermore, in the ninth embodiment, the number of directions of the deflection angles may be increased to five or seven. In such a case, "(a): a method of increasing the number of addition directions of mean image data", "(b): a method of using image data obtained by performing compounding processing (for example, weighting processing) on a plurality of pieces of image data including front image data as the center image data", and "(c): a method using a combination of (a) and (b)" can be performed. An example of the front image data is "CP_dot(x,y)".

Note that the frame rate does not change from that at normal scanning of normal B-mode scanning even in the conventional method in which compounding processing is performed by frame sequence, or in the method according to the ninth embodiment in which multiplication processing using the coefficient and the coefficient distribution is performed by frame sequence. However, in both of the methods, because the corresponding number of frames to the number of directions are used for processing, the responsivity in change of images to movement of the ultrasound probe 1, movement of the subject P caused by respiration, and the like tends to be degraded as the number of directions increases. On the other hand, in both of the methods, the multiple reflection reducing effect becomes higher as the number of directions increases.

Accordingly, in the method according to the ninth embodiment, a trade-off between the responsivity and the multiple reflection reducing effect occurs according to the set number of directions. Therefore, it is preferable, in the ninth embodiment, that candidate sets of the number of directions be prepared in advance so that setting of "the overall number of directions" and "the number of directions used for generation processing of mean image data and the number of directions used for generation processing of center image data" is selectable by an operator according to a use. In such a case, an operator selects a desirable setting from candidate sets displayed, for example, on a GUI.

As described above, in the ninth embodiment, for example, the coefficient distribution is acquired from deflected image data acquired by frame sequence, and data that is obtained by multiplying front image data "CP_dot(x, y)" without deflection acquired by frame sequence by the coefficient distribution is output as B-mode image data. Thus, in the ninth embodiment, it is possible to acquire a higher quality image in which multiple reflection is further reduced than images acquired in the sixth embodiment, for example. In the above, the case in which a coefficient distribution acquired by frame sequence is applied has been explained. The above description is applicable to the seventh embodiment and the eighth embodiment.

Tenth Embodiment

In the tenth embodiment, a case is explained in which the multiple reflection reducing effect is further enhanced by using a different coefficient distribution that is acquired independently of the coefficient distribution explained in the ninth embodiment, using FIG. 30A through FIG. 30D, for example. FIG. 30A through FIG. 30D are diagrams for explaining the tenth embodiment.

The acquiring unit 151 according to the tenth embodiment further acquires a reception signal group that is constituted of a plurality of reception signals with various deflection angles by ultrasonic scanning in which deflection angles in ultrasonic wave transmission/reception are varied among rates. That is, in the tenth embodiment, ultrasonic scanning in which deflection angles are varied by the rate sequence explained using FIG. 4B is performed. The deflection angles include the deflection angle in the certain direction (0 degrees) used to acquire the two IQ signals.

The calculating unit 153a according to the tenth embodiment further calculates a coefficient distribution using at least one reception signal with a deflection angle in a direction other than the certain direction, from the reception signal group. Subsequently, the multiplying unit 153b according to the tenth embodiment multiplies, from the reception signal group, a reception signal with the deflection angle in the certain direction, or a signal that is obtained by compounding reception signals with respective deflection angles in a plurality of directions including the certain direction, by the coefficient and the coefficient distribution. Processing explained below is applicable to various kinds of signals (an IQ signal, an amplitude signal, and an image signal) that are regarded as reception signals.

In the rate sequence, to acquire a signal of a single reception scan line, ultrasonic wave transmission/reception with various deflection angles relative to a direction of this reception scan line as the center is performed more than once. For example, by the control of the control unit 18, the transceiving unit 11 causes the ultrasound probe 1 to execute ultrasonic wave transmission/reception in three directions (deflection angles: 0 degrees, +θ degrees, −θ degrees) in a rate unit. Thus, three reception signals with different deflection angles are acquired. The certain direction described above is the direction of the deflection angle of "0 degrees". The direction of the deflection angle of "0 degrees" is, for example, a direction to acquire "$IQ_1$, $IQ_2$, CP" explained in the sixth embodiment. The acquiring unit 151 acquires these three reception signals.

Figure 30A:
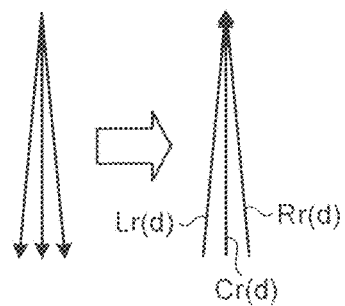
FIGS. 30A, 30B, 30C, and 30D are diagrams for explaining a tenth embodiment.

"Lr(d)" and "Rr(d)" illustrated in FIG. 30A are a left-deflected reception signal and a right-deflected reception signal, respectively, in which a multiple reflection component is reduced by inclined transmission and reception. Moreover, "Cr(d)" illustrated in FIG. 30A is a reception signal obtained by multiplying the compound signal CP by a coefficient, for example. "(d)" indicates a position in a depth direction (direction of a reception scan line) of a reception signal.

Figure 30B:
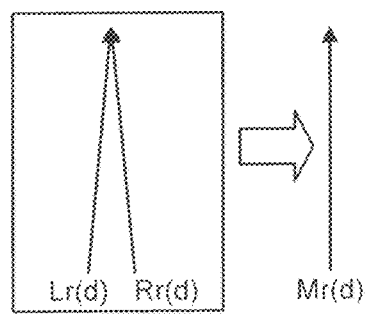
Figure 30C:
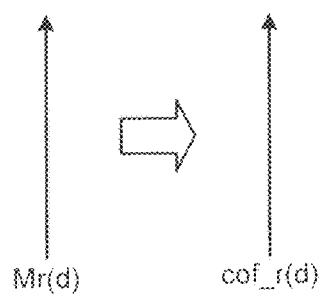
Figure 30D:
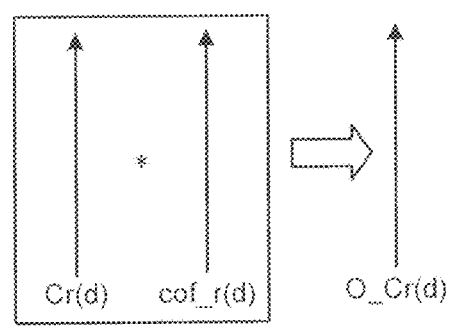

In FIG. 30B through FIG. 30D, a case is exemplified in which the calculating unit 153a calculates a coefficient distribution with "Lr(d)" and "Rr(d)" as subjects of processing, and the multiplying unit 153b multiplies "Cr(d)" by the coefficient distribution. The processing of multiplying "Cr(d)" by the coefficient distribution is equivalent to the processing of multiplying the compound signal CP with the deflection angle of "0 degrees" by the coefficient and the coefficient distribution.

As for "Lr(d)" and "Rr(d)" that are input data to calculate the coefficient distribution in the tenth embodiment, selecting data in which occurrence of multiple reflection is small is effective. The three cases explained in the ninth embodiment can be applied, when determining what kind of data is to be selected as "Lr(d)" and "Rr(d)". That is, in the first case according to the tenth embodiment, data that is generated based on the normal aperture function is used as the data ("Lr(d)" and "Rr(d)") used to calculate the coefficient distribution by the calculating unit 153a. Moreover, in the second case according to the tenth embodiment, data that is generated based on the shifted inverse aperture-function is used as the data ("Lr(d)" and "Rr(d)") used to calculate the coefficient distribution by the calculating unit 153a. Furthermore, in the third case according to the tenth embodiment, data that is acquired by performing multiplication processing on the coefficient acquired from the compound signal CP that is acquired by the normal apodization and the shifted inverse apodization is used as the data ("Lr(d)" and "Rr(d)") used to calculate the coefficient distribution by the calculating unit 153a.

Moreover, also in the tenth embodiment, it is preferable that the data that is used for calculation of the coefficient distribution by the calculating unit 153a is data for which a non-linear component is extracted to prevent mixing of side lobe components.

When the acquiring unit 151 acquires the data described above, the calculating unit 153a acquires a mean signal "Mr(d)" of "Lr(d)" and "Rr(d)" as illustrated in FIG. 30B. Specifically, the calculating unit 153a acquires "Mr(d)" by Equation 28 below.

$$Mr(d)=(Lr(d)+Rr(d))/2 \tag{28}$$

The calculating unit 153a then, as illustrated in FIG. 30C, calculates the coefficient distribution "cof_r(d)" to be given to "Cr(d)" in the depth direction "d" from the mean signal "Mr(d)". Specifically, the calculating unit 153a calculates "cof_r(d)" by Equation 29 below.

$$\left.\begin{array}{l}\text{cof\_r}(d) = \left(Mr(d)/\beta\right)^\alpha\\\text{(where when } Mr(d) > \beta, \text{cof\_r}(d) = 1.0)\end{array}\right\} \tag{29}$$

In above Equation 29, an "α-th power" of a value obtained by dividing Mr(d) by "β" is defined as "cof_r(d)". Furthermore, in above Equation 29, it is defined that "cof_r(d)" is "1" when a value obtained by dividing Mr(d) by "β" is larger than "1". "α, β" are values that are set in advance as explained in the ninth embodiment. Specifically, "β" signifies an upper level of an output reception signal, and is set to a level equal to or lower than the maximum value "max" of a reception signal. It is preferable that "β" be set to a level of about 70% to 80% of "max". Furthermore, it is preferable that "α" be set to a value of about "¼ to ⅓". An advantage of calculating the coefficient distribution using a function including arithmetic processing in which the calculating unit 153a exponentiates an input value as in Equation 29 is similar to the reason explained in the calculation processing of the coefficient distribution "cof(x,y)".

Subsequently, the multiplying unit 153b multiplies "Cr(d)" by the coefficient distribution "cof_r(d)" as illustrated in FIG. 30D, and outputs an output reception signal "θ_Cr(d)".

The data processing unit 15 performs the above described processing for all of reception scan lines, to output an output reception signal of one frame. By the control of the control unit 18, the image generating unit 14 generates output image data from an output reception-signal group of one frame. The monitor 2 displays output image data by the control of the control unit 18. The output image data is high quality image data in which multiple reflection is reduced and the lateral resolution and the sensitivity are maintained by a synergistic effect of the coefficient based on "$θ_{CP}$" and the coefficient distribution. Also in the tenth embodiment, the control unit 18 may control, using a predetermined LUT, the display dynamic range and the gain at the time of displaying output image data so that image data on which the multiplication processing is not performed and the display dynamic range and the gain on appearance are equivalent.

In the tenth embodiment, as explained in the ninth embodiment, one inclined reception signal (for example, "Lr(d)") may be used to calculate the coefficient distribution. Furthermore, also in the tenth embodiment, the number of directions of the deflection angles may be increased to five or seven as explained in the ninth embodiment.

When the above application examples are performed, in the tenth embodiment, similarly to the ninth embodiment, it is preferable that candidate sets of the number of directions be prepared in advance so that setting of "the overall number of directions" and "the number of directions used for generation processing of a mean signal and the number of directions used for generation processing of a center signal" is selectable by an operator according to a use.

As described above, in the tenth embodiment, by performing the multiplication processing using the coefficient based on "$\theta_{CP}$" and the coefficient distribution "cof_r(d)", it is possible to acquire a higher quality image in which multiple reflection is further reduced than images acquired in the conventional method in which the spatial compounding among rates is performed, or in the sixth embodiment. The above description is applicable to the seventh embodiment and the eighth embodiment.

Eleventh Embodiment

In the eleventh embodiment, a case is explained in which the multiple reflection reducing effect is further enhanced by using a different coefficient distribution that is acquired independently of the coefficient distributions explained in the ninth embodiment and the tenth embodiment, using FIG. 31A through FIG. 31D, for example. FIG. 31A through FIG. 31D are diagrams for explaining the eleventh embodiment.

The acquiring unit 151 according to the eleventh embodiment further acquires a simultaneous reception-signal group that is constituted of a plurality of simultaneous reception signals with various deflection angles generated by ultrasonic scanning in which reflected waves of a plurality of reception deflection angles are received by parallel simultaneous reception for transmission ultrasonic waves. That is, in the eleventh embodiment, ultrasonic scanning in which deflection angles are varied in the parallel simultaneous reception explained using FIG. 4A is performed. The certain direction described above is the direction of the deflection angle of "0 degrees". The direction of the deflection angle of "0 degrees" is, for example, a direction to acquire "$IQ_1$, $IQ_2$, CP" explained in the sixth embodiment.

The calculating unit 153a according to the eleventh embodiment further calculates a coefficient distribution using at least one simultaneous reception signal with a deflection angle in a direction other than the certain direction, from the simultaneous reception-signal group. Subsequently, the multiplying unit 153b according to the eleventh embodiment multiplies, from the simultaneous reception-signal group, a simultaneous reception signal with the deflection angle in the certain direction, or a signal that is obtained by compounding simultaneous reception signals with respective deflection angles in a plurality of directions including the certain direction, by the coefficient based on "$\theta_{CP}$" and the coefficient distribution. Processing explained below is applicable to various kinds of signals (an IQ signal, an amplitude signal, and an image signal) that are regarded as reception signals.

For example, by the control of the transceiving unit 11 through the control unit 18, the ultrasound probe 1 transmits an ultrasonic beam in a direction of the deflection angle of "0 degrees", and receives reflected waves in three directions (deflection angles: 0 degrees, +θ degrees, −θ degrees) simultaneously. Thus, three simultaneous reception signals with different deflection angles are acquired. The acquiring unit 151 acquires these three reception signals.

Figure 31A:
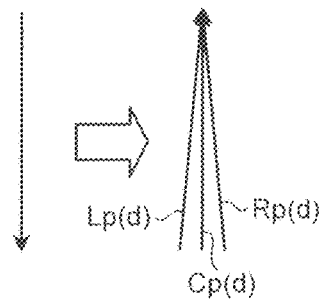
FIGS. 31A, 31B, 31C, and 31D are diagrams for explaining an eleventh embodiment.

"Lp(d)" and "Rp(d)" illustrated in FIG. 31A are a left-deflected simultaneous-reception signal and a right-deflected simultaneous-reception signal, respectively, in which a multiple reflection component is reduced by inclined transmission and reception. Moreover, "Cp(d)" illustrated in FIG. 31A is a reception signal obtained by multiplying the compound signal CP by a coefficient, for example. "(d)" indicates a position in a depth direction (direction of a reception scan line) of a reception signal.

Figure 31B:
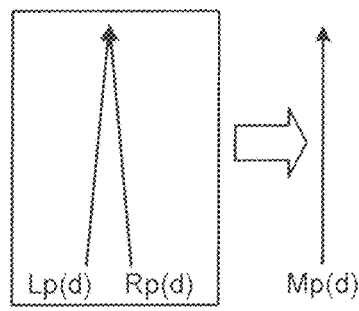
Figure 31C:
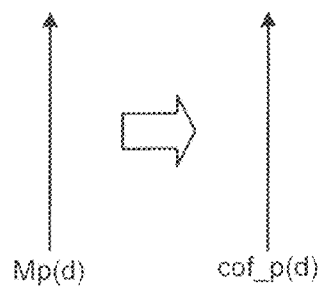
Figure 31D:
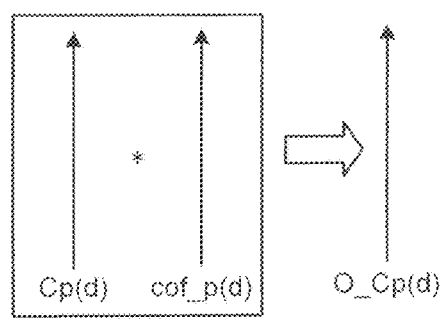

In FIG. 31B through FIG. 31D, a case is exemplified in which the calculating unit 153a calculates a coefficient distribution with "Lp(d)" and "Rp(d)" as subjects of processing, and the multiplying unit 153b multiplies "Cp(d)" by the coefficient distribution. The processing of multiplying "Cp(d)" by the coefficient distribution is equivalent to the processing of multiplying the compound signal CP with the deflection angle of "0 degrees" by the coefficient and the coefficient distribution.

As for "Lp(d)" and "Rp(d)" that are input data to calculate the coefficient distribution in the eleventh embodiment, selecting data in which occurrence of multiple reflection is small is effective. The three cases explained in the ninth embodiment can be applied, when determining what kind of data is to be selected as "Lp(d)" and "Rp(d)". That is, in the first case according to the eleventh embodiment, data that is generated based on the normal aperture function is used as the data ("Lp(d)" and "Rp(d)") used to calculate the coefficient distribution by the calculating unit 153a. Moreover, in the second case according to the eleventh embodiment, data that is generated based on the shifted inverse aperture-function is used as the data ("Lp(d)" and "Rp(d)") used to calculate the coefficient distribution by the calculating unit 153a. Furthermore, in the third case according to the eleventh embodiment, data that is acquired by performing multiplication processing on the coefficient acquired from the compound signal CP that is acquired by the normal apodization and the shifted inverse apodization is used as the data ("Lp(d)" and "Rp(d)") used to calculate the coefficient distribution by the calculating unit 153a.

Moreover, also in the eleventh embodiment, it is preferable that the data that is used for calculation of the coefficient distribution by the calculating unit 153a is data for which a non-linear component is extracted to prevent mixing of side lobe components.

When the acquiring unit 151 acquires the data described above, the calculating unit 153a acquires a mean signal "Mp(d)" of "Lp(d)" and "Rp(d)" as illustrated in FIG. 31B. Specifically, the calculating unit 153a acquires "Mp(d)" by Equation 30 below.

$$Mp(d)=(Lp(d)+Rp(d))/2 \tag{30}$$

The calculating unit 153a then, as illustrated in FIG. 31C, calculates the coefficient distribution "cof_p(d)" to be given to "Cp(d)" in the depth direction "d" from the mean signal "Mp(d)". Specifically, the calculating unit 153a calculates "cof_p(d)" by Equation 31 below.

$$\left.\begin{array}{r}\text{cof\_p}(d) = \left(Mp(d)/\beta\right)^\alpha \\ (\text{where when } Mp(d) > \beta, \text{cof\_p}(d) = 1.0)\end{array}\right\} \tag{31}$$

In above Equation 31, an "α-th power" of a value obtained by dividing Mp(d) by "β" is defined as "cof_p(d)". Furthermore, in above Equation 31, it is defined that "cof_p(d)" is "1" when a value obtained by dividing Mp(d) by "β" is larger than "1". "α, β" are values that are set in advance as explained in the ninth embodiment and the tenth embodiment. Specifically, "β" signifies an upper level of an output reception signal, and is set to a level equal to or lower than the maximum value "max" of a reception signal. It is preferable that "β" be set to a level of about 70% to 80% of "max". Furthermore, it is preferable that "α" be set to a value of about "¼ to ⅓". An advantage of calculating the coefficient distribution using a function including arithmetic processing in which the calculating unit 153a exponentiates an input value as in Equation 31 is similar to the reason explained in the calculation processing of the coefficient distribution "cof(x,y)".

The multiplying unit 153b multiplies "Cp(d)" by the coefficient distribution "cof_p(d)" as illustrated in FIG. 31D, and outputs an output reception signal "O_Cp(d)".

The data processing unit 15 performs the above described processing for all of reception scan lines, to output an output reception signal of one frame. By the control of the control unit 18, the image generating unit 14 generates output image data from an output reception-signal group of one frame. The monitor 2 displays output image data by the control of the control unit 18. The output image data is high quality image data in which multiple reflection is reduced and the lateral resolution and the sensitivity are maintained by a synergistic effect of the coefficient based on "$\theta_{CP}$" and the coefficient distribution. Also in the eleventh embodiment, the control unit 18 may control, using a predetermined LUT, the display dynamic range and the gain at the time of displaying output image data so that image data on which the multiplication processing is not performed and the display dynamic range and the gain on appearance are equivalent.

In the eleventh embodiment, as explained in the ninth embodiment and the tenth embodiment, one inclined reception signal (for example, "Lp(d)") may be used to calculate the coefficient distribution. Furthermore, also in the eleventh embodiment, the number of directions of the deflection angles may be increased to five or seven as explained in the ninth embodiment and the tenth embodiment.

When the above application examples are performed, in the eleventh embodiment, similarly to the ninth embodiment and the tenth embodiment, it is preferable that candidate sets of the number of directions be prepared in advance so that setting of "the overall number of directions" and "the number of directions used for generation processing of a mean signal and the number of directions used for generation processing of a center signal" is selectable by an operator according to a use.

As described above, in the eleventh embodiment, by performing the multiplication processing using the coefficient based on "$\theta_{CP}$" and the coefficient distribution "cof_p (d)", it is possible to acquire a higher quality image in which multiple reflection is further reduced than images acquired in the conventional method in which the spatial compounding is performed by parallel simultaneous reception, or in the sixth embodiment. The above description is applicable to the seventh embodiment and the eighth embodiment.

The processing described in the ninth embodiment through the eleventh embodiment can be performed in any combination. That is, in the scan mode of frame sequence explained in the ninth embodiment (hereinafter, first scan mode), a scan mode of rate sequence explained in the tenth embodiment (hereinafter, second scan mode), and a scan mode of parallel simultaneous reception explained in the eleventh embodiment (hereinafter, third scan mode), each of deflection angles can be set independently. Therefore, the operation explained in the ninth embodiment through the eleventh embodiment can be arbitrarily combined with the processing using the coefficient based on "$\theta_{CP}$" explained in the sixth embodiment through the eighth embodiment. This operation enables both the multiple reflection reducing effect and the maintenance of the lateral resolution and the sensitivity to be achieved.

Moreover, when at least two out of the three kinds of scan modes are combined to be used, multiplication processing using a coefficient distribution acquired in each mode is performed at least in one of the scan modes, and a conventional method (compounding processing) may be performed in the rest of the scan modes. This operation also enables both the multiple reflection reducing effect and the maintenance of the lateral resolution and the sensitivity to be achieved.

In the ninth embodiment through the eleventh embodiment described above, a case has been explained in which a mean value of a plurality of directions is applied to an image signal having deflection or a reception signal having deflection at calculation of various coefficient distributions. However, in the ninth embodiment through the eleventh embodiment described above, coefficient distributions can be calculated from a cross-correlation value or a difference among signals of a plurality of directions, and the like.

Twelfth Embodiment

Figure 32:
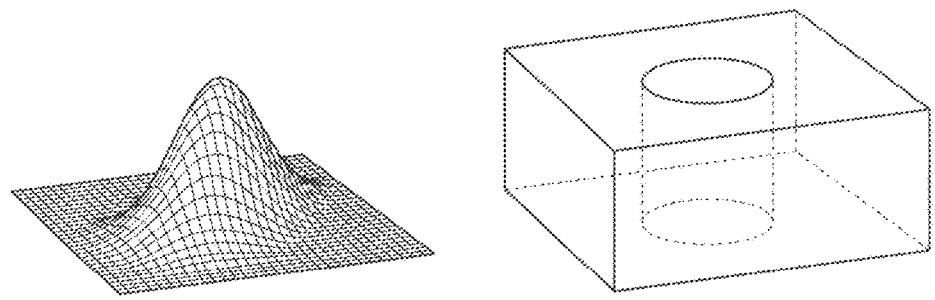
FIG. 32 is a diagram (1) for explaining a twelfth embodiment.
Figure 33:
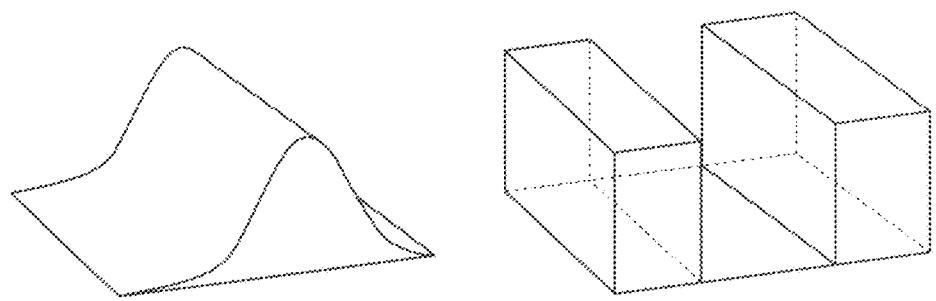
FIG. 33 is a diagram (2) for explaining the twelfth embodiment.
Figure 34:
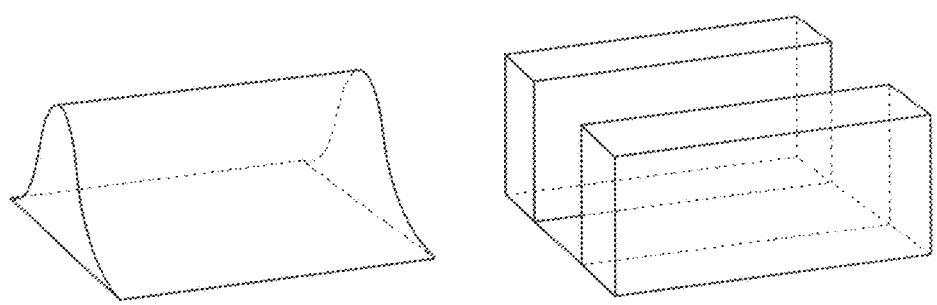
FIG. 34 is a diagram (3) for explaining the twelfth embodiment.

In the twelfth embodiment, a case is explained in which a mechanical 4D probe or a 2D array probe is used as the ultrasound probe 1 to perform three-dimensional scanning, using FIG. 32 through FIG. 34. FIG. 32 through FIG. 34 are diagrams for explaining the twelfth embodiment.

That is, the ultrasonic imaging method explained in the first embodiment through the eleventh embodiment is applicable not only to when two-dimensional ultrasonic image data is imaged, but also to when volume data is imaged. For example, when a mechanical 4D probe is used as the ultrasound probe 1, by compounding a plurality of tomograms acquired by mechanically swinging a transducer element group, volume data is generated. In such a case, performing the ultrasonic imaging method explained in the first embodiment through the eleventh embodiment described above can ensure improvement in image quality of image data obtained by signal compounding.

Furthermore, for example, in the sixth embodiment through the eleventh embodiment, two respective aperture functions for obtaining two IQ signals using the 2D array probe are roughly classified into the following two cases.

In the first case, an aperture function in which an weighting pattern used for a one-dimensional reception aperture is applied to both directions of a two-dimensional reception aperture, is used as each of the two aperture functions. For example, an aperture function illustrated in the left figure in FIG. 32 is a normal aperture function in which a weighting pattern of the one-dimensional normal aperture function of the hamming window is applied to each of the azimuth direction and the elevation direction. Furthermore, for example, an aperture function illustrated in the right figure in FIG. 32 is an inverse aperture function in which a weighting pattern of the one-dimensional inverse aperture function in which the center portion is zero is applied to each of the azimuth direction and the elevation direction. The right figure in FIG. 32 exemplifies a case in which the shape of the zero center portion is a column; however, the shape of the zero center portion may be a cuboid.

In the first case, "$IQ_1$" is output by the normal aperture function illustrated in the left figure in FIG. 32, and "$IQ_2$" is output by the inverse aperture function illustrated in the right figure in FIG. 32. Thus, processing performed by the data processing unit 15 is the same as that in the embodiments described above.

In the second case, for example, the reception apodization is separately performed on the azimuth direction and the elevation direction, and the normal apodization and the inverse apodization are performed on each of the directions. It is supposed that two aperture functions for sectional scanning are a first aperture function (for example, the one-dimensional normal aperture function of the hamming window) and a second aperture function (for example, the one-dimensional inverse aperture function in which the center portion is zero), having different weighting patters for the one-dimensional reception aperture.

In such a case, the following four types of aperture functions can be set for a two-dimensional reception aperture: "an aperture function in which a weighting pattern of the first aperture function is applied to one direction of the two-dimensional reception aperture", "an aperture function in which a weighting pattern of the first aperture function is applied to the other direction of the two-dimensional reception aperture", "an aperture function in which a weighting pattern of the second aperture function is applied to the one direction of the two-dimensional reception aperture", and "an aperture function in which a weighting pattern of the second aperture function is applied to the other direction of the two-dimensional reception aperture".

The left figure in FIG. 33 is one example of the "aperture function in which a weighting pattern of the first aperture function is applied to one direction of a two-dimensional reception aperture", and is a normal aperture function "NormApod-a" in which a weighting pattern of the one-dimensional normal aperture function of the hamming window is applied to the azimuth direction. The right figure in FIG. 33 is one example of the "aperture function in which a weighting pattern of the second aperture function is applied to the one direction of the two-dimensional reception aperture", and is an inverse aperture function "InvApod-a" in which a weighting pattern of the one-dimensional inverse aperture function in which the center portion is zero is applied to the azimuth direction.

The left figure in FIG. 34 is one example of the "aperture function in which a weighting pattern of the first aperture function is applied to the other direction of the two-dimensional reception aperture", and is a normal aperture function "NormApod-e" in which a weighting pattern of the one-dimensional normal aperture function of the hamming window is applied to the elevation direction. The right figure in FIG. 34 is one example of the "aperture function in which a weighting pattern of the second aperture function is applied to the other direction of a two-dimensional reception aperture", and is the inverse aperture function "InvApod-e" in which a weighting pattern of the one-dimensional inverse aperture function in which the center portion is zero is applied to the elevation direction.

In such a case, the acquiring unit 151 acquires a first IQ signal (hereinafter, IQ1$a$) output by the normal aperture function "NormApod-a", a second IQ signal (hereinafter, IQ1$e$) output by the normal aperture function "NormApod-e", a third IQ signal (hereinafter, IQ2$a$) output by the inverse aperture function "InvApod-a", and a fourth IQ signal (hereinafter, IQ2$e$) output by the inverse aperture function "InvApod-e".

The compounding unit 152 then performs compounding processing on any one of the following two combinations. In a first combination, the compounding unit 152 generates a first compound signal from IQ1$a$ and IQ2$a$ and a second compound signal from IQ1$e$ and IQ2$e$ by non-linear processing. In a second combination, the compounding unit 152 generates the first compound signal from IQ1$a$ and IQ2$e$ and the second compound signal from IQ1$e$ and IQ2$a$ by non-linear processing.

The signal processing unit 153 then performs, for example, the signal processing explained in the sixth embodiment through the eighth embodiment on each of the first compound signal and the second compound signal obtained in the first combination. Alternatively, the signal processing unit 153 performs, for example, the signal processing explained in the sixth embodiment through the eighth embodiment on each of the first compound signal and the second compound signal obtained in the second combination.

Accordingly, by the control of the control unit 18, one of the following two types of image data is finally displayed on the monitor 2. That is, the control unit 18 causes the monitor 2 to display image data that is generated from a signal obtained by performing coherent addition on the first compound signal and the second compound signal subjected to signal processing. Alternatively, the control unit 18 causes the monitor 2 to display image data that is generated from a signal obtained by performing incoherent addition on the first compound signal and the second compound signal subjected to signal processing.

The image data that is generated from the signal obtained by performing coherent addition on the first compound signal and the second compound signal subjected to signal processing is image data in which the lateral resolution is high. The image data that is generated from the signal obtained by performing incoherent addition on the first compound signal and the second compound signal subjected to signal processing is image data in which speckle noise is reduced.

When the first combination described above is used, and an object causing specular multiple reflection is parallel to an axis in the azimuth direction and an axis in the elevation direction viewed from the ultrasound probe 1 side, the multiple reflection reducing effect is high. When the second combination described above is used, and an object causing specular multiple reflection is rotated at 45 degrees from an axis in the azimuth direction and an axis in the elevation direction viewed from the ultrasound probe 1 side, the multiple reflection reducing effect is high.

Accordingly, when implementing the second case using a 2D array probe, there are four options, which are performing: coherent addition in the first combination, incoherent addition in the first combination, coherent addition in the second combination, and incoherent addition in the second combination. An image interpreter can select processing content according to the effect obtained from each of the four options.

The ultrasonic imaging method explained in the first embodiment through the twelfth embodiment may be performed by a data processing apparatus (signal processing apparatus) that is arranged independently of the ultrasonography apparatus, and has functions of the data processing unit 15 and the control unit 18 described above, for example. That is, in the signal processing apparatus, the acquiring unit acquires a plurality of IQ signals obtained by performing a plurality of processing with different conditions on reflected wave signals generated at a transducer element included in an ultrasound probe. The compounding unit generates a compound signal compounded by non-linear processing of the IQ signals. The control unit causes a display unit to display image data based on the compound signal. The signal processing apparatus corresponds to, for example, a computer such as a personal computer or a workstation.

Furthermore, among respective processing explained in the first embodiment through the twelfth embodiment, all or a part of processing that has been explained as one automatically performed may also be performed manually, or all or a part of processing that has been explained as one manually performed may also be performed automatically by a widely known method. In this case, the processing procedures, the control procedures, the specific names, and the information including various kinds of data and parameters indicated in the above document and the drawings can be changed arbitrarily unless otherwise specified.

Moreover, the illustrated components of the devices are functionally conceptual, and they are not necessarily required to be configured physically as illustrated. That is, specific forms of distribution and integration of the devices are not limited to ones illustrated, and all or a part thereof can be configured in a functionally or physically distributed or integrated manner in arbitrary units according to various kinds of loads and use conditions. Furthermore, as for the functions of processing performed in respective devices, all or a part thereof can be implemented by a central processing unit (CPU) and by a program that is analyzed and executed in the CPU, or can be implemented as hardware by wired logic.

Other Embodiments

Figure 35:
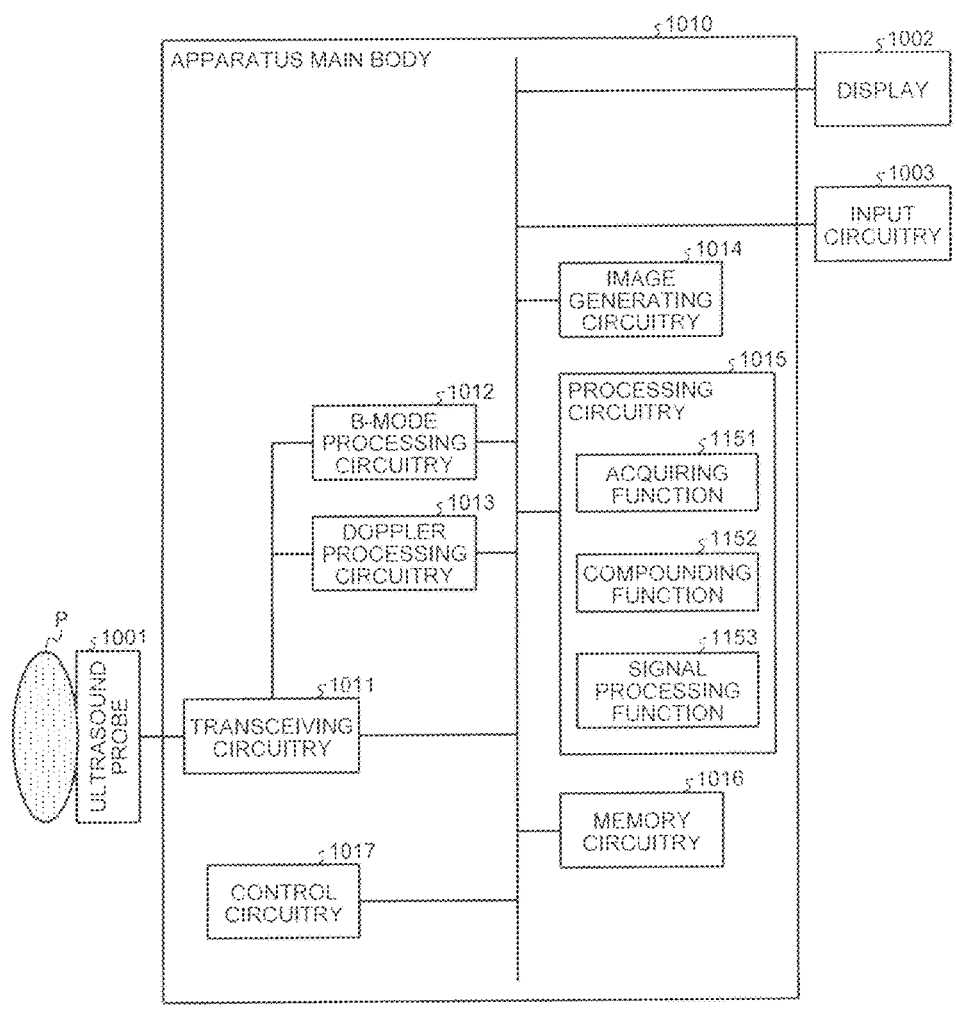
FIG. 35 is a block diagram illustrating the configuration of an ultrasonography apparatus according to other embodiments.

For example, the ultrasonography apparatus shown in FIG. 1 may be configured as shown in FIG. 35. FIG. 35 is a block diagram illustrating the configuration of an ultrasonography apparatus according to other embodiments.

As illustrated in FIG. 35, an ultrasonography apparatus includes an ultrasonic probe 1001, a display 1002, input circuitry 1003, and an apparatus main body 1010. The ultrasonic probe 1001, the display 1002, the input circuitry 1003, and the apparatus main body 1010 correspond to the ultrasonic probe 1, the monitor 2, the input device 3, and the apparatus main body 10 shown in FIG. 1, respectively.

The apparatus main body 1010 includes transceiving circuitry 1011, B-mode processing circuitry 1012, Doppler processing circuitry 1013, image generating circuitry 1014, processing circuitry 1015, memory circuitry 1016, and control circuitry 1017. The transceiving circuitry 1011, the reception circuitry 1012, the processing circuitry 1015, the B-mode processing circuitry 1012, the Doppler processing circuitry 1013, the image generating circuitry 1014, and the control circuitry 1017 correspond to the transceiving unit 11, the B-mode processing unit 12, the Doppler processing unit 13, the image generating unit 14, the data processing unit 15, and the control unit 18 shown in FIG. 1, respectively. The memory circuitry 1016 correspond to the image memory 16 and the internal storage unit 17 shown in FIG. 1. The processing circuitry 1015 is an example of processing circuitry in the accompanying claims. The control circuitry 1017 is an example of control circuitry in the accompanying claims.

The processing circuitry 1015 performs an acquiring function 1151, a compounding function 1152, and a signal processing function 1153. The acquiring function 1151 is a function implemented by the acquiring unit 151 illustrated in FIG. 1. The compounding function 1152 is a function implemented by the compounding unit 152 illustrated in FIG. 1. The signal processing function 1153 is a function implemented by the signal processing unit 153 illustrated in FIG. 1.

For example, each of the respective processing functions performed by the acquiring function 1151, the compounding function 1152, and the signal processing function 1153 which are components of the processing circuitry 1015 illustrated in FIG. 35, is stored in the memory circuitry 1016 in a form of a computer-executable program. The processing circuitry 1015 is a processor that loads programs from the memory circuitry 1016 and executes the programs so as to implement the respective functions corresponding to the programs. In other words, the processing circuitry 1015 that has loaded the programs has the functions illustrated in the processing circuitry 1015 in FIG. 35. That is, the processing circuitry 1015 loads a program corresponding to the acquiring function 1151 from the memory circuitry 1016 and executes the program so as to perform the same processing as that of the acquiring unit 151. The processing circuitry 1015 loads a program corresponding to the compounding function 1152 from the memory circuitry 1016 and executes the program so as to perform the same processing as that of the compounding unit 152. The processing circuitry 1015 loads a program corresponding to the signal processing function 1153 from the memory circuitry 1016 and executes the program so as to perform the same processing as that of the signal processing unit 153.

Figure 36:
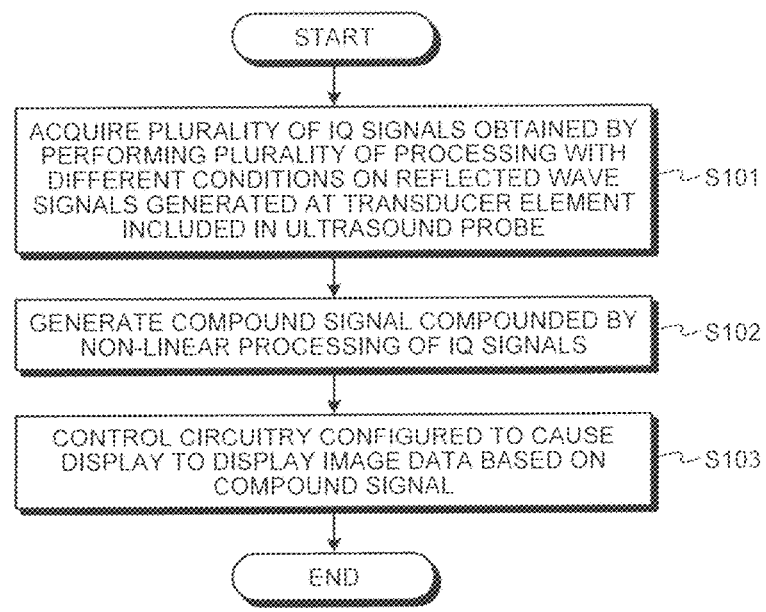
FIG. 36 is a flowchart of a processing procedure of the ultrasonography apparatus according to other embodiments.

FIG. 36 is a flowchart of a processing procedure of the ultrasonography apparatus according to other embodiments. As shown in FIG. 36, processing circuitry 1015 acquires a plurality of IQ signals obtained by performing a plurality of processing with different conditions on reflected wave signals generated at a transducer element included in an ultrasound probe 1001 (step S101). The processing circuitry 1015 generates a compound signal compounded by non-linear processing of the IQ signals (step S102). The control circuitry causes a display 1002 to display image data based on the compound signal (step S103).

For example, Steps S101 illustrated in FIG. 36 is a step that is implemented by the processing circuitry 1015 loading the program corresponding to the acquiring function 1151 from the memory circuitry 1016 and executing the program. Step S102 illustrated in FIG. 36 is a step that is implemented by the processing circuitry 1015 loading the program corresponding to the compounding function 1152 from the memory circuitry 1016 and executing the program.

In FIG. 35, the processing functions performed by the acquiring function 1151, the compounding function 1152, and the signal processing function 1153 are described as being implemented in the single processing circuit (signal processing circuitry). The functions, however, may be implemented by configuring a processing circuit by combining a plurality of separate processors and causing each of the processors to execute a program.

The term "processor" used in the above description means, for example, a central preprocess unit (CPU) and a graphics processing unit (GPU), or a circuit such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in a storage circuit. Instead of being stored in a storage circuit, the program may be built directly in a circuit of the processor. In this case, the processor implements a function by loading and executing the program built in the circuit. The processors in the present embodiment are not limited to a case in which each of the processors is configured as a single circuit. A plurality of separate circuits may be combined as one processor that implements the respective functions. Furthermore, the components illustrated in FIG. 35 may be integrated into one processor that implements the respective functions.

The respective circuitry exemplified in FIG. 35 may be distributed or integrated as appropriate. For example, the processing circuitry 1015 and the control circuitry 1017 may be integrated.

Moreover, the ultrasonic imaging method explained in the first embodiment through the twelfth embodiment can be implemented by executing an ultrasonic imaging program that is prepared in advance by a computer such as a personal computer and a workstation. This ultrasonic imaging method can be distributed through a network such as the Internet. Furthermore, this ultrasonic imaging method can be stored in a computer-readable recording medium such as a hard disk, a flexible disk (FD), a compact-disc read-only memory (CD-ROM), a magneto optical disc (MO), and a digital versatile disc (DVD), and can be executed by being read by a computer form the recording medium.

As explained above, according to the first embodiment through the twelfth embodiment, improvement in image quality of image data obtained by signal compounding is ensured.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A signal processing apparatus comprising processing circuitry configured to:
   acquire a first in-phase and quadrature-phase (IQ) signal by performing reception beam forming on reflected wave signals generated at a transducer element included in an ultrasound probe in electronic communication with the processing circuitry, using a first aperture function;
   acquire a second IQ signal by performing reception beam forming on the reflected wave signals, using a second aperture function having a weighting pattern different from that of the first aperture function;
   generate a third IQ signal by multiplying the first IQ signal and the second IQ signal by a calculated complex conjugate of either the first IQ signal or the second IQ signal;
   calculate one coefficient or a plurality of types of coefficients from phase information included in the third IQ signal;
   generate a fourth IQ signal by performing signal processing using the calculated one coefficient or any one of the plurality of types of coefficients, and at least one IQ signal from the first IQ signal the second IQ signal, and the third IQ signal;
   generate image data based on the fourth IQ signal; and
   cause a display to display the image data.

2. The signal processing apparatus according to claim 1, wherein the processing circuitry is configured to generate the third IQ signal from the first IQ signal and the second IQ signal by calculating a numerator of a complex correlation that is a real and imaginary number correlation.

3. The signal processing apparatus according to claim 1, wherein the processing circuitry is configured to detect phase information from the third IQ signal and perform processing using the detected phase information, as the signal processing.

4. The signal processing apparatus according to claim 1, wherein the processing circuitry is configured to perform spatial complex filtering as the signal processing.

5. The signal processing apparatus according to claim 1, wherein at least one of the first IQ signal and the second IQ signal is a signal for which a harmonic component is extracted.

6. The signal processing apparatus according to claim 1, wherein the first aperture function and the second aperture function include at least one of an inverse aperture function that is an aperture function in which a weight of a range including a reception position at which a multiple reflection component is received at the reception aperture is smaller than a weight of outside of the range including the reception position, and a normal aperture function that is an aperture function in which a weight of a range including a reception position at which a signal component is received at the reception aperture is larger than a weight of the outside of the range including the reception position.

7. The signal processing apparatus according to claim 1, wherein the processing circuitry is further configured to generate the fourth IQ signal by multiplying the third IQ signal by the one coefficient or any one of the coefficients.

8. The signal processing apparatus according to claim 1, wherein the processing circuitry is further configured to
   generate the fourth IQ signal by multiplying one of the first IQ signal and the second IQ signal by the one coefficient or any one of the coefficients.

9. The signal processing apparatus according to claim 1, wherein the processing circuitry is further configured to:
   generate a fifth IQ signal by multiplying the third IQ signal by the one coefficient or any one of the coefficients;
   generate a sixth IQ signal by multiplying one of the first IQ signal and the second IQ signal by the one coefficient or any one of the coefficients; and
   generate the fourth IQ signal by compounding the fifth IQ signal and the sixth IQ signal.

10. The signal processing apparatus according to claim 7, wherein a coefficient calculated by the processing circuitry from the third IQ signal has a value that increases or decreases depending on magnitude of correlation between the first IQ signal and the second IQ signal detected from phase information included in the third IQ signal.

11. The signal processing apparatus according to claim 1, wherein the ultrasound probe that performs ultrasonic wave transmission and reception is a two-dimensional array probe, and each of the two aperture functions is an aperture function in which a weighting pattern used for a one-dimensional reception aperture is applied to both directions of a two-dimensional reception aperture.

12. A signal processing apparatus comprising processing circuitry configured to:
   perform, on reflected wave signals generated at a transducer element included in an ultrasound probe which is a two-dimensional array probe in electronic communication with the processing circuitry, parallel processing of reception beam forming in two systems using a first aperture function and a second aperture function having different weighting patterns for a one-dimensional reception aperture,
   acquire, by the parallel processing, a first in-phase and quadrature-phase (IQ) signal that is output using an aperture function in which the weighting pattern of the first aperture function is applied to one direction of a two-dimensional reception aperture, a second IQ signal that is output using an aperture function in which a weighting pattern of the first aperture function is applied to the other direction of the two-dimensional reception aperture, a third IQ signal that is output using an aperture function in which the weighting pattern of the second aperture function is applied to the one direction, and a fourth IQ signal that is output using an aperture function in which a weighting pattern of the second aperture function is applied to the other direction, generate a first compound signal that is a signal formed from a multiplication operation involving the first IQ signal and the third IQ signal, and a second compound signal that is a signal formed from a multiplication operation involving the second IQ signal and the fourth IQ signal, or, a first compound signal that is a signal formed from a multiplication operation involving the first IQ signal and the fourth IQ signal, and a second compound signal that is a signal formed from a multiplication operation involving the second IQ signal and the third IQ signal, and perform complex (real and imaginary) signal processing on each of the first compound signal and the second compound signal; and cause a display to display image data that is generated from a signal obtained by performing coherent addition or incoherent addition on the first compound signal and the second compound signal subjected to the signal processing.

13. The signal processing apparatus according to claim 1, wherein the processing circuitry is further configured to acquire a plurality of reception signals with various deflection angles other than that in a certain direction used to acquire the two IQ signals, calculate a coefficient distribution using at least one reception signal from the plurality of reception signals, and generate second image data by multiplying the image data by the coefficient distribution; and cause the display to display the second image data.

14. The signal processing apparatus according to claim 1, wherein the signal processing apparatus is an ultrasonography apparatus.

15. The signal processing apparatus according to claim 1, wherein the processing circuitry is further configured to:

generate a seventh IQ signal and an eighth IQ signal by multiplying the first IQ signal and the second IQ signal respectively by two respective coefficients among the coefficients; and generate the fourth IQ signal by compounding the seventh IQ signal and the eighth IQ signal.

16. The signal processing apparatus according to claim 1, wherein the processing circuitry is further configured to:

generate a fifth IQ signal by multiplying the third IQ signal by the one coefficient or any one of the coefficients;

generate a seventh IQ signal and an eighth IQ signal by multiplying the first IQ signal and the second IQ signal respectively by two respective coefficients among the coefficients;

generate a ninth IQ signal by compounding the seventh IQ signal and the eighth IQ signal; and generate the fourth IQ signal by compounding the fifth IQ signal and the ninth IQ signal.

* * * * *